(12) United States Patent
Chenoweth et al.

(10) Patent No.: US 10,174,083 B2
(45) Date of Patent: Jan. 8, 2019

(54) AZA-AMINO ACID COLLAGEN COMPOUNDS

(71) Applicant: The Trustees of the University of Pennsylvania, Philadelphia, PA (US)

(72) Inventors: David M. Chenoweth, Philadelphia, PA (US); Yitao Zhang, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/581,815

(22) Filed: Apr. 28, 2017

(65) Prior Publication Data

US 2018/0079785 A1 Mar. 22, 2018

Related U.S. Application Data

(60) Provisional application No. 62/329,069, filed on Apr. 28, 2016.

(51) Int. Cl.
*C07K 9/00* (2006.01)
*C07K 14/00* (2006.01)

(52) U.S. Cl.
CPC .................................. *C07K 14/001* (2013.01)

(58) Field of Classification Search
None
See application file for complete search history.

(56) References Cited

PUBLICATIONS

Raines et al. Annu Rev Biochem. 2009 ; 78: 929-958. doi:10.1146/annurev.biochem.77.032207.120833.*
Barrett, K. T. et al., *Nature* 2014, 509, 71.
Bartlett, G. J. et al., *Nat. Chem. Biol.* 2010, 6, 615.
Beck, K. et al., *Proc. Natl. Acad. Sci. USA*, 2000, 97, 4273.
Berisio, R. et al., *Protein Sci.* 2002, 11, 262.
Bowie, J. U. *Curr. Opin. Struc. Biol.* 2011, 21, 42.
Buevich, A. V. et al., *J. Biol. Chem.* 2004, 279, 46890-46895.
Byers, P. H. *Philos. Trans. R. Soc, B* 2001, 356, 151-157.
Cejas Ma et al., Proc Natl Acad Sci U S A. 2008, 105(25):8513-8.
Choudhary, A. et al., *J. Am. Chem. Soc.* 2009, 131, 7244.
Dunitz, J. D. *Chem. Biol.* 1995, 2, 709.
Fallas, J. A. et al.,. *J. Biol. Chem.* 2009, 284, 26851.
Fields, G. B. *Org. Biomol. Chem.* 2010, 8, 1237.
Fu, Y. W. et al., *J. Am. Chem. Soc.* 2006, 128, 15948.
Gao, J. et al., *Nat. Struct. Mol. Biol.* 2009, 16, 684.
Ghoroghchian et al., *P Natl Acad Sci USA*. 2005;102:2922-7.
He, M.; Bode, J. W. *Proc. Natl. Acad. Sci. USA* 2011, 108, 14752.
Horng, J. C. et al., *Protein Sci.* 2007, 16, 208.
Jakobsche, C. E. et al., *J. Am. Chem. Soc.* 2010, 132, 6651.
Kotch, F. W. et al., *J. Am. Chem. Soc.* 2008, 130, 2952.
Lehn JM. Proc Natl Acad Sci U S A. 2002;99(8):4763-8.
Mirsky, A. E.; Pauling, L. *Proc. Natl. Acad. Sci. USA* 1936, 22, 439.
Mizuno, K. et al., *Biophys. J.* 2010, 98, 3004.
Newberry, R. W. et al., *Protein Sci.* 2014, 23, 284.
Newberry, R. W. et al., *Chem. Commun.* 2015, 51, 9624.
Pauling, L. et al., *Proc. Natl. Acad. Sci. USA* 1951, 37, 205.
Pauling, L.; Corey, R. B. *Proc. Natl. Acad. Sci. USA* 1951, 37, 241.
Pauling, L.; Corey, R. B. *Proc. Natl. Acad. Sci. USA* 1951, 37, 729.
Schumacher, M. et al., *J. Mol. Biol.* 2005, 280, 20397.
Shoulders, M. D.; et al., *J. Am. Chem. Soc.* 2006, 128, 8112.
Shoulders, M. D. et al., *Bioorg. Med. Chem. Lett.* 2009, 19, 3859.
Shoulders, M. D.; Raines, R. T. *Annu. Rev. Biochem.* 2009, 78, 929.
Shoulders, M. D. et al., *Proc. Natl. Acad. Sci. USA* 2010, 107, 559.
Srinivasan, R.; Rose, G. D. *Proc. Natl. Acad. Sci. USA* 1999, 96, 14258.
Tuckwell, D. S. et al., *J. Cell Sci.*, 1994, 107, 993.
Zhang, Y.; et al., *Angew. Chem. Int. Ed.* 2015, 54, 10826.
Anfinsen, C. B. *Science* 1973, 181, 223.
Bella, J. et al., *Science* 1994, 266, 75.
Bella J, et al., *Structure*. 1995;3(9):893-906.
Benvin AL et al., J Am Chem Soc. 2007;129(7):2025-34.
Berg, R. A.; Prockop, D. J. *Biochem. Biophys. Res. Commun.*, 1973, 52, 115.
Bretscher, L. E. et al., *J. Am. Chem. Soc.* 2001, 123,777.
Cadamuro, S. A. et al., *Angew. Chem.* 2008, 120, 2174.
Cejas, M. A. et al., J. Am. Chem. Soc. 2007, 129, 2202.
Černý, J.; Hobza, P. *Phys. Chem. Chem. Phys.* 2007, 9, 5291.
Clayden, J.; Lund, A.; Vallverdú, L.; Helliwell, M. *Nature* 2004, 431, 966.
Chen, Y. S. et al., *Biopolymers* 2011, 96, 60.
Chou, P. Y.; Fasman, G. D. *J. Mol. Biol.* 1977, 115, 135.
Conlon P. et al., J Am Chem Soc. 2008;130(1):336-42.
Crick, F. H. C. *Nature* 1955, 176, 915.
Dai, N. et al., *J. Am. Chem. Soc.* 2008, 130, 5396.
Dai, N.; Etzkorn, F. A. *J. Am. Chem. Soc.* 2009, 131, 13728.
Deechongkit, S. et al., *Nature* 2004, 430, 101.
Eberhardt ES et al., J Am Chem Soc. 1996;118:12261-6.
Elemans Jaaw et al., Advanced Materials. 2006;18:1251-66.
Engel, J. et al., *Biopolymers* 1977, 16, 601.
Engel, J.; Bächinger, H. P. *Top. Curr. Chem.* 2005, 247, 7.
Erdmann, R. S.; Wennemers, H. *J. Am. Chem. Soc.* 2010, 132, 13957.
Erdmann, R. S.; Wennemers, H. *Angew. Chem. Int. Ed.* 2011, 50, 6835.
Erdmann, R. S.; Wennemers, H. *J. Am. Chem. Soc.* 2012, 134, 17117.
Fallas, J.A. et al., Chem. Soc. Rev., 2010, 39, 3510-3527.
Fields, G. B.; Prockop, D. J. *Biopolymers* 1996, 40, 345.
Foster S. et al., Macromolecules. 2009;42:2023-30.
Frey, P.; Nitschmann, H. *Helv. Chim. Acta.* 1976, 59, 1401.
Frischmann PD, Chemical Society reviews. 2013;42:1847-70.
Fron E. et al., Chemphyschem. 2011;12(3):595-608.
Gauba, V.; Hartgerink, J. D. *J. Am. Chem. Soc.* 2007, 129, 2683.
Gauba, V.; Hartgerink, J. D. *J. Am. Chem. Soc.* 2007, 129, 15034.
Gonzalez-Rodriuguez D, Schenning Aphj. Chem Mater. 2011;23:310-25.
Goodman, M. et al., *J. Am. Chem. Soc.* 1996, 118, 10928.
Goodman, M. et al., *Biopolymers* 1998, 47, 127.

(Continued)

*Primary Examiner* — Jeanette M Lieb
(74) *Attorney, Agent, or Firm* — Morgan, Lewis & Bockius LLP; Robin M. Silva

(57) ABSTRACT

The invention relates to aza-amino acid backbone-modified biomimetic collagens and general methods for designing and making biomimetic materials and molecular mimics.

15 Claims, 37 Drawing Sheets

(56) References Cited

PUBLICATIONS

Görl D et al., Angewandte Chemie (International ed in English). 2012;51:6328-48.
Haase M. et al., Phys Chem Chem Phys. 2011;13(5):1776-85.
Hodges, J. A.; Raines, R. T. *J. Am. Chem. Soc.* 2003, 125, 9262.
Holmgren, S. K. et al., *Nature* 1998, 392, 666.
Inouye, K. *Arch. Biochem. Biophys.*, 1982, 219, 198.
Jalan AA, Hartgerink JD. Current opinion in chemical biology. 2013;17(6):960-7.
Janssen PG, et al., J Am Chem Soc. 2007;129:6078-9.
Jenkins, C. L. et al., *J. Am. Chem. Soc.* 2003, 125, 6422.
Jenkins, C. L. et al., *Org. Lett.* 2005, 7, 2619.
Jiang, T. et al., *Angew. Chem. Int. Ed.* 2014, 53, 8367.
Kalluri, R. *Nat. Rev. Cancer*, 2003, 3, 422.
Kawahara, K. et al.,. *Biochemistry* 2005, 44, 15812-22.
Kramer RZ et al., J Mol Biol. 1998;280(4):623-38.
Kusebauch, U. et al., *Angew. Chem. Int. Ed.* 2006, 45, 7015.
Lauer-Fields, J. L. et al., *Biopolymers*, 2002, 66, 19.
Lavis LD, Raines RT. ACS chemical biology. 2008;3(3):142-55.
Lee, S.-G.; Lee, J. Y.; Chmielewski, *J. Angew. Chem. Int. Ed.* 2008, 47, 8429.
Lee J, Chmielewski J. Chem Biol Drug Des. 2010;75(2):161-8.
Lecoq A. et al., Biopolymers. 1993;33(7):1051-9.
Lehn JM. Science. 1985;227(4689):849-56.
Lehn JM. Supramolecular chemistry. Science. 1993;260(5115):1762-3.
Lehn JM, Curr Chem. 2012;322:1-32.
Li S-L et al., Chemical Society reviews. 2012;41:5950-68.
Malinovskii VL et al., Chemical Society reviews. 2010;39:410-22.
Myllyharju, J.; Kivirikko, K. I. *Trends Genet.* 2004, 20, 33-43.
Okuyama K. Connective tissue research. 2008;49(5):299-310.
Okuyama K, et al., J Mol Biol. 1981, 152(2):427-43.
O'Leary LE, et al. Nature chemistry. 2011;3(10):821-8.
Pace, C. N. *Nat. Struct. Mol. Biol.* 2009, 16, 681.
Pauling, L.; Corey, R. B. *Nature*, 1951, 168, 550.
Pedersen, S. W. et al., *Nat. Commun.* 2014, 5, 3215.
Perez CM, et al., Chem Commun (Camb). 2014;50(60):8174-6.
Persikov, A. V. et al., *Biochemistry*, 2000, 39, 14940.
Pires MM et al., Langmuir. 2012;28(4):1993-7.
Proulx, C. et al., *Chem Med. Chem.*, 2011, 3, 1139.
Przybyla, D. E.; Chmielewski, J. *J. Am. Chem. Soc.* 2008, 130, 12610.
Przybyla DE, Chmielewski J. Biochemistry-Us. 2010;49(21):4411-9.
Przybyla DE, J Am Chem Soc. 2013;135(9):3418-22.
Ramachandran, G. N.; Kartha, G. *Nature* 1954, 174, 269.
Ramachandran GN, Kartha G. Nature. 1955;176(4482):593-5.
Ramshaw et al., *J. Struc. Biol.* 1998, 122, 86-91.
Rele, S. et al.,. *J. Am. Chem. Soc.* 2007, 129, 14780.
Rich, A.; Crick, F. H. *J. Mol. Biol.* 1961, 3, 483.
Ricard-Blum, S. et al., *Top. Curr. Chem.* 2005, 247, 35.
Rybtchinski B,. J Am Chem Soc. 2004;126:12268-9.
Sabatino, D. et al., *Org. Lett.* 2009, 11, 3650.
Schmidt-Mende et al., Science 2001;293:1119-22.
Schneider, H. -J. *Angew. Chem. Int. Ed.* 2009, 48, 3924.
Shah, N. K. et al., *Biopolymers* 1999, 49, 297-302.
Siebler, C. et al., *Angew. Chem. Int. Ed.* 2014, 53, 10340.
Suzuki, E. et al., *Int. J. Biol. Macromol.*, 1980, 2, 54.
Szent-Gyorgyi C. et al., J Am Chem Soc. 2010;132:11103-9.
Teo YN, Kool ET. DNA-multichromophore systems. Chemical reviews. 2012;112:4221-45.
Umashankara, M. et al., *Chem. Commun.* 2003, 2606.
Van Goor H. et al., Analytical and quantitative cytology and histology / the International Academy of Cytology [and] American Society of Cytology. 2001;23(5):345-54.
Wang, J.; Feringa, B. L. *Science* 2011, 331, 1429.
Wang, A. Y. et al., *J. Am. Chem. Soc.* 2005, 127, 4130.
Watson, J. D.; Crick, F. H. C. *Nature* 1953, 171, 737.
Wasielewski MR. Accounts of chemical research. 2009;42:1910-21.
Weil T, et al., Angew Chem Int Ed Engl. 2010;49(48):9068-93.
Weil T. et al., Biomacromolecules. 2005;6(1):68-79.
Weil T. et al., Chemistry. 2004;10(6):1398-414.
Whitesides GM. Molecular recognition in water. Abstr Pap Am Chem S. 2013.
Whitesides GM, Mathias JP, Seto CT. Science. 1991;254(5036):1312-9.
Williams, D. H. et al., *Angew. Chem. Int. Ed.* 2004, 43, 6596.
Yashima E. et al., Chemical reviews. 2009;109:6102-211.
Yamazaki, C. M. et al., *Biopolymers* 2008, 90, 816.
Yuan Z et al., Chemistry. 2013, 19(36):11842-6.
Zega, A. Cur. Med. Chem. 2005, 12, 589.

\* cited by examiner

Figure 4

CMP-14
Identified as a collagenase inhibitor

A = B = OP-azGOP-azGOP-azGOP-azG

Common core for use with diverse C strands
containing protein binding sequences

Specific protein targeting sequences for C peptide:

Collagenase: OP-azGOP-azGOP-azGOP-azG

MMP-1: azGPQazGLAazGQRazGIVazGLP

HSP47: xazGxRazG

VWF: RazGQOazGVMazGF and
azGPRazGQOazGVMazGFO

DDR2: azGVMazGFO

SPARC: azGPOazGPSazGPRazGQOazG-
VMazGFOazGPKazGNDazGAO

(16) (Pro-Hyp-Gly)₃-Pro-Arg-Gly-(Pro-Hyp-Gly)₄-NH₂

(17) (Pro-Hyp-Gly)₃-(Pro-Arg-azGly)-(Pro-Hyp-Gly)₄-NH₂

Figure 6
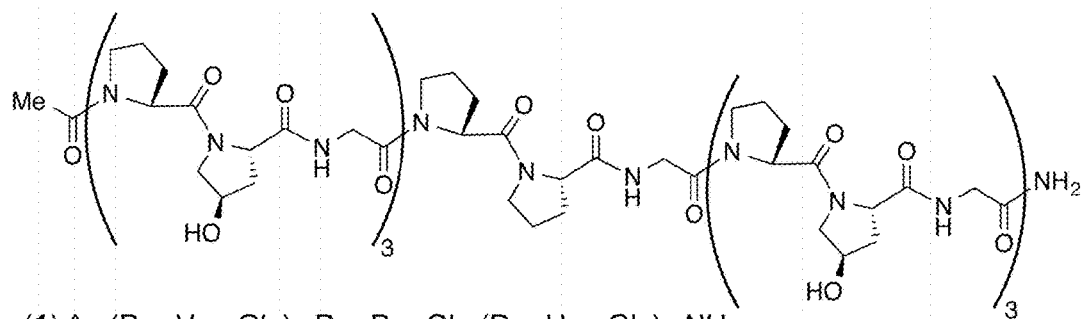
(1) Ac-(Pro-Hyp-Gly)₃-Pro-Pro-Gly-(Pro-Hyp-Gly)₃-NH₂
(2) Ac-(Pro-Hyp-Gly)₃-Pro-Hyp-Gly-(Pro-Hyp-Gly)₃-NH₂
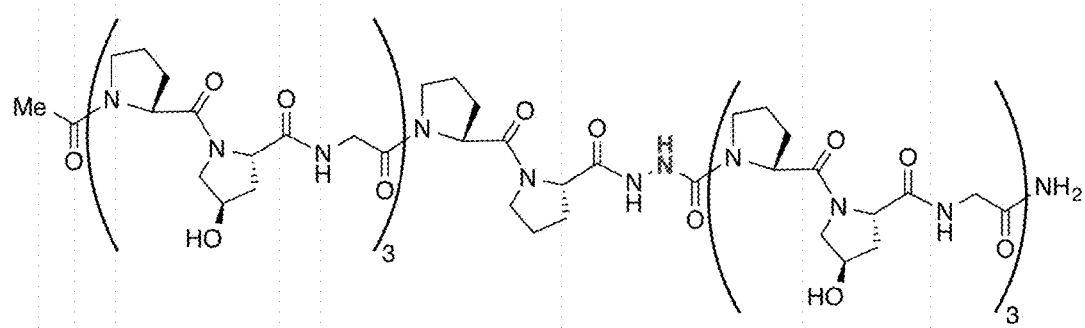
(3) Ac-(Pro-Hyp-Gly)₃-Pro-Pro-azGly-(Pro-Hyp-Gly)₃-NH₂
(4) Ac-(Pro-Hyp-Gly)₃-(Pro-Hyp-azGly)-(Pro-Hyp-Gly)₃-NH₂

Figure 7A – Figure 7E a)

| peptide | central triplet | Tm (°C) 12 °C/h | Tm (°C) 36 °C/h | ΔG (kcal mol⁻¹) | folding t$_{1/2}$ (min) |
|---|---|---|---|---|---|
| 1 | -Pro-Pro-Gly- | 37 | 41 | -11 | 33 ± 2 |
| 2 | -Pro-Hyp-Gly- | 40 | 44 | -12 | 24 ± 6 |
| 3 | -Pro-Pro-azGly- | 47 | 51 | -13 | 27 ± 6 |
| 4 | -Pro-Hyp-azGly- | 51 | 55 | -15 | 14 ± 3 |

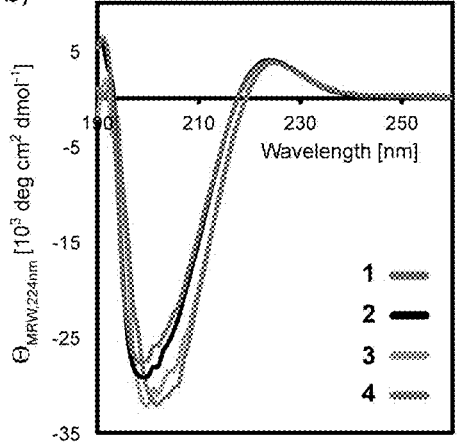

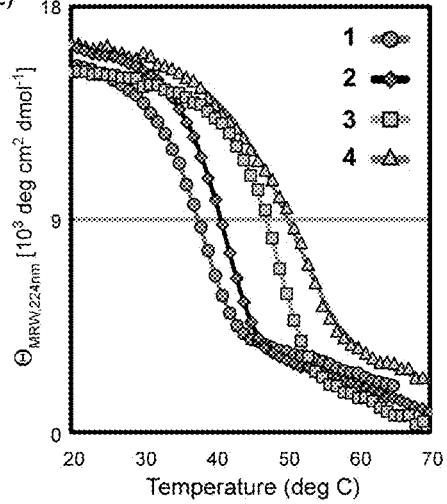

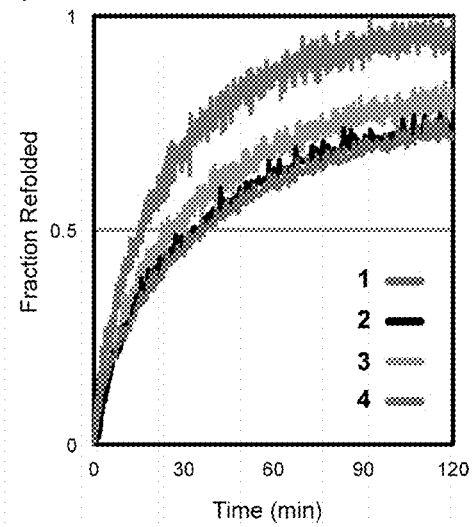

e) SEC-MALS

| peptide | avg. MW & range (kDa) | oligomeric state |
|---|---|---|
| 1 | 5.4 / 5.2-5.4 | trimer |
| 2 | 5.6 / 5.7-5.8 | trimer |
| 3 | 5.8 / 5.6-5.8 | trimer‡ |
| 4 | 5.6 / 5.5-5.7 | trimer‡ |
| *5 | 1.9 / 1.7-2.0 | monomer |

*Peptide 5 contains a D-proline residue at the central triplet (-DPro-Pro-Gly-) and serves as a monomeric standard.
‡Presence of trimeric species also verified by sedimentation equilibrium analysis.

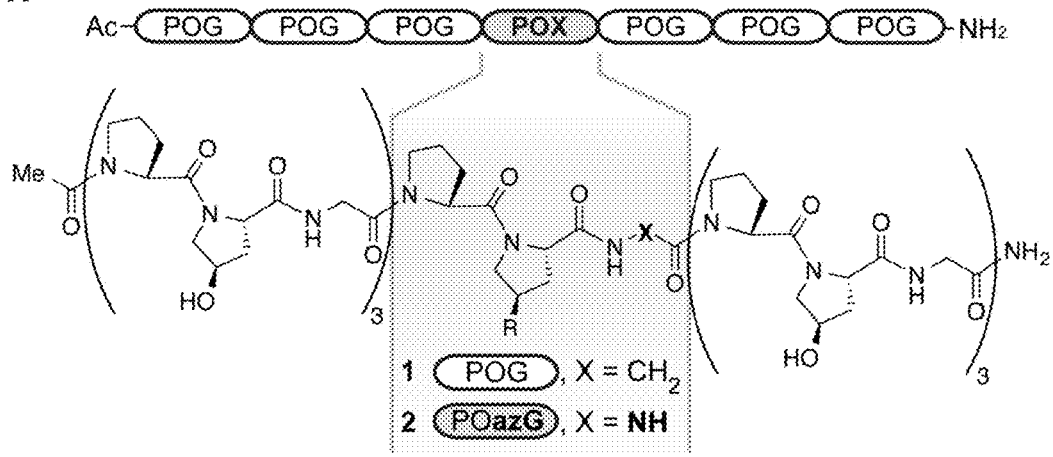

B

| CMP | CMP sequence | $T_m$ / C |
|---|---|---|
| 1 | Ac-(POG)(POG)(POG)(POG)(POG)(POG)(POG)-NH₂ | 40 |
| 3 | Ac-(POazG)(POG)(POG)(POG)(POG)(POG)(POG)-NH₂ | 46 |
| 4 | Ac-(POG)(POazG)(POG)(POG)(POG)(POG)(POG)-NH₂ | 48 |
| 5 | Ac-(POG)(POG)(POazG)(POG)(POG)(POG)(POG)-NH₂ | 50 |
| 2 | Ac-(POG)(POG)(POG)(POazG)(POG)(POG)(POG)-NH₂ | 51 |
| 6 | Ac-(POG)(POG)(POG)(POG)(POazG)(POG)(POG)-NH₂ | 49 |
| 7 | Ac-(POG)(POG)(POG)(POG)(POG)(POazG)(POG)-NH₂ | 46 |

| CMP | CMP sequence | $T_m$ / C |
|---|---|---|
| 8 | Ac-(POG)(POazG)(POG)(POG)(POG)(POazG)(POG)-NH₂ | 57 |
| 9 | Ac-(POG)(POG)(POazG)(POG)(POazG)(POG)(POG)-NH₂ | 59 |
| 10 | Ac-(POG)(POG)(POG)(POazG)(POazG)(POG)(POG)-NH₂ | 61 |
| 11 | Ac-(POG)(POazG)(POG)(POazG)(POG)(POazG)(POG)-NH₂ | 69 |
| 12 | Ac-(POG)(POG)(POazG)(POazG)(POazG)(POG)(POG)-NH₂ | 74 |

| CMP | CMP sequence | $T_m$ / C |
|---|---|---|
| 13 | Ac-(azG)(POazG)(POazG)(PO)-NH₂ | — |
| 14 | Ac-(azG)(POazG)(POazG)(POazG)(PO)-NH₂ | 36 |
| 15 | Ac-(azG)(POazG)(POazG)(POazG)(POazG)(PO)-NH₂ | 78 |

Figure 15

Ac-(POG)(POG)(POG)(XYG)(POG)(POG)(POG)-NH₂

Probing the central triplet position of collagen using single atom substitutions

| Peptide | central triplet | Tm (°C) 12 °C/h | ΔG (kcal mol⁻¹) | folding t₁/₂ (min) |
|---|---|---|---|---|
| 1* | (PPG) | 36.7 ± 0.4 | -10.5 | 33 ± 2 |
| 3* | (AzPPG) | 36.0 ± 0.5 | -7.7 | 217 ± 3 |
| 4 | (PAzPG) | — | — | — |
| 2 | (POG) | 39.9 ± 0.5 | -12.0 | 24 ± 6 |
| 5 | (AzPOG) | 39.0 ± 0.3 | -9.6 | 53 ± 9 |

Key: P = proline, O = hydroxyproline, G = glycine, AzP = aza-proline
* Results from peptides 1 and 3 reported in reference #.

Figure 18

| Peptide | Peptide sequence | Folding |
|---|---|---|
| 11 | Ac-(POG)(POG)(●●●OG)(POG)(●●●OG)(POG)(POG)-NH₂ | no helix |
| 12 | Ac-(POG)(●●●OG)(POG)(POG)(POG)(●●●OG)(POG)-NH₂ | no helix |
| 13 | Ac-(POG)(POG)(●●●OG)(●●●OG)(●●●OG)(POG)(POG)-NH₂ | no helix |

Figure 19
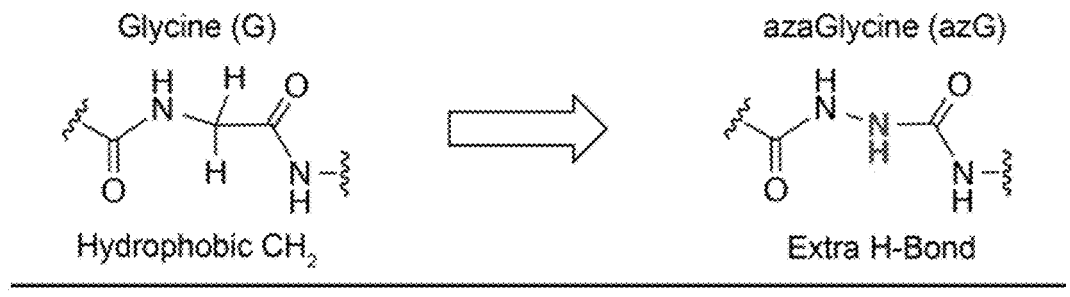
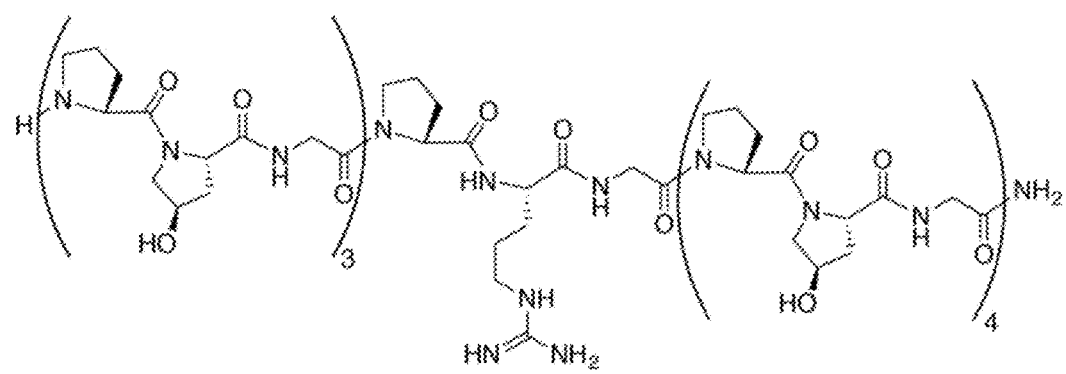
(1) (Pro-Hyp-Gly)₃-Pro-Arg-Gly-(Pro-Hyp-Gly)₄-NH₂
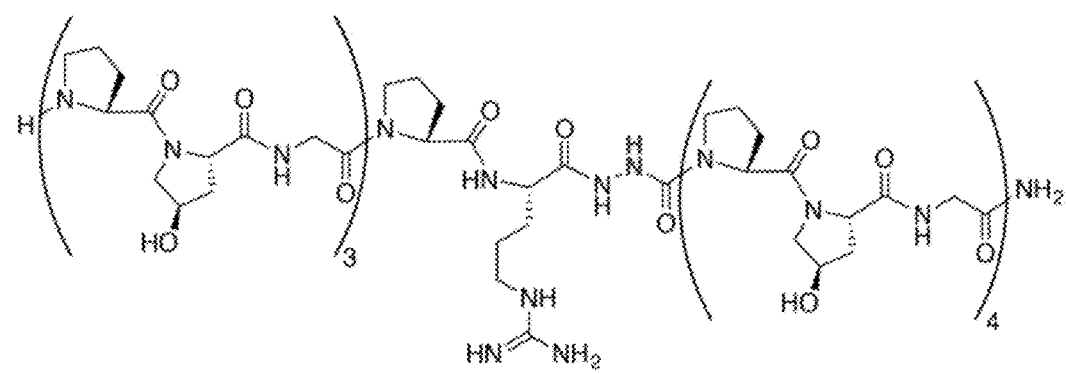
(2) (Pro-Hyp-Gly)₃-(Pro-Arg-azGly)-(Pro-Hyp-Gly)₄-NH₂

A)

B)

Figure 25A – Figure 25C
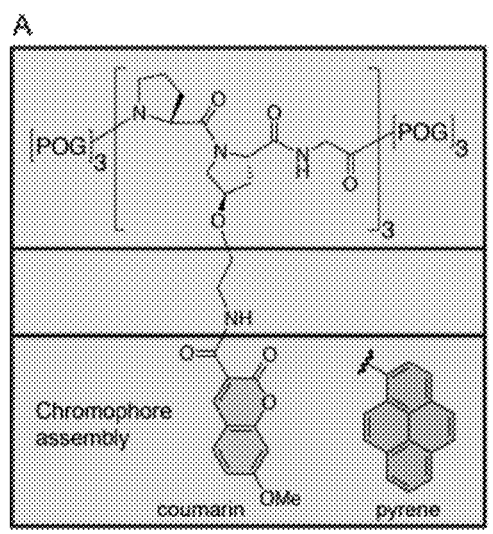
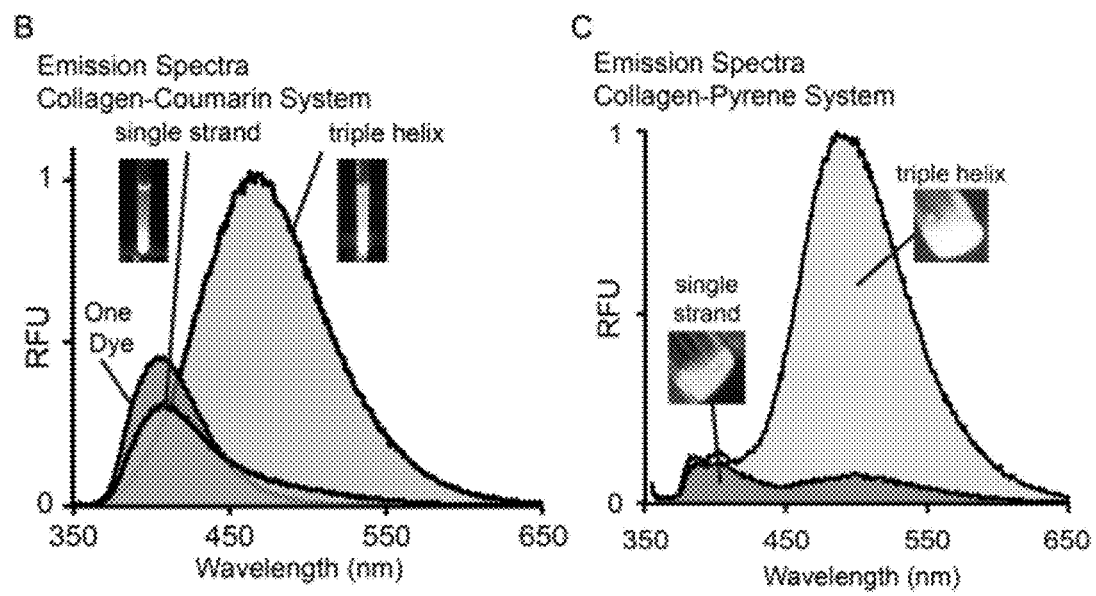

X = acetyl, others

Y = amino, others

Figure 27

New peptides with single aza-glycine residues:

Ac-POazG-POG-POG-POG-POG-POG-POG-NH2

Ac-POG-POazG-POG-POG-POG-POG-POG-NH2

Ac-POG-POG-POazG-POG-POG-POG-POG-NH2

Ac-POG-POG-POG-POG-POazG-POG-POG-NH2

Ac-POG-POG-POG-POG-POG-POazG-POG-NH2

New peptides with multiple aza-glycine residues:

Ac-POG-POG-POG-POazG-POazG-POG-POG-NH2

Ac-POG-POG-POazG-POG-POazG-POG-POG-NH2

Ac-POG-POG-POazG-POazG-POazG-POG-POG-NH2

Ac-POG-POazG-POG-POG-POG-POazG-POG-NH2

Ac-POG-POazG-POG-POazG-POG-POazG-POG-NH2

100 U/ml: control peptide (POG)$_7$ was completely digested within 10 minutes;

1 U/ml: digestion of control peptide (POG)$_7$ was too slow to be observed;

10 U/ml: Collagenase background CD signal was minimized while maintaining a good catalytic turnover.

AZA-AMINO ACID COLLAGEN COMPOUNDS

CROSS REFERENCE TO RELATED APPLICATIONS

This application claims the benefit under 35 U.S.C. § 119(e) of U.S. Provisional Application No. 62/329,069 filed on Apr. 28, 2016 which is incorporated herein by reference in its entirety for all purposes.

BACKGROUND OF THE INVENTION

Collagen is the main structural protein in the extracellular space of connective tissues of animal bodies and is the single most abundant protein in the animal kingdom. It is also one of the most useful biomaterials with numerous known applications in the medical, dental, and pharmacological fields. For example, collagen can be prepared as cross-linked, compacted solids or as lattice-like gels. They have been used as wound dressing, drug delivery systems, and sponges, just to name a few. Because of its versatility, naturally occurring collagen has been a source of inspiration for biomimetic designs to extend the range of its usefulness. Over the past several decades, intense research efforts had aimed at developing a molecular level understanding of collagen's self-assembly properties to further the development of designed materials with superior properties.

Naturally occurring collagen is a supramolecular complex made up of three collagen polypeptides. Historically, a great deal of our understanding about molecular and supramolecular structures came from speculative model building by pioneers such as Pauling, Watson, and Crick. One guiding principle for these pioneering model building is the maximization or correct pairing of inter- and intra-chain hydrogen bonds in biopolymers. Biomolecular structures are governed by a delicate balance of non-covalent intra- and intermolecular interactions, and hydrogen bonding is one of the most ubiquitous non-covalent interactions in nature. Together, these interactions drive macromolecular assembly and intermolecular recognition events that are critical to all life processes.

In the case of collagen, the triple helix is often composed of two identical polypeptide chains (α1) and an additional polypeptide chain (α2) that differs slightly in its chemical composition. Each of the three polypeptide chains adopts a left-handed helix conformation. When the three strands are mixed together, they can self-assemble into a right-handed triple helix depending on length and sequence of the polypeptide chain. In biological systems the production of collagen is more complex, involving translation of a pre-pro-peptide, N-terminal processing of the pre-pro peptide to pro-collagen in the endoplasmic reticulim, extensive post-translational processing of the amino acid sidechains followed by glycosylation with monosaccharides, transport to the Golgi apparatus for modification with oligosaccharides and eventual packaging into secretory vesicles that are transported to the extracellular environment where further processing of procollagen leads to tropocollagen in certain forms. Further extracellular oxidation and various modifications eventually lead to the formation of collagen fibrils. In nearly all naturally occurring collagen peptides, every third residue is a glycine. Mutations in the strictly conserved glycine form the molecular basis for many debilitating human diseases such as osteogenesis imperfecta. The periodic spacing of the glycine residue at every third amino acid position in conjunction with the one residue stagger allows for a tightly packed triple helix with a repeating cross-strand hydrogen bond network. In other words, collagen peptides most often have a repeating C-(XaaYaaGly)$_n$-N motif, with exceptions often leading to a number of human diseases. The most common amino acids in the variable Xaa and Yaa positions are (2S)-proline (Pro, 28%) and (2S,4R)-4-hydroxyproline (Hyp, 38%) although the Xaa and Yaa positions can vary dramatically with any amino acid occupying either position. Alternate amino acid sequences, where Xaa and Yaa are not Pro or Hyp can represent recognition domains for important protein-collagen interactions such as those with integrins and matrix remodeling enzymes (matrix metalloprotein 1, cathepsin K, and von Willibrand factor to name a few) involved in normal homeostasis and human disease states (cancer biology, genetic disease, various musculoskeletal disease, etc.). One of the most common triplet amino acid sequences in collagen is ProHypGly (10.5%).

Given that collagen is made up of three polypeptide chains, design of collagen mimetic material can theoretically be achieved by side-chain modification or backbone modification. Prior efforts to create biomimetic collagen have found that side-chain modification was a successful approach, but limiting as far as preserving the overall natural surface features and topology of collagen. When collagen peptides are modified with unnatural amino acid side-chain residues, they generally are able to retain the ability to self-assemble into triple helices although sometimes with decreased stability depending on the modification. It was observed that the stability of the triple helix depends on a delicate balance of noncovalent interactions, hence, side-chain modifications had the effect of modulating the stability of the triple-helical structure although this often necessitates changes to the structure that result in dramatically different surface features that could be limiting in terms of recognition interactions with biologically relevant environments and biomacromolecules involved in protein-collagen interactions.

In contrast, efforts to modify collagen backbone had been largely unsuccessful, with the limited exception of a peptoid residue developed by Goodman and co-workers, although this could be considered a form of side chain addition.[1] In particular, the strictly conserved glycine residue in collagen peptides has remained largely intolerant to substitution, barring a recent thioamide substitution by Raines and coworkers.[2]

Numerous attempts to modify the collagen backbone had been tried, including stereochemical inversion, heteroatom replacement, and homologation, all of which resulted in either severe destabilization or a complete lack of triple helix formation in collagen model peptide systems. Raines and Miller demonstrated that substituting the glycine amide into either an ester or a trans alkene greatly destabilized the triple helical structure.[3] More recently, Etzkorn et al. demonstrated that substitution of any amide bond with (E)-alkene, regardless of whether it is involved in interchain hydrogen bonding, prevents formation of the triple helix even though the trans alkene locks the pseudo amide bond in the trans conformation.[4] Backbone modifications in the form of stereochemical inversion (L to D amino acids) and heteroatom replacement have all resulted in either severe destabilization or a complete lack of triple helix formation.[5] Amide-to-ester substitutions have a detrimental effect on collagen triple helix stability and many other protein secondary structures. In addition, trans alkene amide bond isosteres greatly destabilize the triple helical structure of collagen irrespective of positioning and involvement in hydrogen bonding. To date, these efforts have demonstrated a general intolerance of the collagen peptide backbone for molecular editing.

Despite these hurdles, discovering stabilizing backbone substitutions would provide significant opportunities for extending the properties and functions of biomimetic collagen. For example, there may be times when side-chain modification is not desirable and backbone modification is the only route to achieve designed material. The ability to stabilize the collagen peptide triple helical structure at the core while preserving the surface features of the natural amino acids opens the possibility for materials that interact with natural proteins in a way that perfectly mimics natural protein-collagen interactions. Other potential applications may include self-assembly of shorter collagen peptides into stable triple helical assemblies that could be used as multivalent scaffolds in applications ranging from high-payload drug carriers to organized multichromophore assemblies for light harvesting and photonic materials applications as well as protein-protein interactions (PPIs) and collagen miniproteins that could have therapeutic potential.

Protein-protein interactions (PPIs) are involved in nearly all biological processes, including cell proliferation, growth, differentiation, and apoptosis. Stringent regulation of these biomolecular interfaces is essential for cellular function, making them attractive targets for the development of new therapeutics and biological probes. While a number of strategies have been applied to modulate these interfacial interactions including miniature proteins and peptidomimetics, this is extremely challenging due to the lack of natural partners and the high level of adaptability of protein-protein binding sites. It is also difficult to target PPIs because their interfacial surfaces are very large, shallow, flat, and often do not have well-defined pockets, unlike many enzymes. The secondary structure at the interface of PPIs (often characterized by α-helices or other common secondary structure motifs) has been the focus for rational design approaches. The most accurate way to mimic these α-helical interfaces is to use peptides consisting of α-amino acids (α-peptides). Hydrocarbon staples, hydrogen bond surrogates (HBS), β-peptides, miniature proteins, peptoids, and many other scaffolds have been successful in improving the stability and bioavailability of these peptides. Similar to protein-protein interactions that involve α-helix recognition, there are a multitude of interactions involving collagen triple-helix recognition (FIG. 1). Notably, wound repair is characterized by dynamic reciprocity, defined as ongoing, bidirectional interactions between cells and their surrounding microenvironment (particularly the extracellular matrix (ECM)). Thus, identification of key matrix components and mechanisms that direct dynamic reciprocity to promote a regenerative healing response will aid in the development of novel therapeutics for a range of maladies including cancer fibrosis, diabetes, and neurodegenerative disease.

Moreover, there is no general way to modulate collagen-protein interactions and much of the fundamental biomolecular recognition details are still unknown. Specifically, to the best of our knowledge, no interactions between heterotrimeric collagen triple helices and proteins have yet been characterized, although recent advances in synthetic peptide chemistry have helped to work toward this goal. This gap in knowledge exists because of a lack of chemical tools and due to the complex nature of collagen. Specifically, to the best of our knowledge, no interactions between heterotrimeric collagen triple helices and proteins have yet been characterized. This gap in knowledge exists because of a lack of chemical tools and due to the complex nature of collagen.

Many of the primary hurdles in collagen peptide design arise from difficulties in obtaining short, stable collagen mimetic peptides. Longer peptides are inherently more complex, expensive, and time-intensive to synthesize, while shorter collagen peptides suffer from the inability to self-assemble into the triple helical form at reasonable temperatures (25-37° C.). The complex purification and sterilization processes involved in deriving collagen peptides from animal sources can also generate low yields and diminish the mechanical and chemical functionality of the peptide in addition to the problem of separation from a complex heterogeneous mixture. Simple, precisely defined, collagen peptides that retain the capacity to self-assemble into triple helical structures and higher order materials would open the door for the design of new classes of chemical probes and potential therapeutics such as next generation wound healing agents for example. In addition to potential therapeutic applications there are a vast number of fundamental applications for modulating the collagen-protein interactome.

Therefore, there exists a need for backbone-modified biomimetic collagens and general methods for designing and making biomimetic materials and molecular mimics as well as a need to develop new classes of protein-protein interaction (PPI) modulators to broadly target collagen-protein interfaces by mimicking the triple-helix.

BRIEF SUMMARY OF THE INVENTION

Accordingly, the present invention provides backbone-modified biomimetic collagens and general methods for designing and making biomimetic materials and molecular mimics. In one aspect, the present invention provides a composition comprising a first collagen monomer comprising at least seven amino acid triplets, wherein one of said triplets comprises an aza-glycine residue.

In another aspect, the present invention provides a composition comprising a first collagen monomer comprising at least seven amino acid triplets, wherein one of said triplets comprises an aza-proline residue.

In some embodiments, said monomer is 21 amino acids in length (21mer). In some embodiments, said aza-glycine is in the center triplet of said 21mer. In some embodiments, said aza-proline is in the center triplet of said 21mer. In some embodiments, said aza-glycine is at a terminus of said monomer. In some embodiments, said aza-proline is at a terminus of said monomer.

In another aspect, the present invention further comprises a second aza-glycine. In another aspect, the present invention further comprises a second aza-proline.

In another aspect, the present invention further comprises a second collagen monomer comprising at least seven amino acid triplets, wherein one of said triplets comprises an aza-glycine residue and a third collagen monomer comprising at least seven amino acid triplets, wherein one of said triplets comprises an aza-glycine residue.

In another aspect, the present invention further comprises a second collagen monomer comprising at least seven amino acid triplets, wherein one of said triplets comprises an aza-proline residue and a third collagen monomer comprising at least seven amino acid triplets, wherein one of said triplets comprises an aza-proline residue. In some embodiments, each of said monomers is 21 amino acids in length (21mer). In some embodiments, each of said aza-glycines is in the center triplet of each of said 21mers. In some embodiments, each of said aza-proline is in the center triplet of each of said 21mers.

In another aspect, the present invention provides a composition comprising a collagen monomer having the formula:

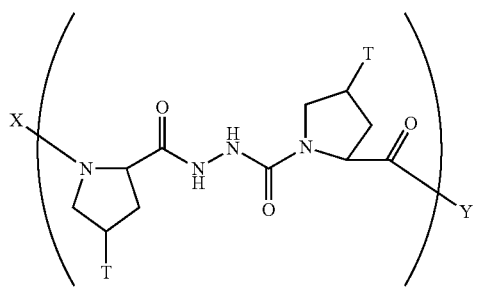

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

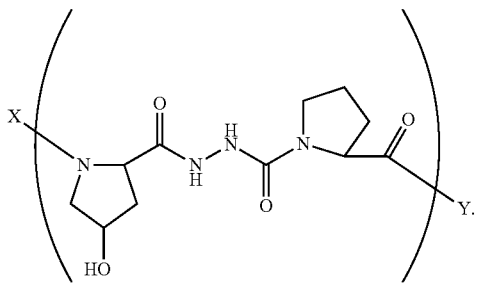

In some embodiments, said formula is:

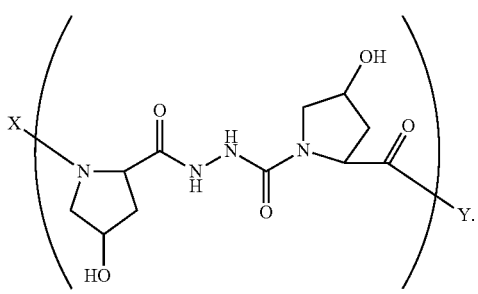

In some embodiments, said formula is:

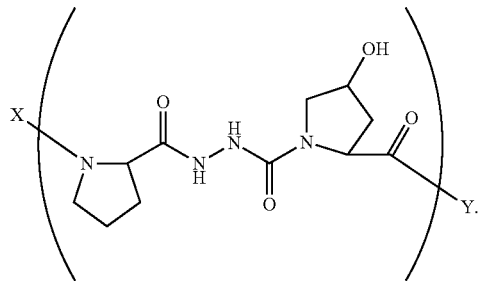

In some embodiments, said formula is:

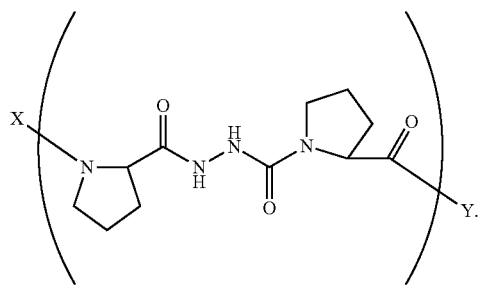

In another aspect, the present invention provides a composition comprising a collagen monomer having the formula:

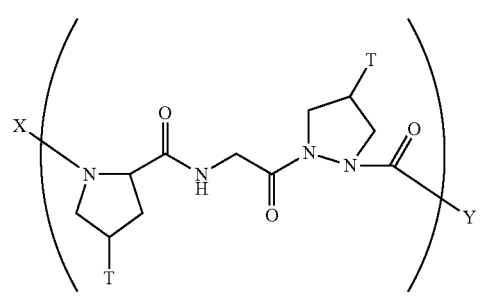

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

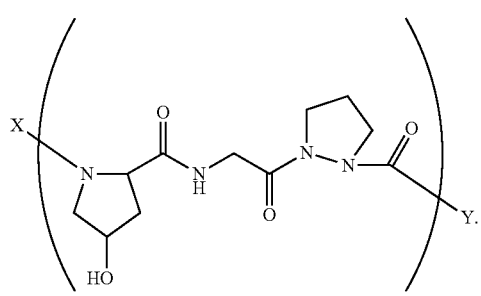

In some embodiments, said formula is:

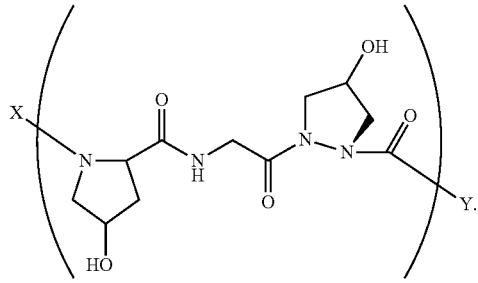

In some embodiments, said formula is:

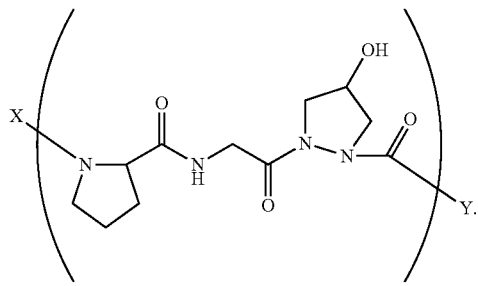

In some embodiments, said formula is:

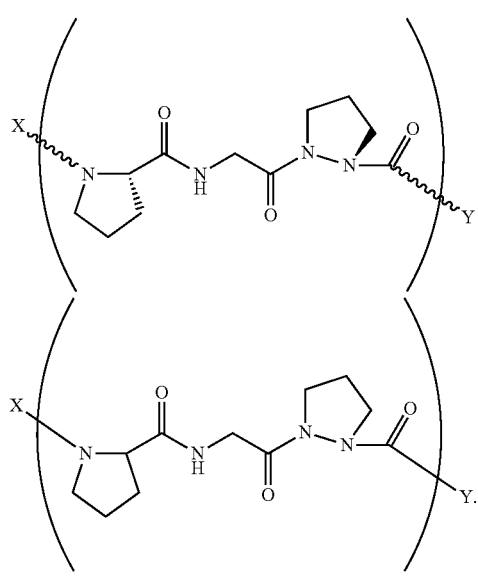

In another aspect, the present invention provides a composition comprising a collagen monomer having the formula:

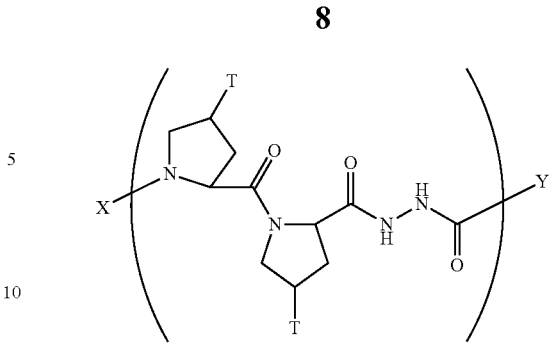

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

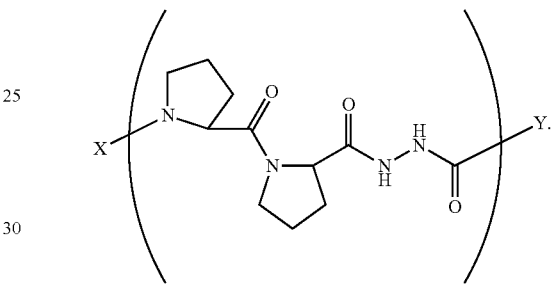

In some embodiments, said formula is:

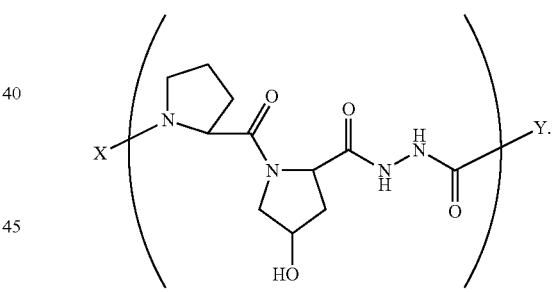

In some embodiments, said formula is:

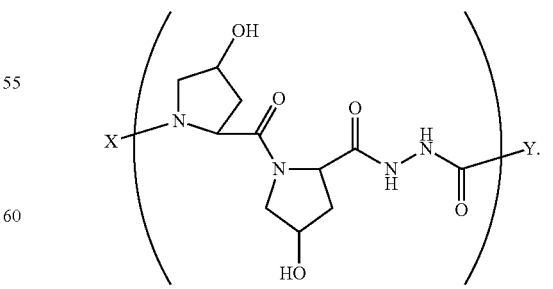

In another aspect, the present invention provides a composition comprising a collagen monomer having the formula:

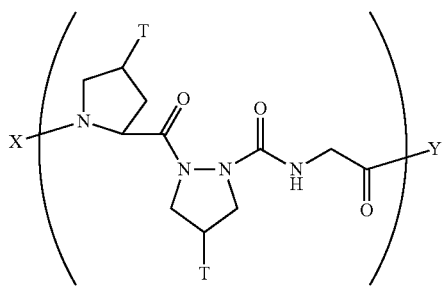

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

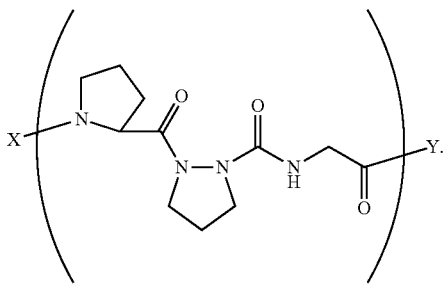

In some embodiments, said formula is:

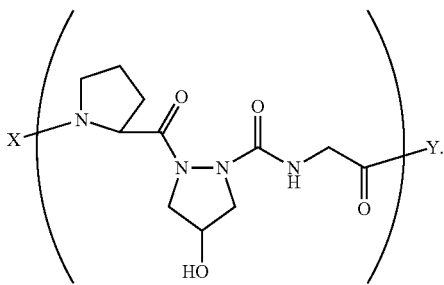

In some embodiments, said formula is:

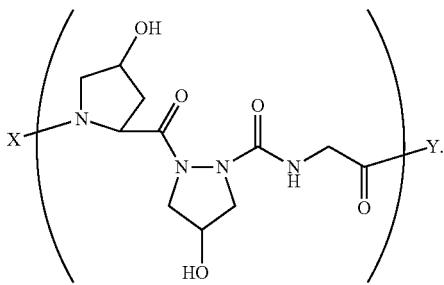

In another aspect, the present invention provides a composition comprising a collagen monomer having the formula:

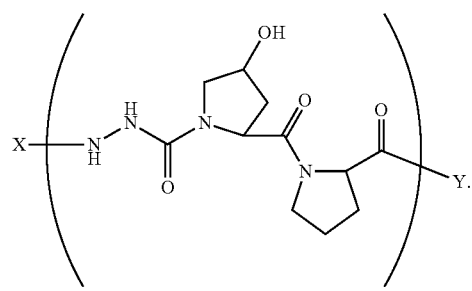

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

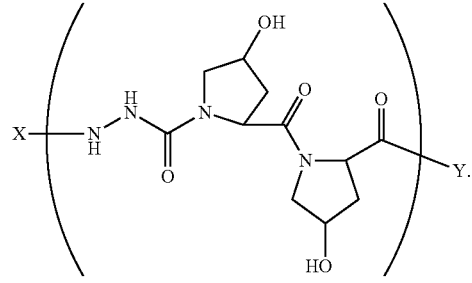

In some embodiments, said formula is:

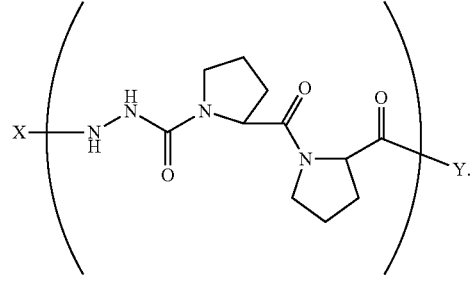

In some embodiments, said formula is:

In some embodiments, said formula is:

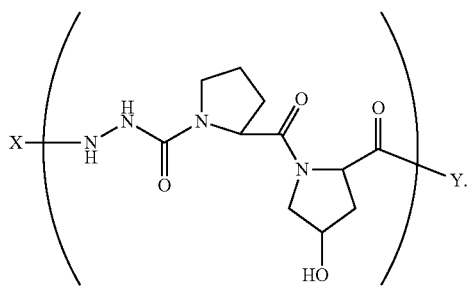

In another aspect, the present invention provides a composition comprising a collagen monomer having the formula:

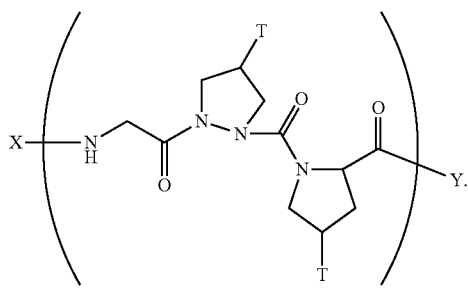

wherein X is selected from the group consisting of $(AA_3)_n$, an AA, $(AA)_2$, acetyl; Y is selected from the group consisting of $(AA_3)_m$, an AA, $(AA)_2$, amino; n is an integer from 1 to 50; m is an integer from 1 to 50; T is independently selected from —OH and —H. In some embodiments, said formula is:

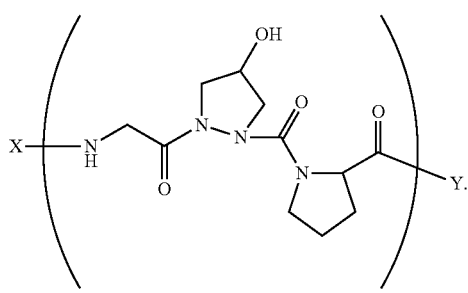

In some embodiments, said formula is:

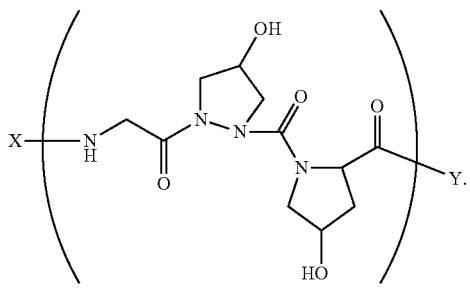

In some embodiments, said formula is:

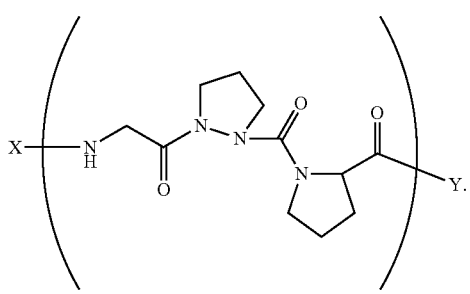

In some embodiments, said formula is:

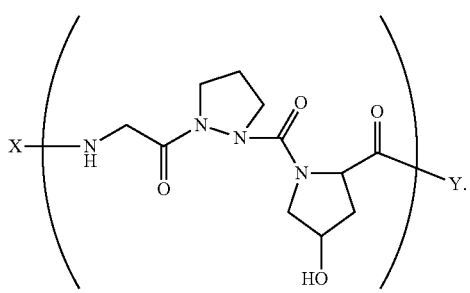

In another aspect, the present invention provides a composition comprising a peptide having the formula:

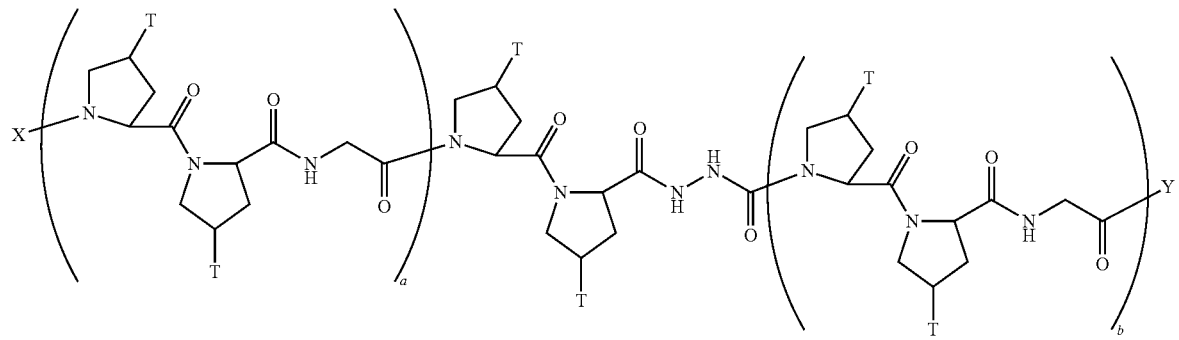

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition comprising a peptide having the formula:

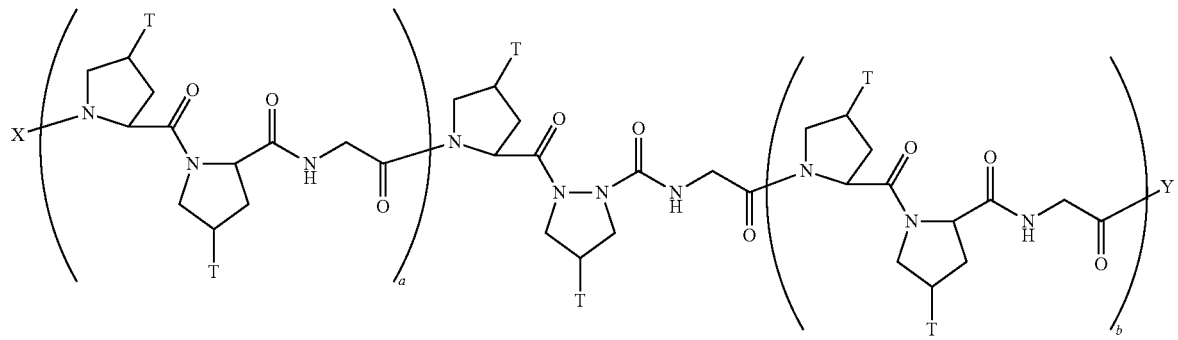

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition comprising a peptide having the formula:

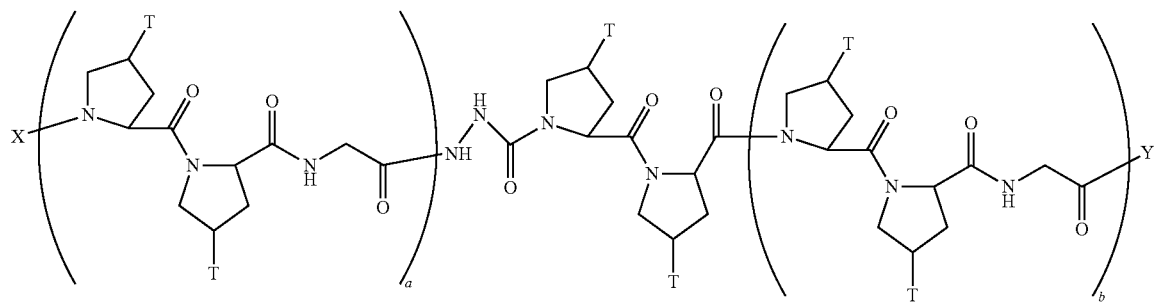

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition comprising a peptide having the formula:

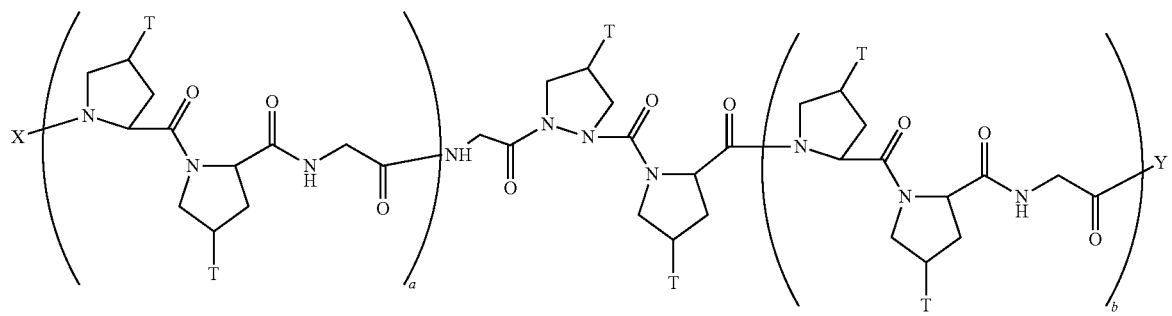

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition comprising a peptide having the formula:

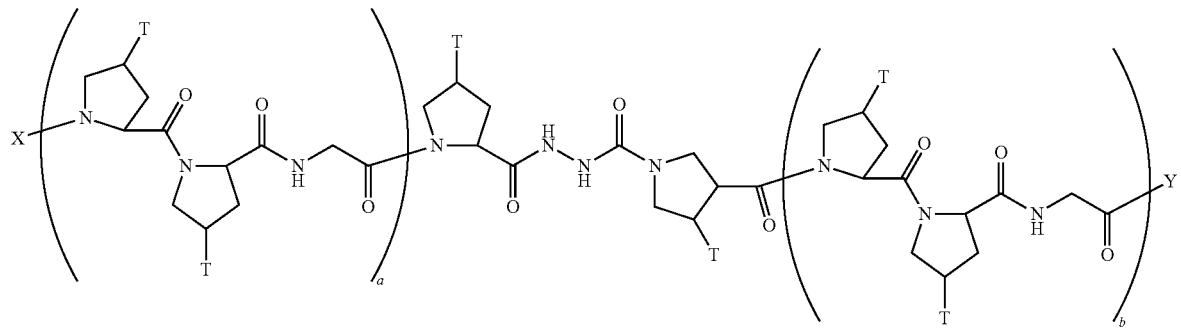

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition according to claim 43 wherein said formula is:

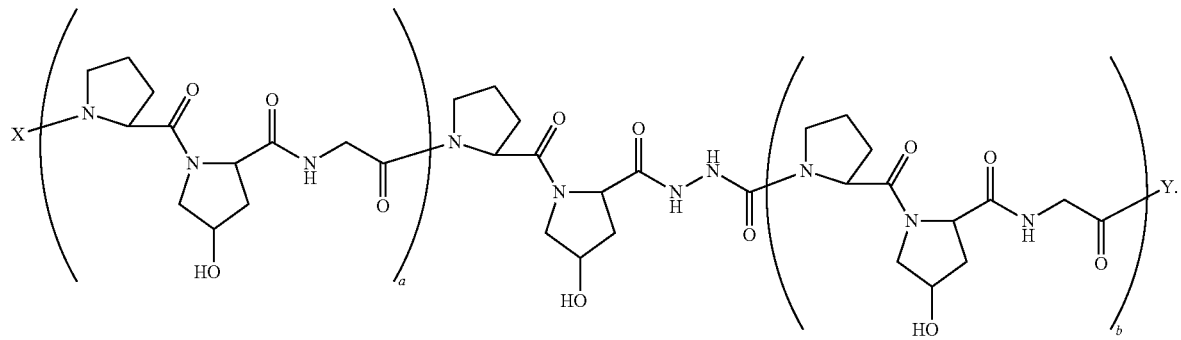

In another aspect, the present invention provides a composition comprising a peptide having the formula:

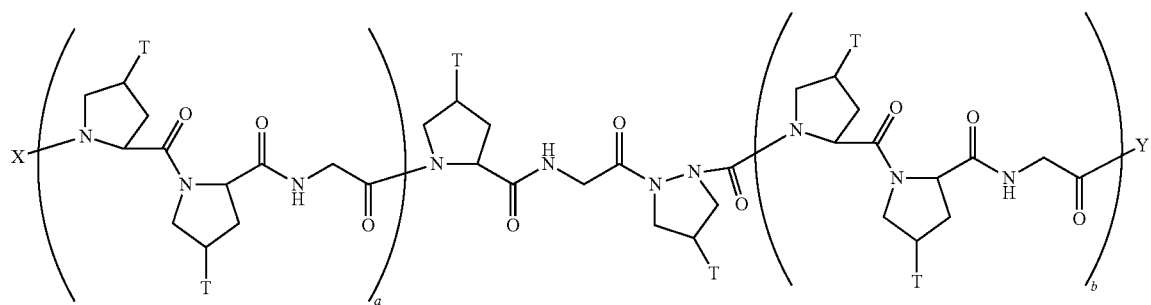

wherein X is selected from the group consisting of acetyl, a label, an AA; Y is selected from the group consisting of amino, a label, an AA; and a and b are integers that together add up to 6 or more; and T is independently selected from —OH and —H.

In another aspect, the present invention provides a composition according to claim 49 wherein said formula is:

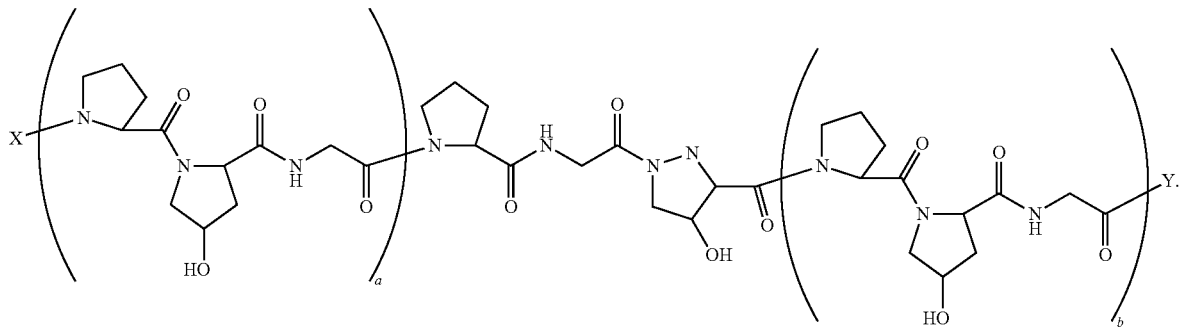

In another aspect, the present invention provides a composition comprising a collagen monomer having the formula:

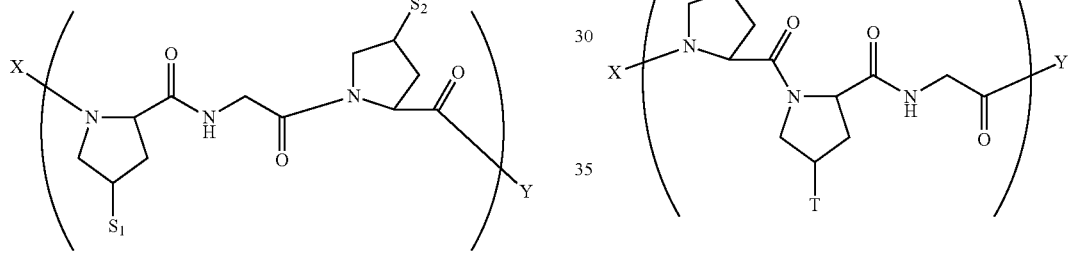

wherein X is selected from the group consisting of $(AA_3)_n$, an AA, $(AA)_2$, acetyl; Y is selected from the group consisting of $(AA_3)_m$, an AA, $(AA)_2$, amino; $S_1$ and $S_2$ are independently selected from —OH, —H and -L-Ch, wherein L is a linker, Ch is a chromophore, and one of said $S_1$ and $S_2$ groups is -L-Ch.

In another aspect, the present invention provides a composition comprising a collagen monomer having the formula:

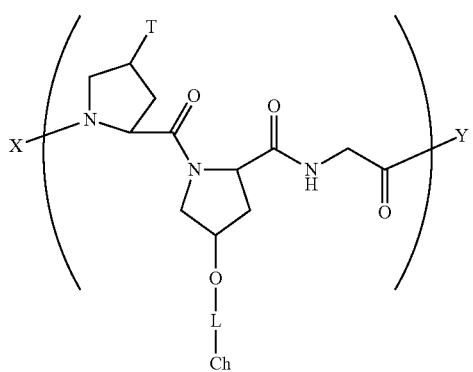

wherein X is selected from the group consisting of $(AA_3)_n$, an AA, $(AA)_2$, acetyl; Y is selected from the group consisting of $(AA_3)_m$, an AA, $(AA)_2$, amino; $S_1$ and $S_2$ are independently selected from —OH, —H and -L-Ch, wherein L is a linker, Ch is a chromophore, and one of said $S_1$ and $S_2$ groups is -L-Ch.

In another aspect, the present invention provides a composition comprising a collagen monomer having the formula:

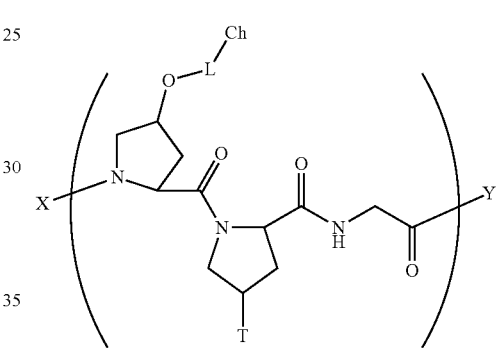

wherein X is selected from the group consisting of $(AA_3)_n$, an AA, $(AA)_2$, acetyl; Y is selected from the group consisting of $(AA_3)_m$, an AA, $(AA)_2$, amino; $S_1$ and $S_2$ are independently selected from —OH, —H and -L-Ch, wherein L is a linker, Ch is a chromophore, and one of said $S_1$ and $S_2$ groups is -L-Ch.

In another aspect, the present invention provides a method of making a composition of claim 1, the method comprising a step of bringing together under conditions for formation of a collagen monomer, at least seven amino acid triplets, wherein one of said triplets comprises an aza-glycine residue.

In another aspect, the present invention provides a method of making a composition of claim 2, the method comprising a step of bringing together under conditions for formation of a collagen monomer, at least seven amino acid triplets, wherein one of said triplets comprises an aza-proline residue. In some embodiments, said step is conducted using solid-phase peptide synthesis (SPPS).

In another aspect, the present invention provides a method of making a composition of claim 1, the method comprising the steps of: (a) providing a POG tripeptide synthon and a solid support with a first protected amino acid or peptide synthon attached to the solid support; (b) deprotecting the first protected amino acid or peptide synthon; (c) coupling a second peptide synthon or an amino acid to the deprotected peptide synthon or amino acid; (d) repeating the process until the desired aza-glycine sequence is completed; and (e) cleaving the completed aza-glycine sequence from the solid support.

In another aspect, the present invention provides a method of making a composition of claim 2, the method comprising the steps of: (a) providing a POG tripeptide synthon and a solid support with a first protected amino acid or peptide synthon attached to the solid support; (b) deprotecting the first protected amino acid or peptide synthon; (c) coupling a second peptide synthon or an amino acid to the deprotected peptide synthon or amino acid; (d) repeating the process until the desired aza-proline sequence is completed; and (e) cleaving the completed aza-proline sequence from the solid support.

In another aspect, the present invention further comprises a dye. In some embodiments, the present invention further comprises a fluorophore.

In another aspect, the present invention provides a method of imaging tissue comprising the steps of: (a) systemically applying a pharmaceutical composition comprising a composition according to claims 59 or 60 to a subject; and b) detecting signal emitted by said composition and forming an image therefrom.

In another aspect, the present invention provides a combinatorial library of collagen monomer analogs characterized in that it includes monomers having at least seven amino acid triplets, wherein one of said triplets comprises an aza-glycine residue; and at least one collagen monomer analog comprising a part of a combinatorial library collagen monomer analog pool. In some embodiments, said collagen monomer analogs are aza-CMPs.

In another aspect, the present invention provides a combinatorial library of collagen monomer analogs characterized in that it includes monomers having at least seven amino acid triplets, wherein one of said triplets comprises an aza-proline residue; and at least one collagen monomer analog comprising a part of a combinatorial library collagen monomer analog pool. In some embodiments, said collagen monomer analogs are aza-CMPs.

In another aspect, the present invention provides a drug delivery composition comprising: an aqueous carrier containing a pharmaceutically active agent; and collagen hydrogel microspheres containing said pharmaceutically active agent, wherein said microspheres comprise collagen monomers comprising at least seven amino acid triplets, wherein one of said triplets comprises an aza-glycine residue.

In another aspect, the present invention provides a drug delivery composition comprising: an aqueous carrier containing a pharmaceutically active agent; and collagen hydrogel microspheres containing said pharmaceutically active agent, wherein said microspheres comprise collagen monomers comprising at least seven amino acid triplets, wherein one of said triplets comprises an aza-proline residue.

In another aspect, the present invention further comprises a composition wherein the collagen monomers are collagen Heterotrimeric Parallel Triple-helix mimics (HPT-mimics), capable of targeting and modulating collagen-protein interactions.

In another aspect, the present invention provides a method of treating a skin wound in a subject in need thereof comprising administering a therapeutically effective amount of the composition of the present invention.

In another aspect, the present invention provides a method of treating chronic wounds in a subject in need thereof comprising administering a therapeutically effective amount of the composition of the present invention. In some embodiments, the composition is aza-CMP.

In another aspect, the present invention provides a method of treating a pathology using antifibrotic therapy in a subject in need thereof comprising administering a therapeutically effective amount of the composition of any one of claims 1 to 50. In some embodiments, the pathology is liver cirrhosis. In some embodiments, wherein the composition is an HSP47 inhibitor.

In another aspect, the present invention provides a composition comprising a first collagen peptide comprising at least one amino acid triplet, wherein said triplet comprises an aza-glycine residue.

In another aspect, the present invention provides a composition comprising a first collagen peptide comprising at least one amino acid triplet, wherein said triplet comprises an aza-proline residue. In some embodiments, the present invention further comprises a second collagen peptide comprising at least one amino acid triplet, wherein said triplet comprises an aza-glycine residue and a third collagen peptide comprising at least one amino acid triplet, wherein said triplet comprises an aza-glycine residue. In some embodiments, the present invention further comprises a second collagen peptide comprising at least one amino acid triplet, wherein said triplet comprises an aza-proline residue and a third collagen peptide comprising at least one amino acid triplet, wherein one of said triplet comprises an aza-proline residue.

BRIEF DESCRIPTION OF THE DRAWINGS

FIG. 4 shows HPT-mimics for probing the collagen interactome. Following the optimization of synthetic protocols, a library of HPT-mimics tailored to study the interactions between collagen and various biologically relevant proteins can be designed. The common core of A and B strands allow for synthetically straightforward integration of specific protein targeting sequences in the C strand.

Figure 1:
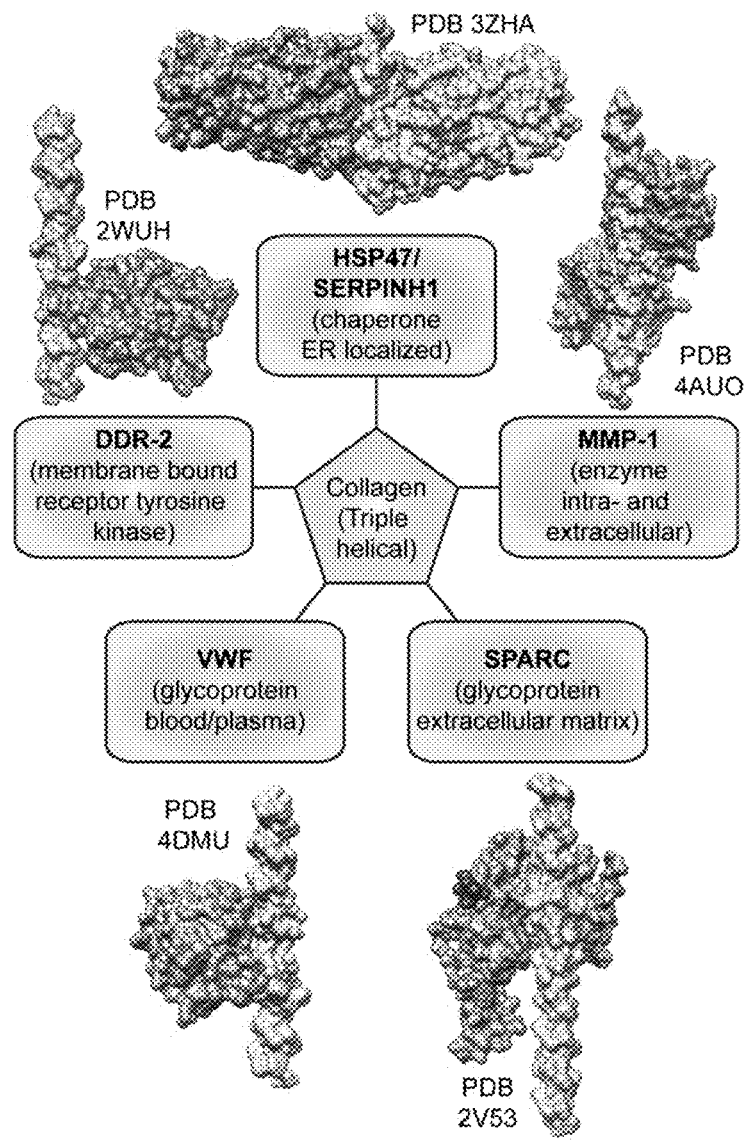
FIG. 1 shows a sampling of important proteins in the collagen interactome. A representative sample of therapeutically relevant collagen binding proteins along with 3D structures of their associated collagen-protein complexes and PDB numbers.

Electron density maps of 17 along with characterization of H bonding in this triple-helical Arg-containing azapeptide.

FIG. 6 shows chemical structure of collagen control peptides 1 and 2 and azGly containing peptides 3 and 4. It should be noted that control peptide 2 and azGly peptide 4 both actually have an —OH off the central proline of the structures.

FIG. 7A-FIG. 7E depicts the Unfolding/refolding data for collagen model peptides. (a) Table of unfolding and refolding data. Values of Tm (standard error<1° C.) were determined in triplicate by CD spectroscopy at scan rates of 12° C./h and 36° C./h. (b) CD wavelength scans of homotrimers formed by peptides 1-4. (c) Unfolding curves for the thermal transition of peptides 1-4 at 12° C./h. (d) Refolding of peptides was observed by monitoring the recovery of ellipticity after thermal denaturation (e) SEC-MALS analysis confirming the presence of the trimeric peptide assemblies for 1-4. The presence of the trimeric state for peptides 3 and 4 was also verified by sedimentation equilibrium analysis using analytical ultracentrifugation (AUC). Control peptide 5 contains a central D-proline and serves as a monomeric standard for SEC-MALS analysis.

Figure 8:
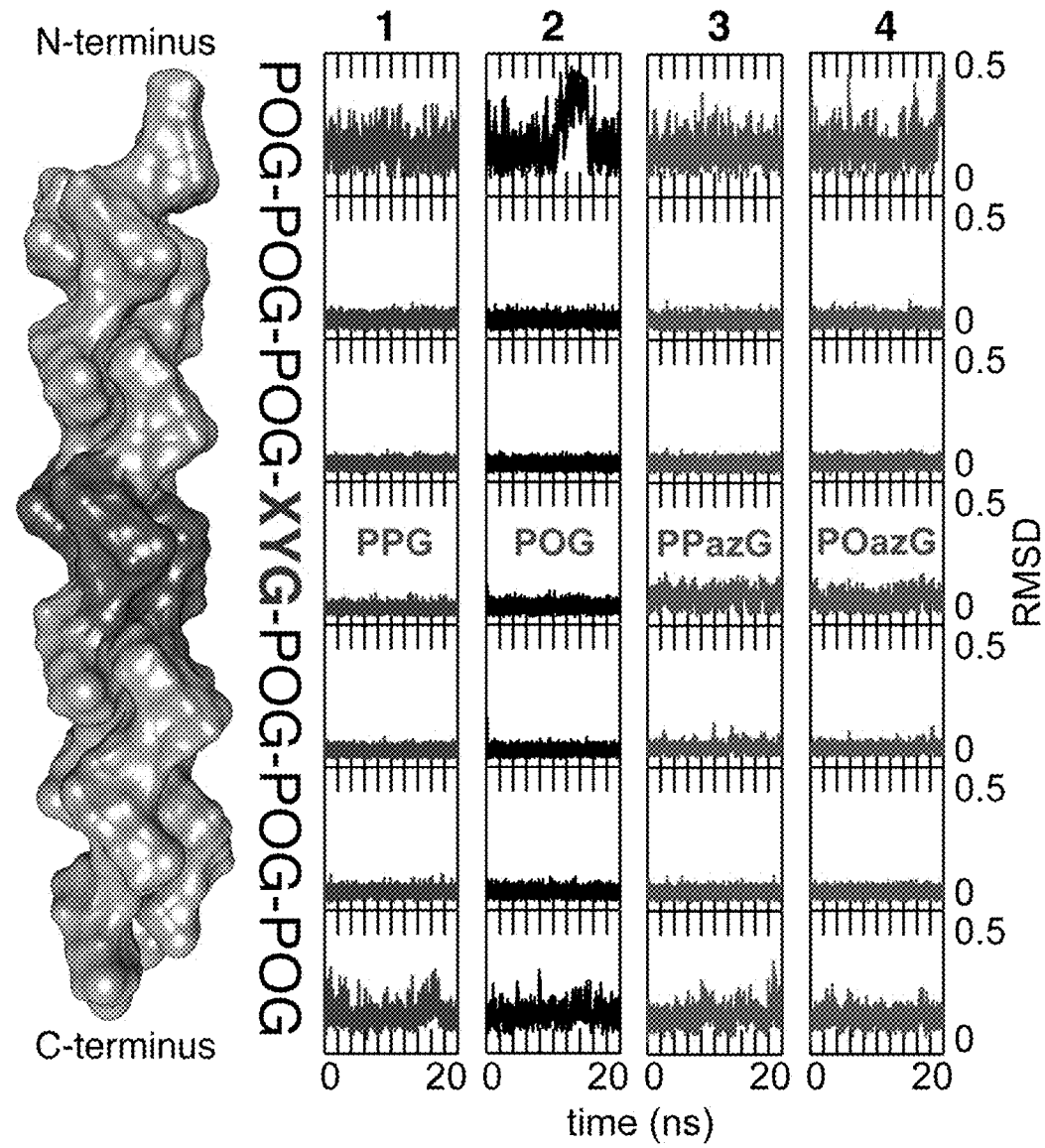

FIG. 8 depicts the model of the collagen triple helix with the central variable triplet highlighted in red. Plot of the RMSD for the heavy atoms of each trimeric triplet of each simulated collagen peptide system compared to a common reference crystal structure used to build all starting MD models. Reference crystal structure used was PDB 3B0S.

FIG. 9A-FIG. 9D shows the hydrogen bond analysis for MD simulations of collagen model peptide 4. (a) Cross section through collagen triple helix showing possible azGly hydrogen bonds (b) Schematic of hydrogen bond parameters. (c) Hydrogen bond distance measurements and correlations for A, B, and C from FIG. 9a. (d) Hydrogen bond angle measurements for A, B, and C. Grey watermark on plots designates hydrogen bond angles for non-azGly peptide system. Shaded regions on plots designate optimal hydrogen bond parameters.

Figure 10:
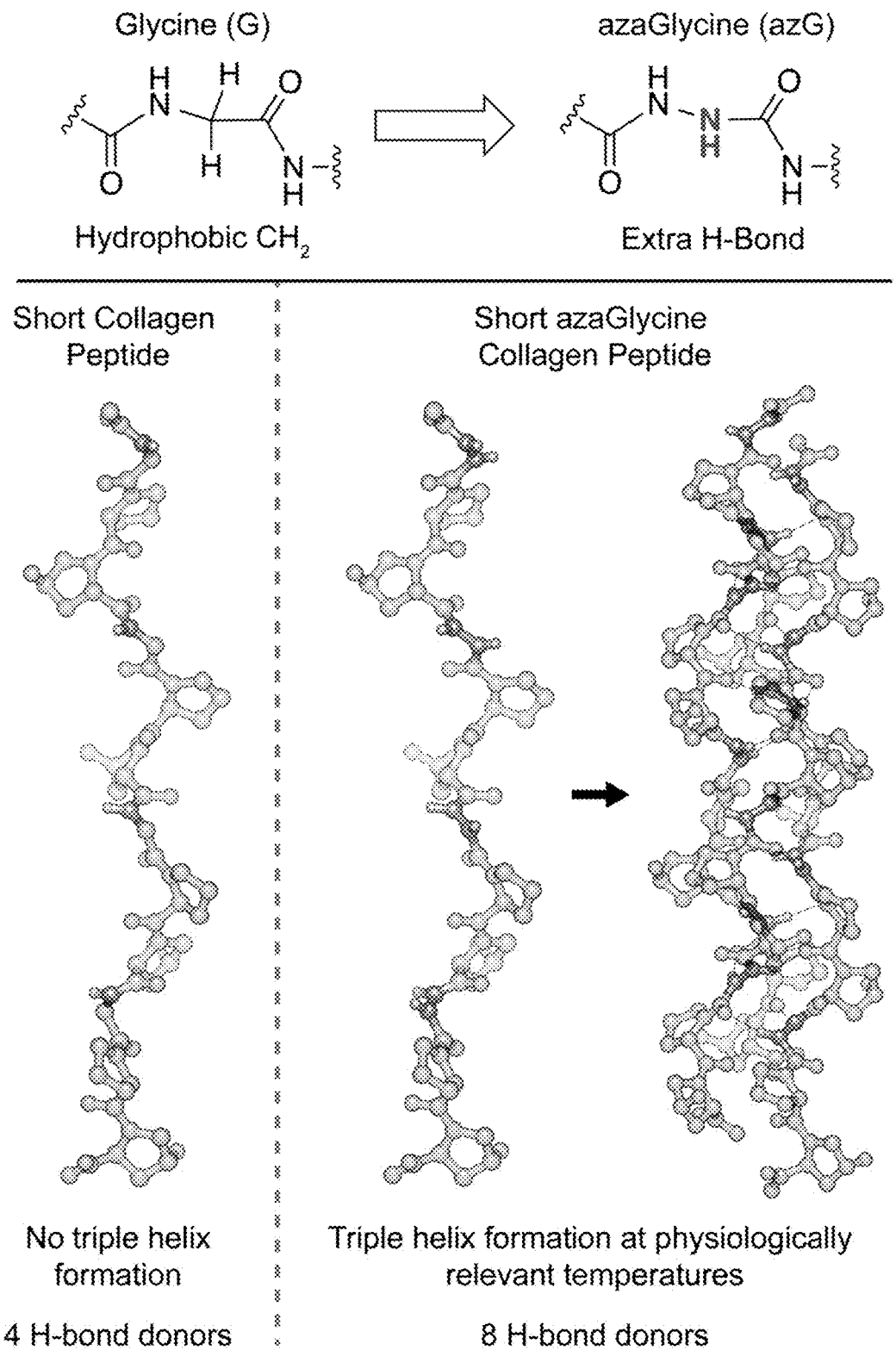
Figures 12A, 12B, 12C, 12D:
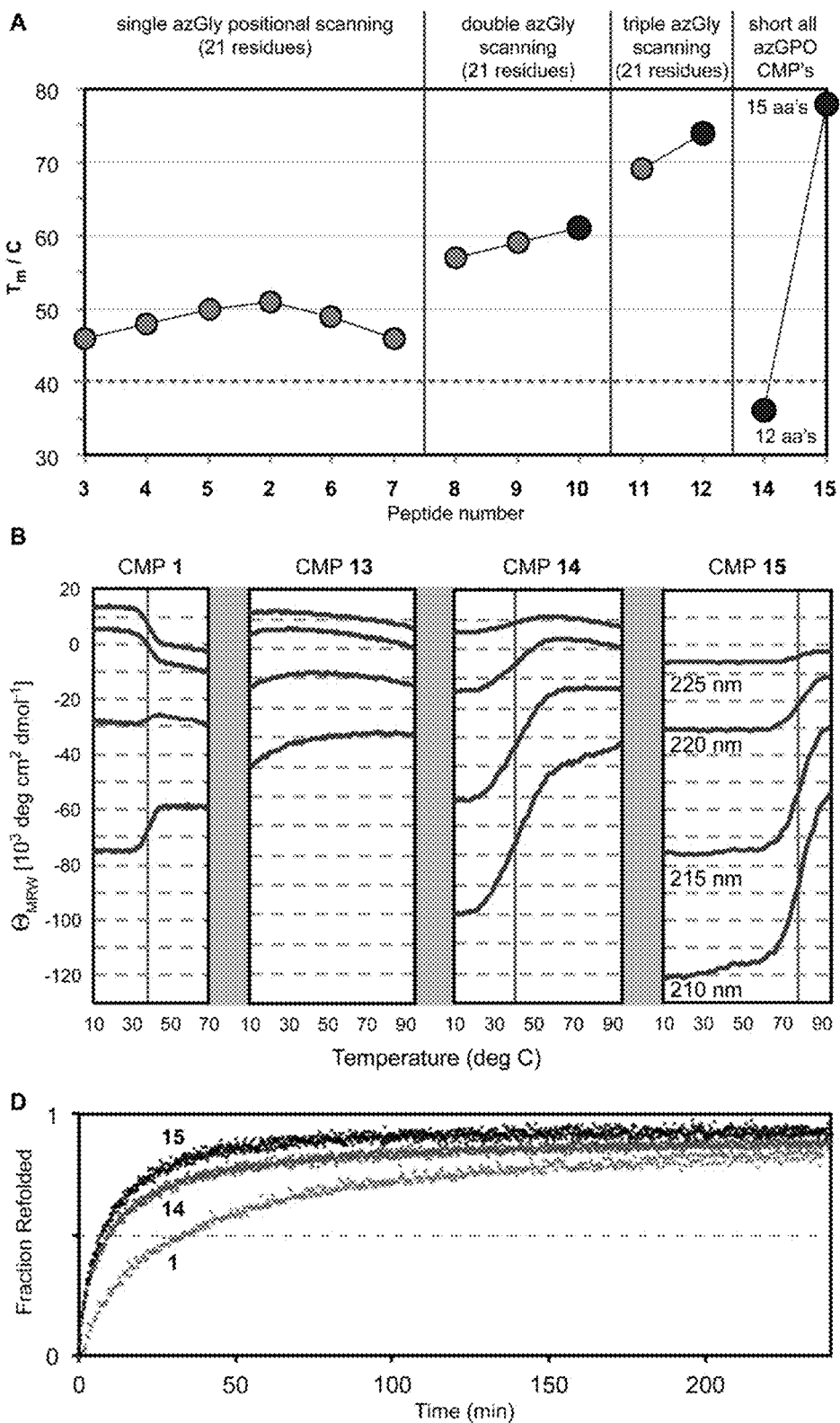

FIG. 10 Top) Illustration of the substitution of aza-glycine (azG) for glycine (G) in a collagen-mimetic peptide. The new —NH group, which is a hydrogen bond donor, is shown in blue. Bottom) Three-dimensional representation of a (GPO)4 collagen-like peptide (left) compared with its aza-glycine-substituted analogue, (azGPO)4 (right). The azG-containing peptide spontaneously assembles into a triple helix at physiologically relevant temperatures, while the unaltered peptide does not. Hydrogen bonds between members of the triple helix are shown by thin gray lines.

FIG. 11A-FIG. 11B A) General structure of collagen model peptides composed of multiple units of Pro-Hyp-Gly/azGly. B) Schematic structures of collagen model peptides 1-14, along with their experimentally determined melting temperatures (Tm). Values of Tm were determined in triplicate by CD spectroscopy at scan rates of 12° C./h. Schematic presentation of the skeleton of CMPs with symbol explanation shown in the ellipsoid. The symbols enclosed by incomplete ellipsoids indicate amino acids that were individually incorporated during the synthesis, i.e. not as part of a synthon.

FIG. 12A-FIG. 12D A) Summary chart of Tm of all peptides in this study on the same scale. The dotted blue line indicates the Tm of collagen model peptide 1. Pep-tides are grouped by number of azGly substitutions. B) Representative unfolding data for collagen model peptides 1, 13, 14, and 15, as monitored at 210, 215, 220, and 225 nm by CD spectroscopy. Melting temperatures are indicated by red lines. D) Refolding of peptides 13, 14, and 1 observed by monitoring the recovery of ellipticity after thermal denaturation via CD spectroscopy.

Figures 13A, 13B, 13C:
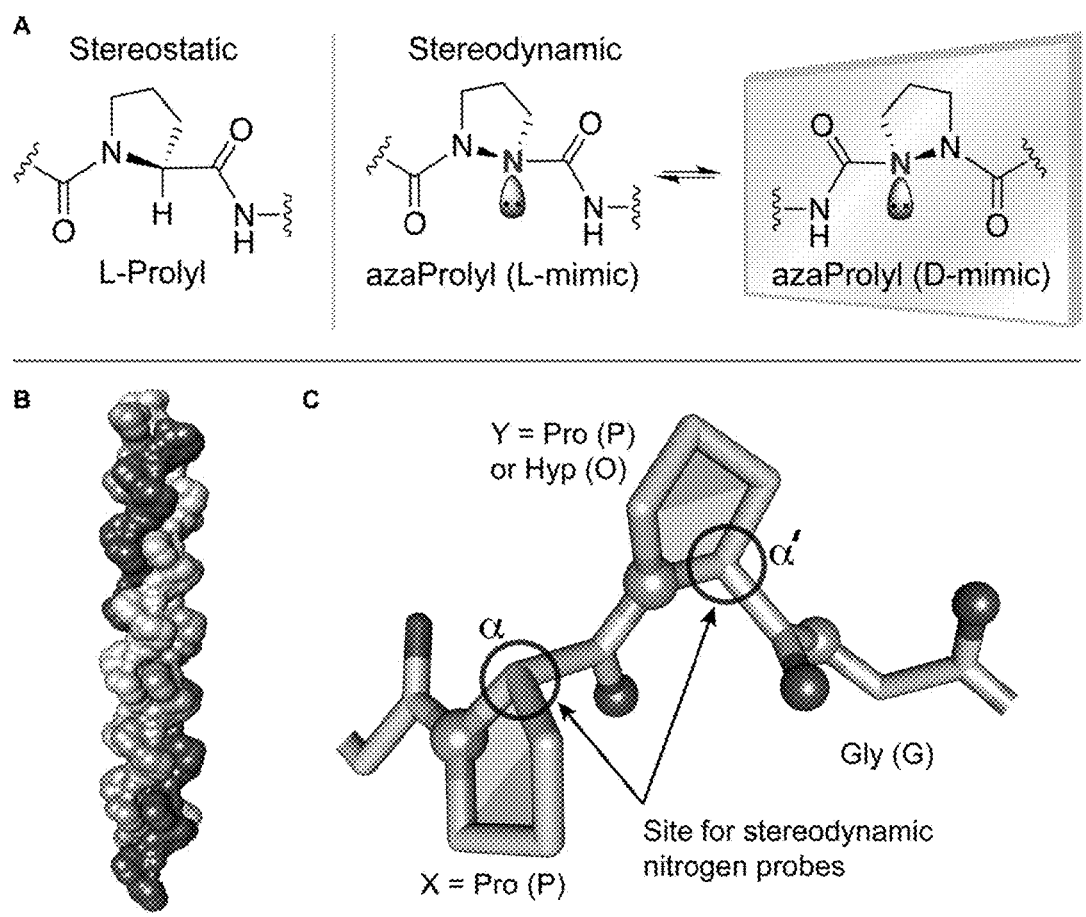

FIG. 13A-FIG. 13C A) Comparison between configurationally-stable L-proline and stereodynamic aza-proline. Aza-proline could potentially sample both enantiomeric geometry of proline B) Structures of a triple-helical collagen model peptide. C) Expanded view of the -Pro-Pro-Gly-tripeptide repeat with detailed view showing designated torsional descriptors and proline stereocenters. Heteroatoms are differentially colored red=oxygen, blue=nitrogen, and beige=carbon.

Figure 14:
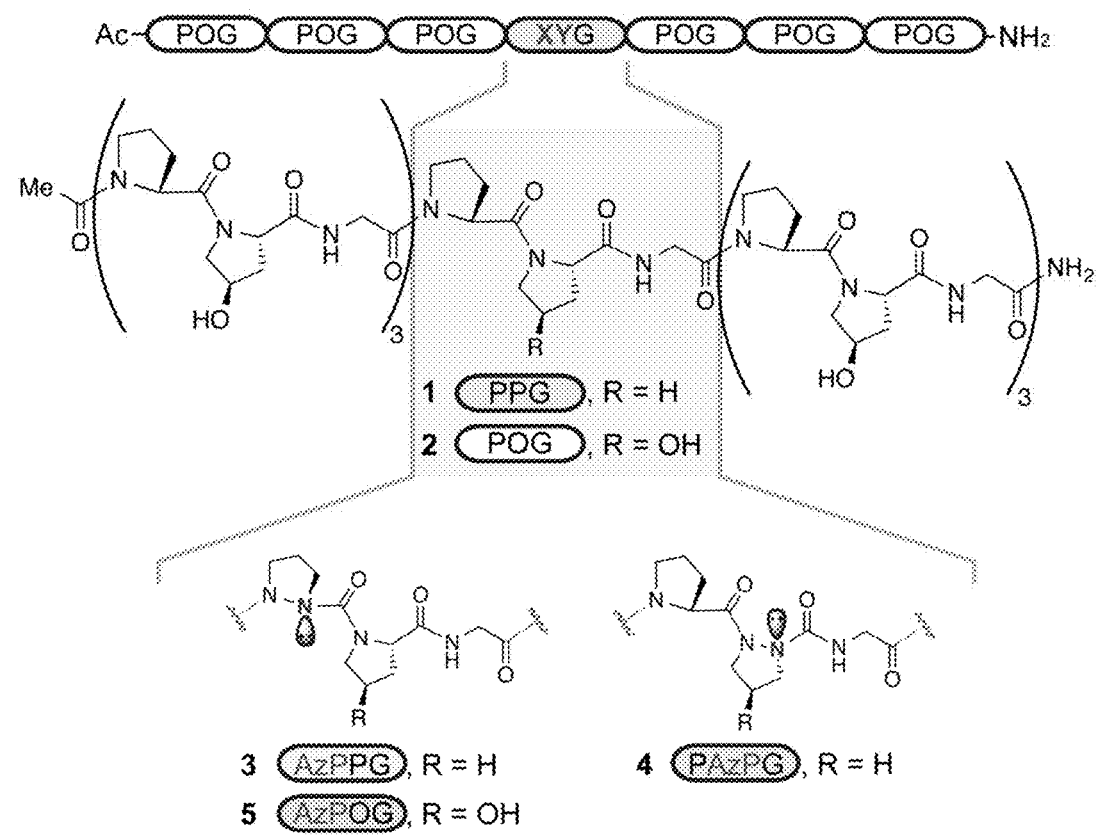

FIG. 14 Structures of collagen model peptides composed of multiple units of Pro-Hyp(Pro)-Gly. The blue color and the lone pair of electrons were used to highlight the location of the C to N mutation with the blue nitrogen acting as a potential stereodynamic center. Schematic presentation of the skeleton of CMPs with symbol explanation shown in the ellipsoid.

FIG. 15 Unfolding and refolding data for collagen model peptides 1-5. The Tm values were determined in triplicate by CD spectroscopy at scan rates of 12° C./h. Schematic presentation of the CMP skeleton with the symbol definition shown in the ellipsoid.

Figure 16:
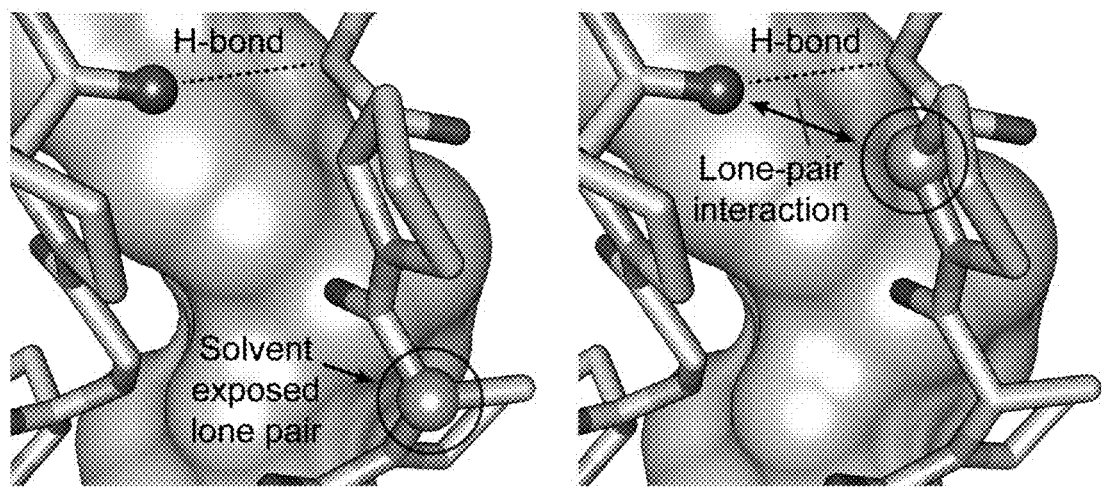

FIG. 16 Expanded view of the -Pro-Pro-Gly- tripeptide repeat with a detailed view of the proline stereocenters. Heteroatoms are colored as follows: red=oxygen, blue=nitrogen, and beige=carbon. Left: microenvironment of peptide 3 where the C to N mutation of proline occurs in the Xaa position. Right: microenvironment of peptide 4 where the C to N mutation of proline occurs in the Yaa position.

Figures 17A, 17B, 17C:
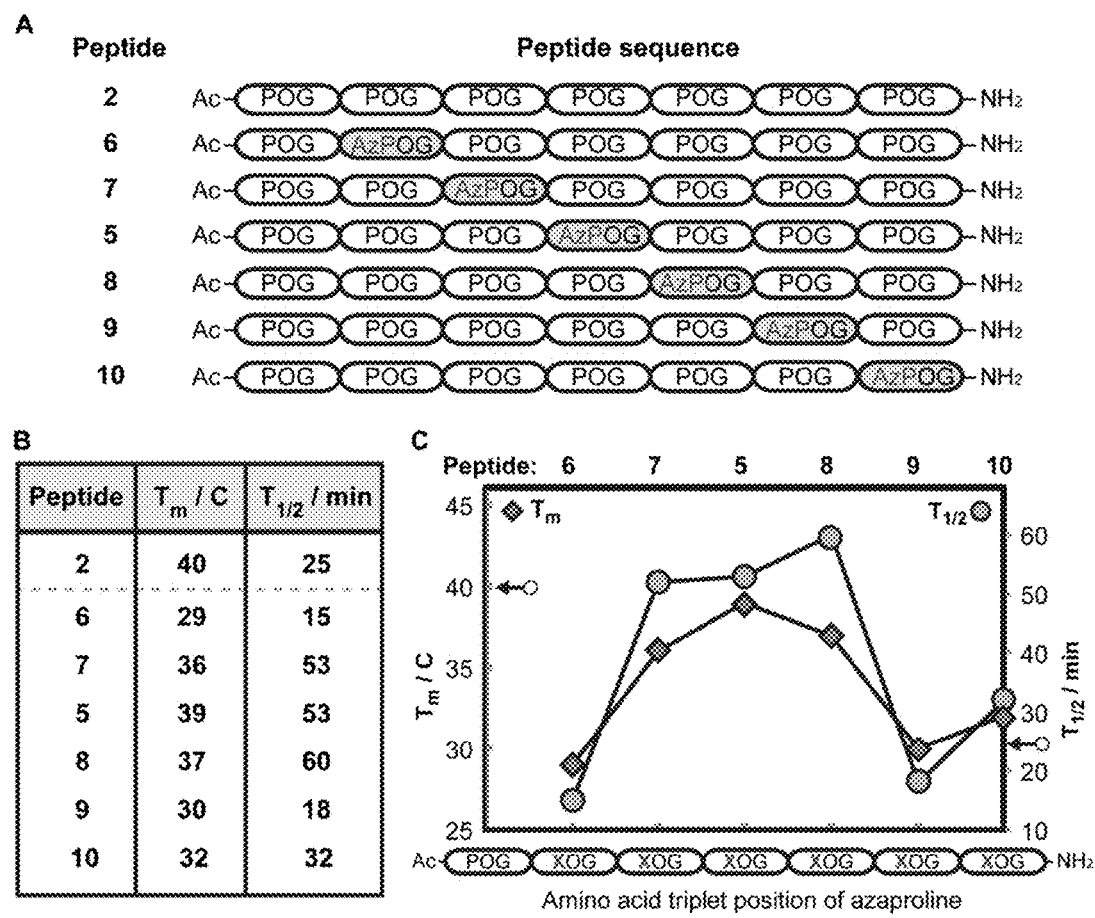

FIG. 17A-FIG. 17C A) Schematic representation with ellipsoids representing trimeric units to visualize where the trimer containing stereodynamic center was installed in the 21-mer peptide. B) Tabulated result for the melting temperature and refolding half-time of peptides 2, 5-10. C). Summary chart of the results from table; The x axis shows the relative position of the mutation site compared to the N-terminus of the 21-mer CMP.

FIG. 18 Structure of peptides 11-13 containing more than one AzPro residues.

FIG. 19 Top) Illustration of the substitution of glycine (G) for aza-glycine (azG), which contains an extra H-bond donor. Bottom) Chemical structures of arginine-containing CMP 1 and its aza-glycine-containing peptide analog 2. Aza-glycine is located directly adjacent to the arginine (Arg) residue in CMP 2.

Figures 20A, 20B:
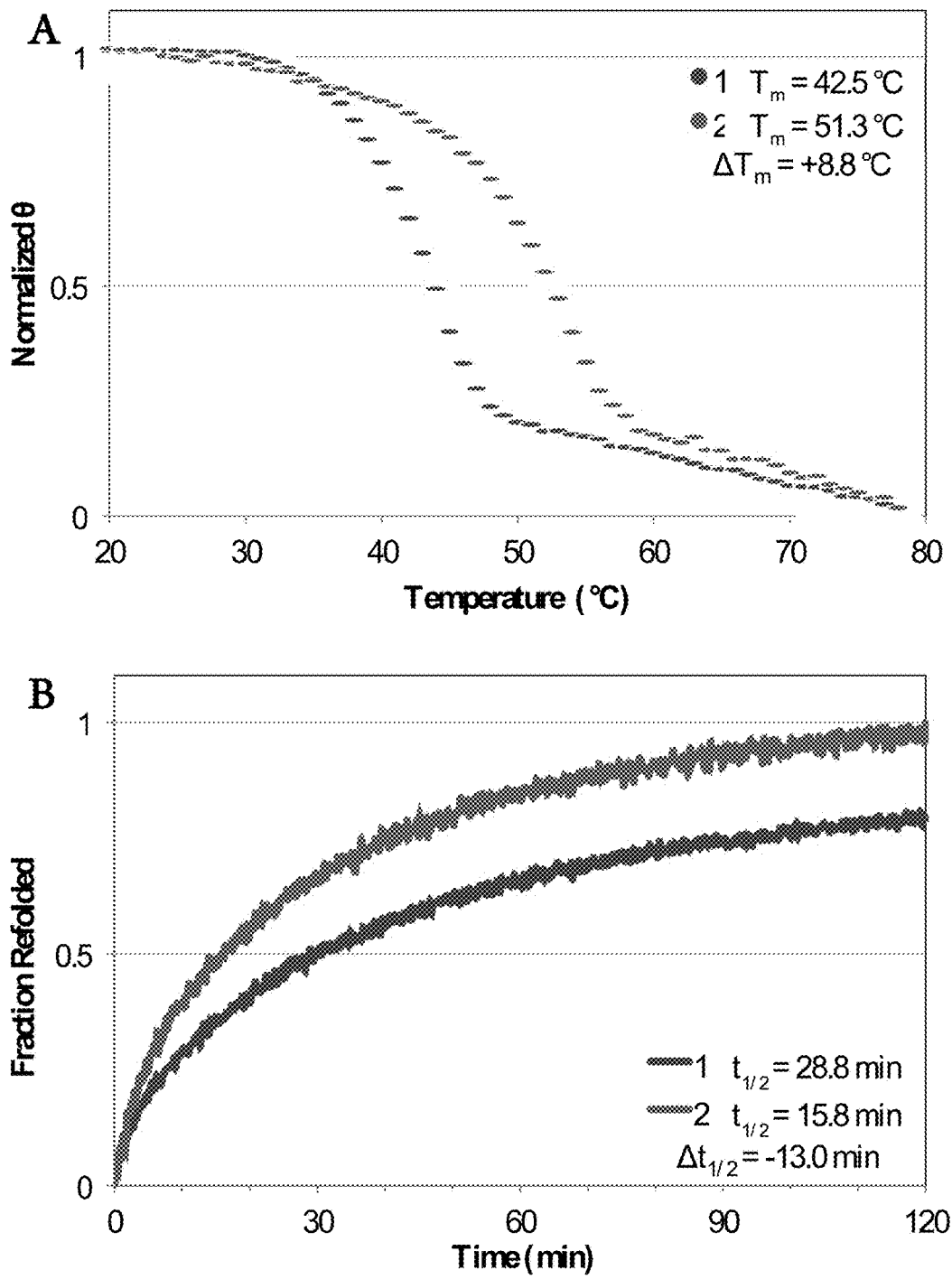

FIG. 20A-FIG. 20B Circular dichroism (CD) measurements indicating enhanced thermal and kinetic stability resulting from azGly substitution. A) Unfolding curves measuring the thermal transition of peptides 1 and 2 at 12° C./h. B) Kinetic refolding of peptides 1 and 2 observed by monitoring the recovery of ellipticity at 224 nm after thermal denaturation.

Figures 21A, 21B, 21C:
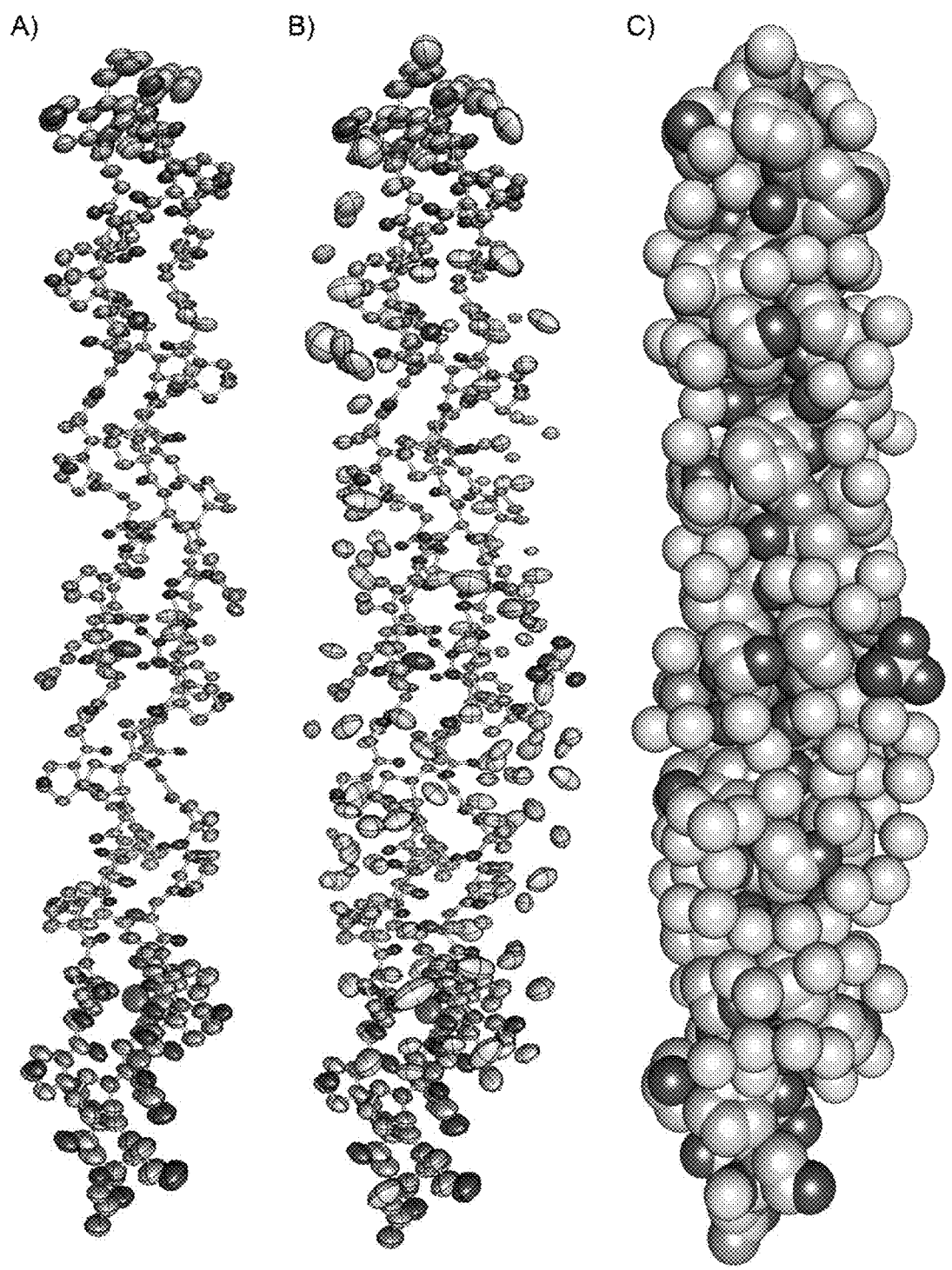

FIG. 21A-FIG. 21C A) Overall triple helical structure of azGly-containing CMP 2 solved to 1.13 Å resolution ($R_{work}$=12.9%, $R_{free}$=15.9%, Space Group=P2$_1$). Structure shown as anisotropic thermal ellipsoids at 50% probability level. B) Triple helical structure shown with complete hydration shell and sulfate ion as anisotropic thermal ellipsoids at 50% probability level. C) Space-filling model of X-ray structure with complete shell of hydrations and sulfate.

Figure 22A:
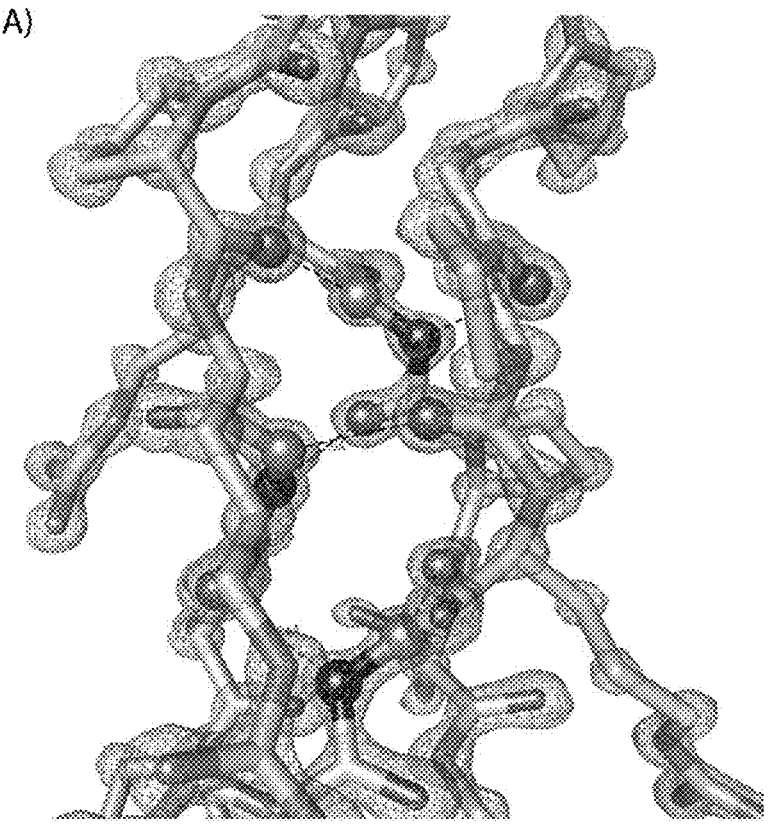
Figure 22B:
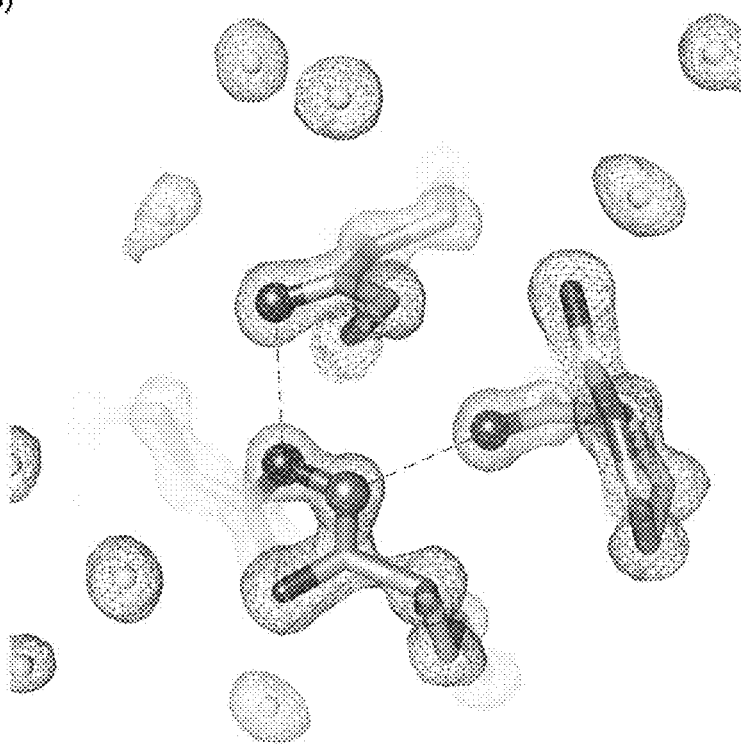

FIG. 22A-FIG. 22B A) Electron density map contoured at 2σ showing aza-glycines at the triple helix interface. B) Transverse section through the collagen triple helix crystal structure showing a single azGly residue hydrogen bonding to two different amide carbonyls on separate adjacent peptide strands. The canonical glycine-like hydrogen bond is maintained with a distance of 2.8-2.9 Å. The newly added azGly nitrogen (dark blue) also maintains a short 2.8-2.9 Å distance from the adjacent carbonyl with a side-on positioning. Distances are shown in angstroms. Red=oxygen, tan=carbon, light blue=nitrogen atoms already present in collagen, dark blue=nitrogen atom from aza-glycine, aqua=water molecules. Structure: 1.13 Å resolution ($R_{work}$=12.9%, $R_{free}$=15.9%, Space Group=$P2_1$).

Figure 23:
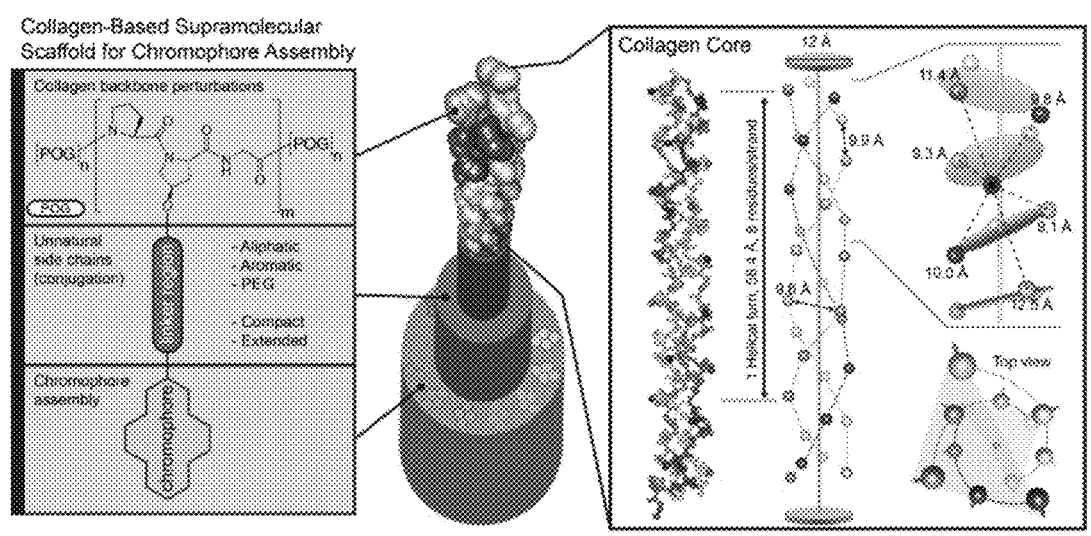

FIG. 23 shows an exemplary structure of collagen-dye conjugate, depiction of multichromophore assembly, and distance measurements for placement of chromophores on collagen.

Figure 24:
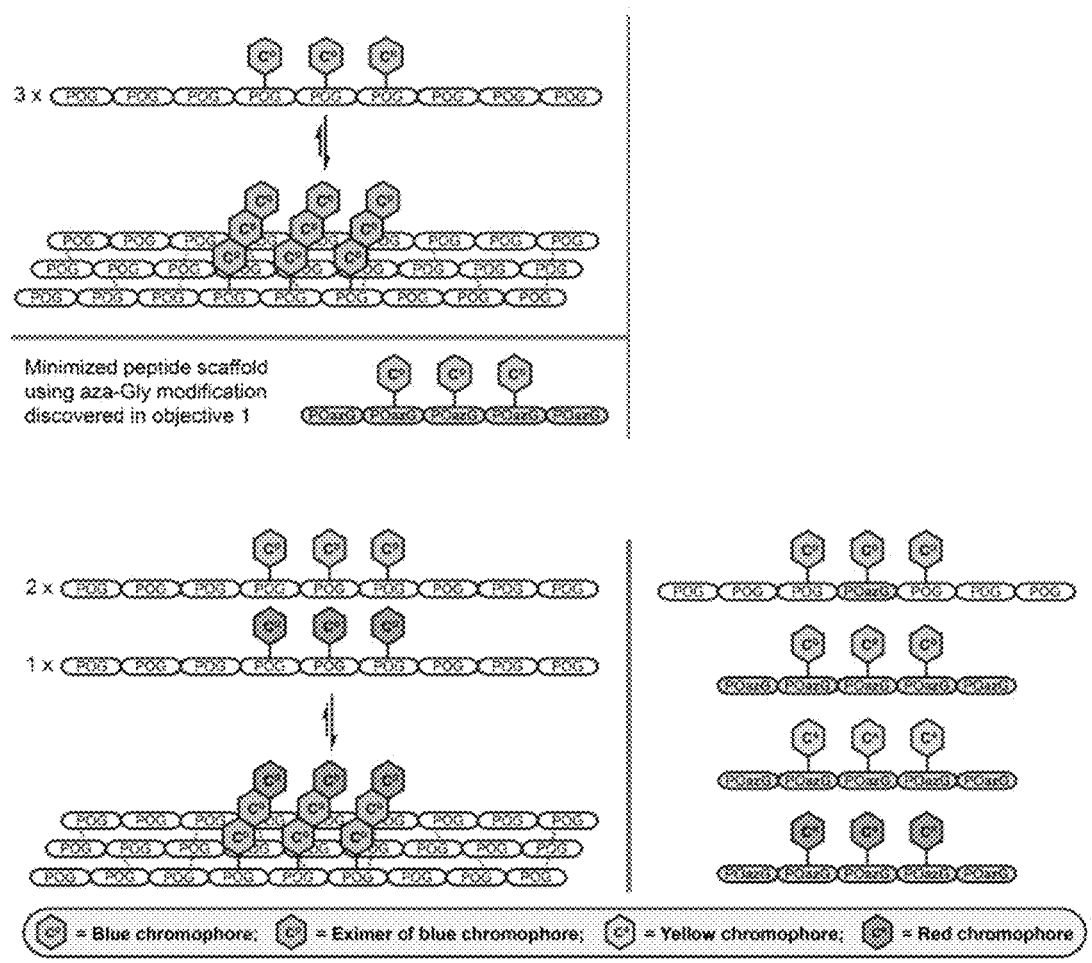

FIG. 24 shows a schematic representation of a precision scaffold with chromophore attached.

FIG. 25A-FIG. 25C A. Structure of collagen-dye conjugate. B. Fluorescence emission from the dye prior to peptide conjugation (labeled "One Dye" in figure, purple), the single strand form (blue emission) and the triple helical form (cyan emission). C. Fluorescence emission of collagen peptides labeled with three pyrene dyes in the single strand and triple helical forms.

Figure 26:
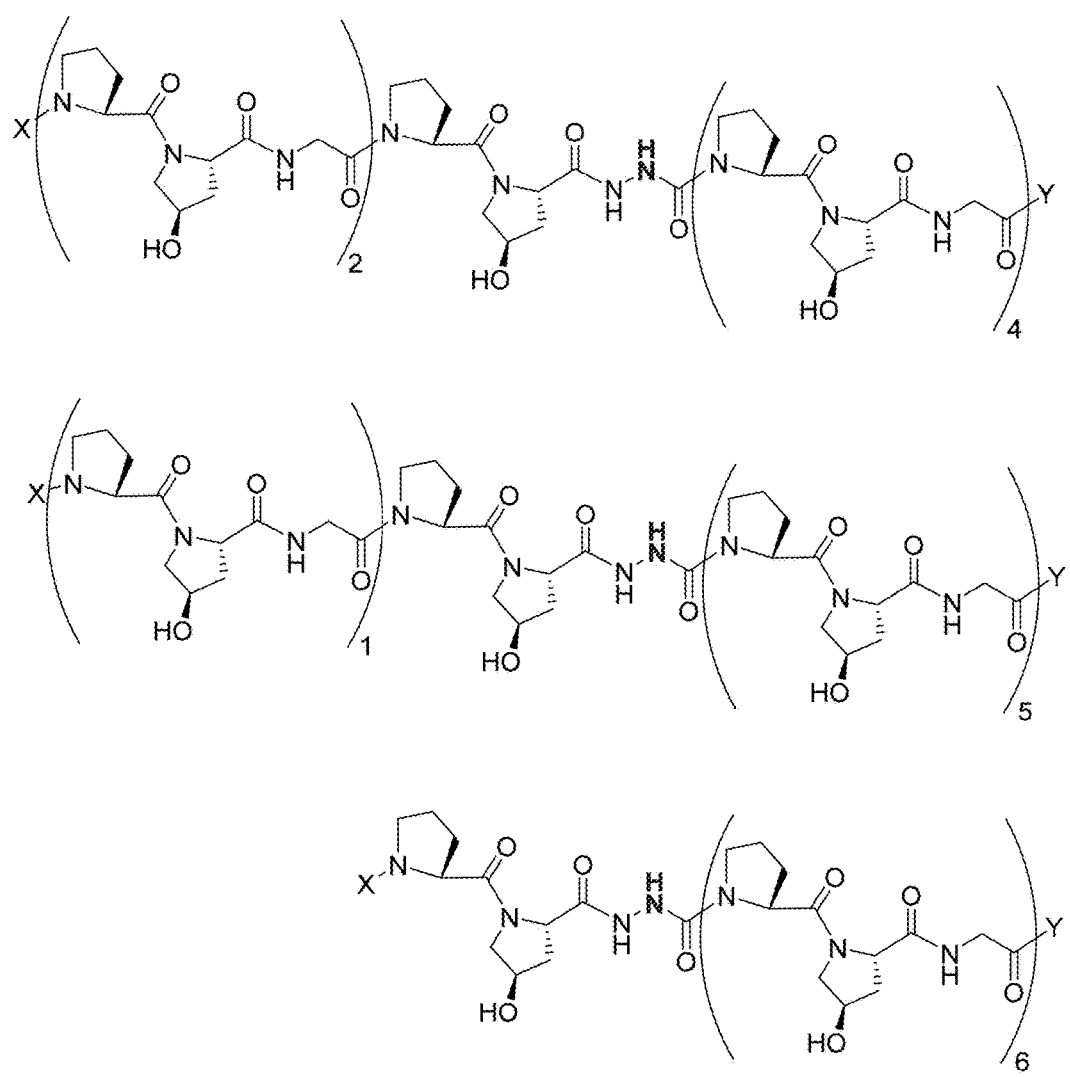

FIG. 26 shows the structures of exemplary embodiments of aza-CMPs in accordance with aspects of the present invention FIG. 27 shows further exemplary embodiments of aza-CMPs in accordance with aspects of the present invention.

Figure 28:
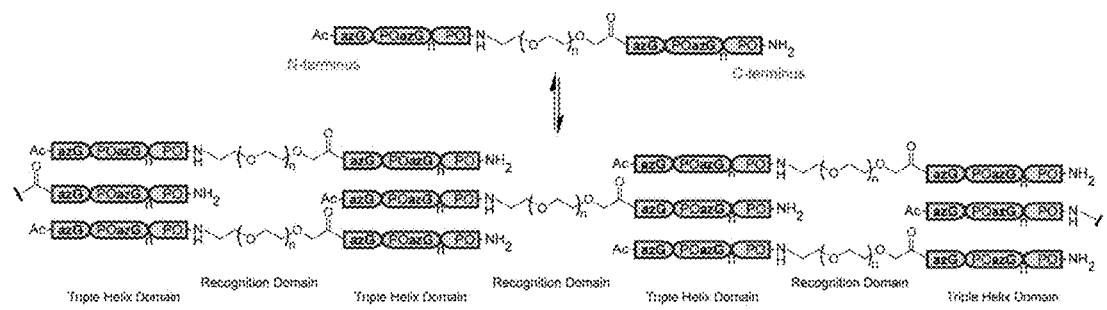

FIG. 28 shows an exemplary self-assembly schematic of one-dimensional collagen azapeptide materials.

Figure 29:
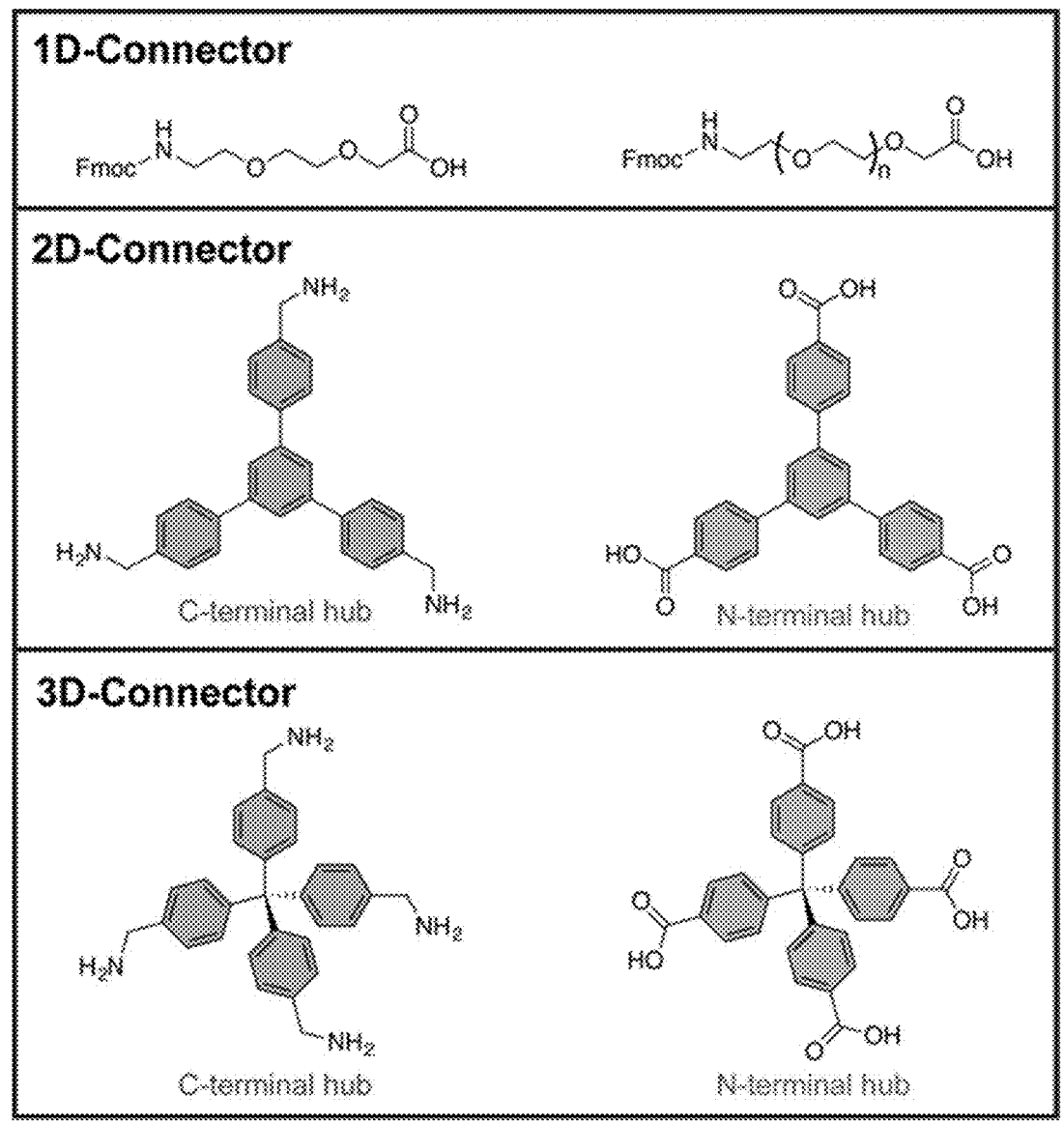

FIG. 29 shows structures of exemplary 1, 2, and 3-dimensional connectors for azapeptide biomaterial matrices. 1D connectors will be easily tuned according to their specific application by varying the length of the PEG linker sequence between the carboxy and amino termini of the overall block copolymer. 2D and 3D connectors are designed to be outfitted with specific azapeptide sequences on the protruding —NH$_2$ and —COOH groups of the C- and N-terminal hubs. This modularity will allow these connectors to be adapted to myriad applications without need to modify their fundamental structure.

Figure 30:
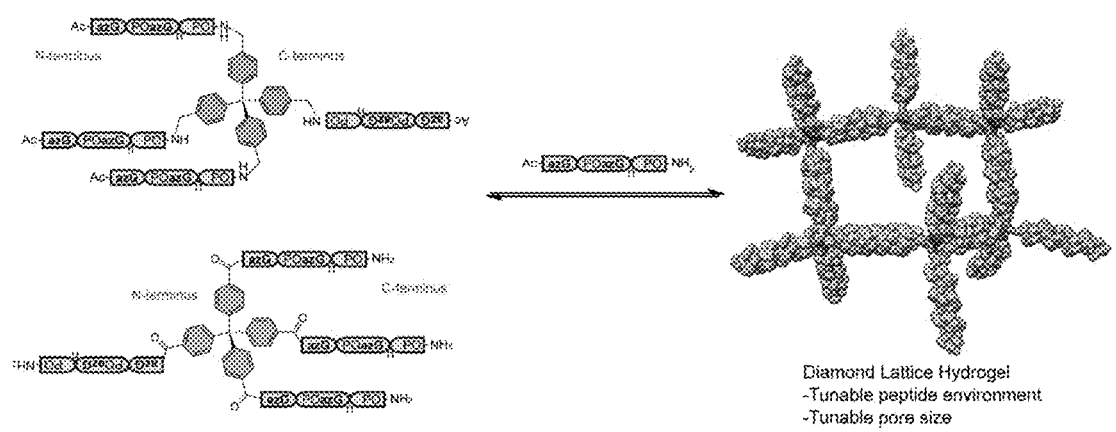

FIG. 30 shows an exemplary schematic illustrating the reversible self-assembly of 3D azapeptide materials and representative fragment of the higher order hydrogel matrix.

Figure 31:
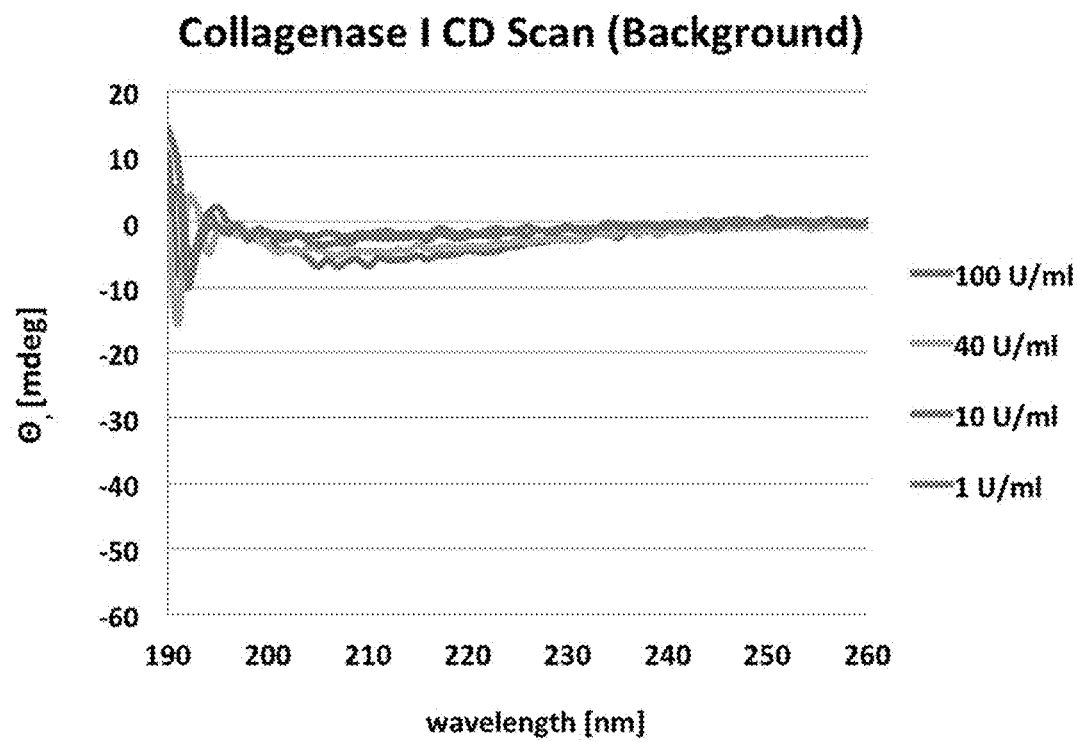

FIG. 31 shows collagenase I background CD scan.

Figure 32:
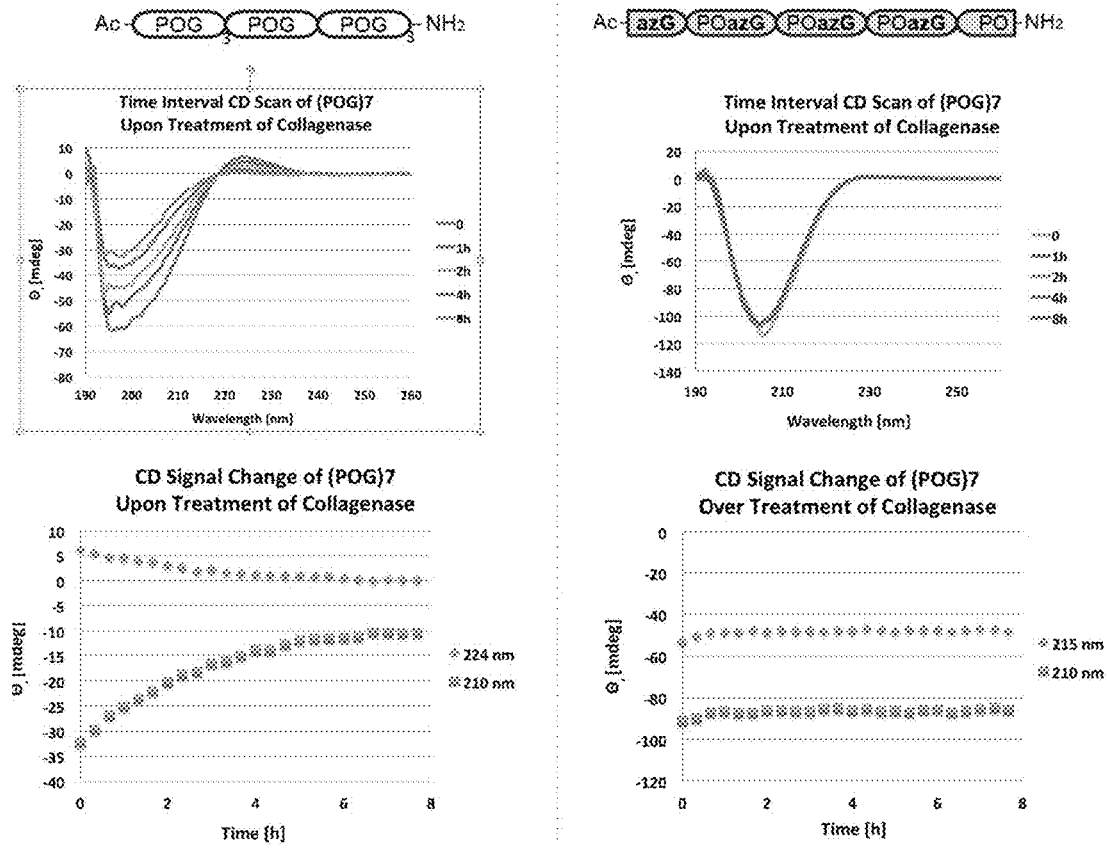

FIG. 32 shows comparison of CD signals for complete enzymatic digestion vs. complete resistance of enzymatic digestion by an azapeptide.

Figure 33:
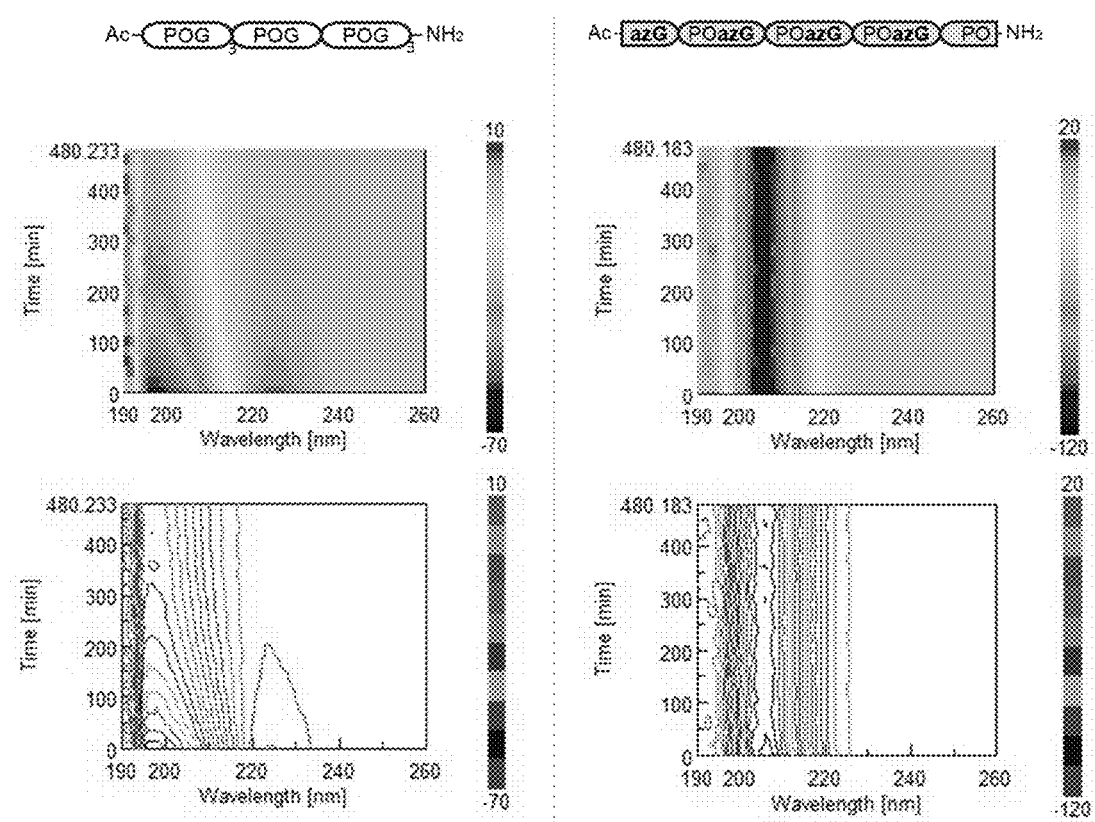

FIG. 33 shows a full CD interval scan of an azapeptide vs. its non-aza conterpart.

Figure 34:
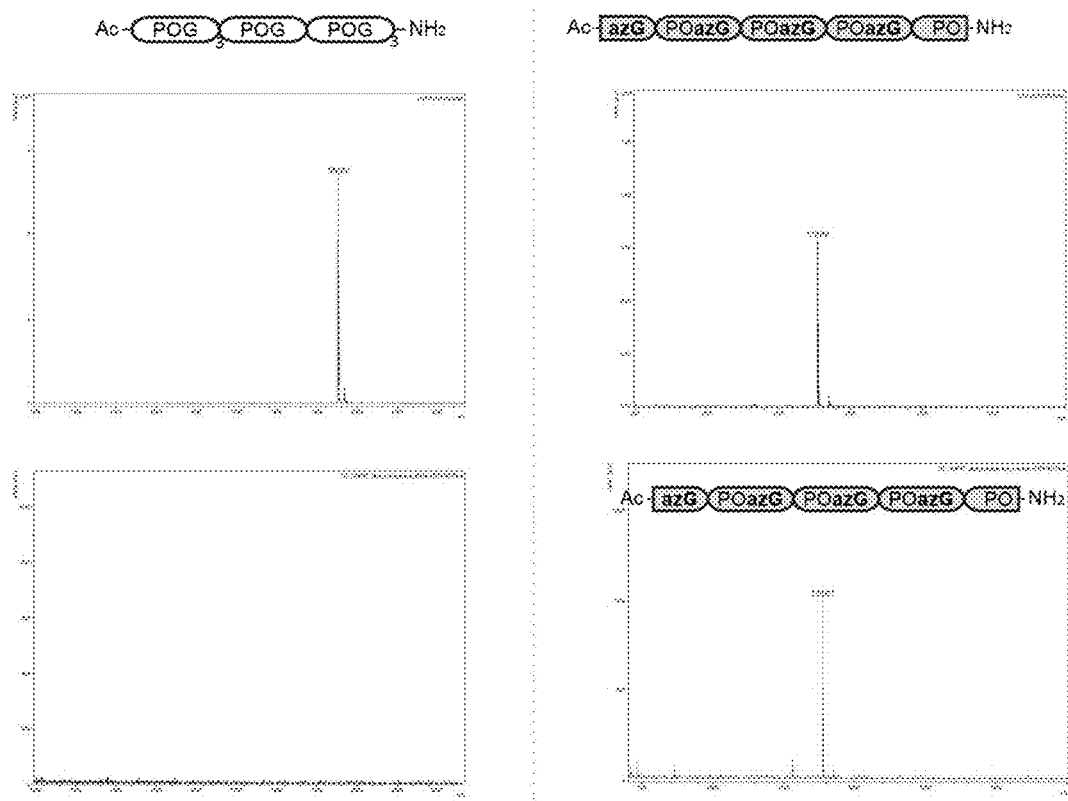

FIG. 34 shows Maldi Mass Spectroscopy detection of enzymatic substrates before and after addition of collagenase.

Figure 35:
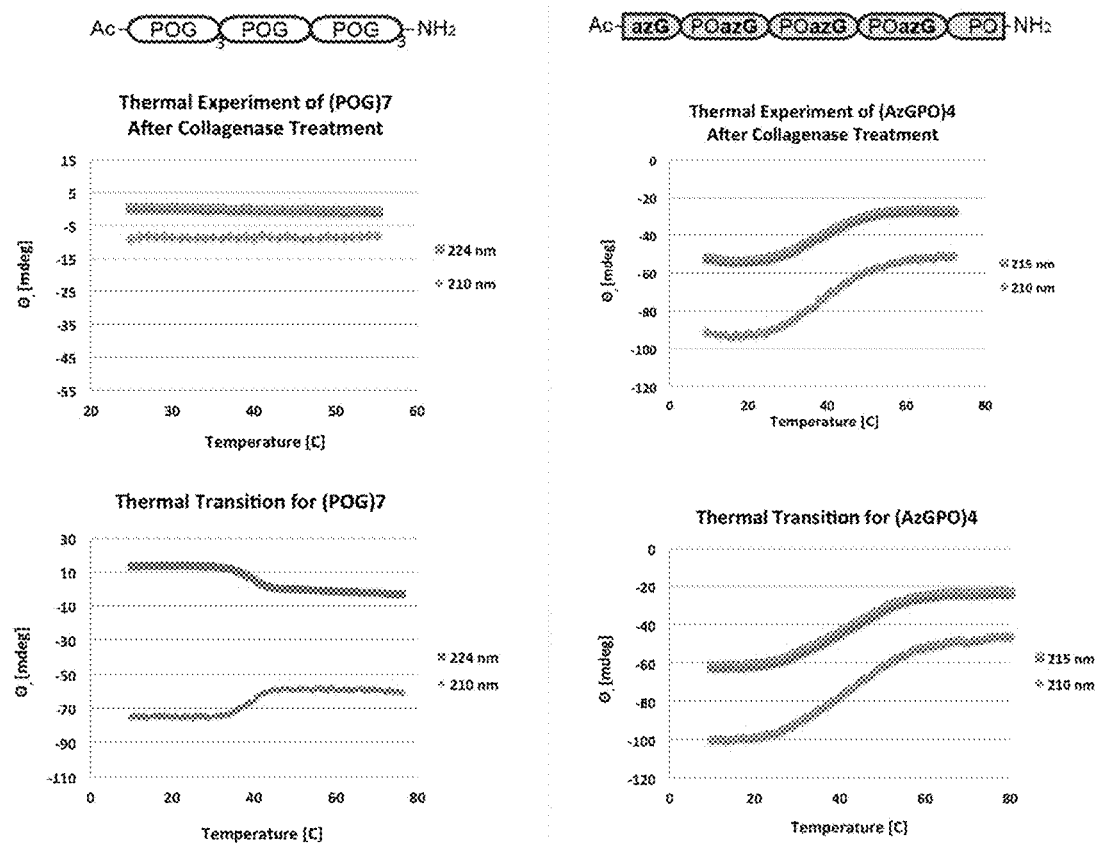

FIG. 35 shows CD thermal melting of both peptides after enzymatic reaction.

Figure 36:
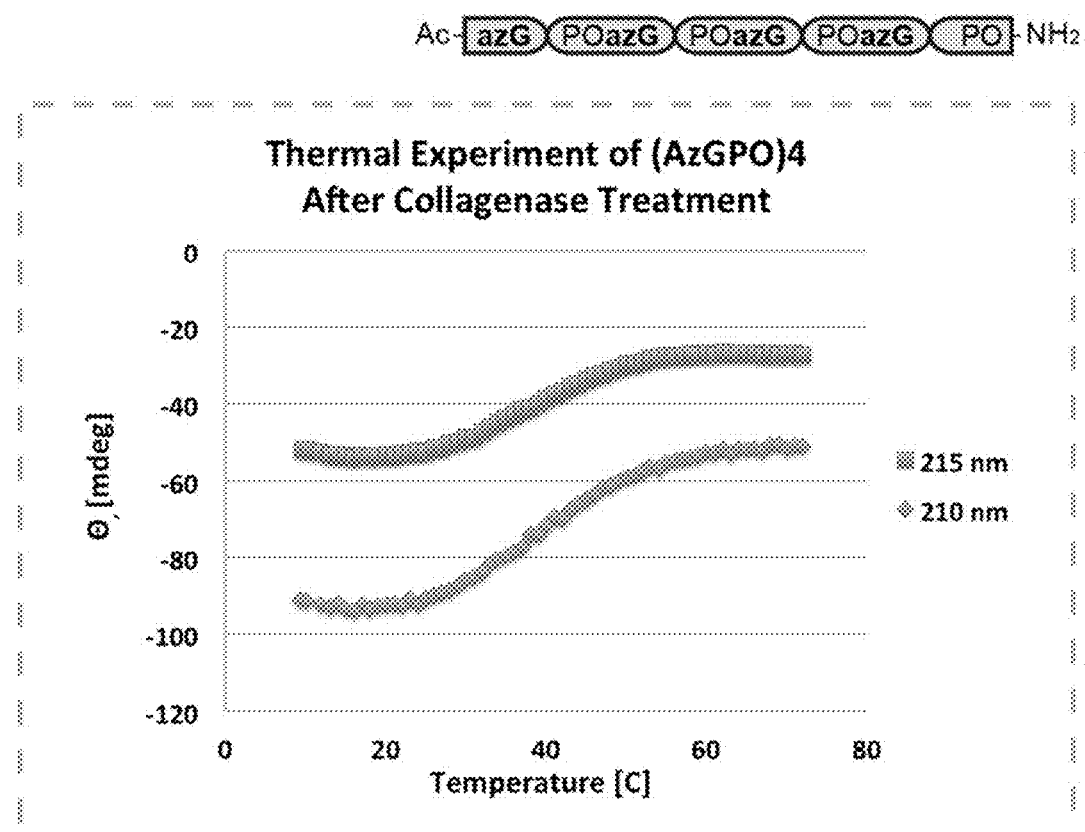
Figures 37A, 37B, 37C, 37D, 37E:
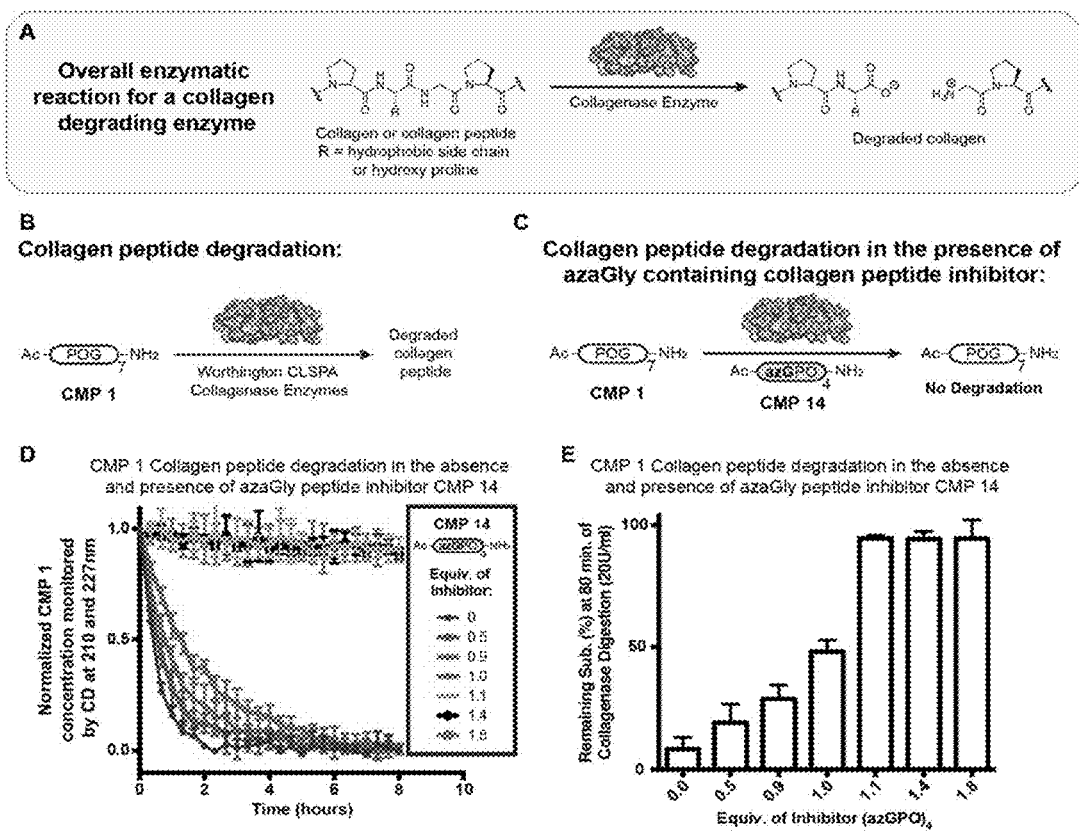

FIG. 36 shows the data for thermal experiment of (azGPO)4 after collagenase treatment.

FIG. 37A-FIG. 37E shows aza-glycine containing collagen mimics inhibit enzymatic digestion. A) General reaction scheme for enzymatic degradation of collagen by collagenase. B-C) A native collagen peptide sequence is rapidly degraded by collagenase, but this degradation is inhibited by the addition of an azapeptide collagenase inhibitor. D) Rate of enzymatic degradation of Ac-(POG)$_7$-NH$_2$ by collagenase is decreased as equivalence of Ac-(azGPO)$_4$-NH$_2$ is increased, reaching nearly quantitative inhibition at ≥1.1 eq. E) Percentage of substrate remaining following collagenase digestion determined by MALDI-TOF MS further supports the efficacy of Ac-(azGPO)$_4$-NH$_2$ as a collagenase inhibitor.

DETAILED DESCRIPTION OF THE INVENTION

I. Introduction

Figure 2:
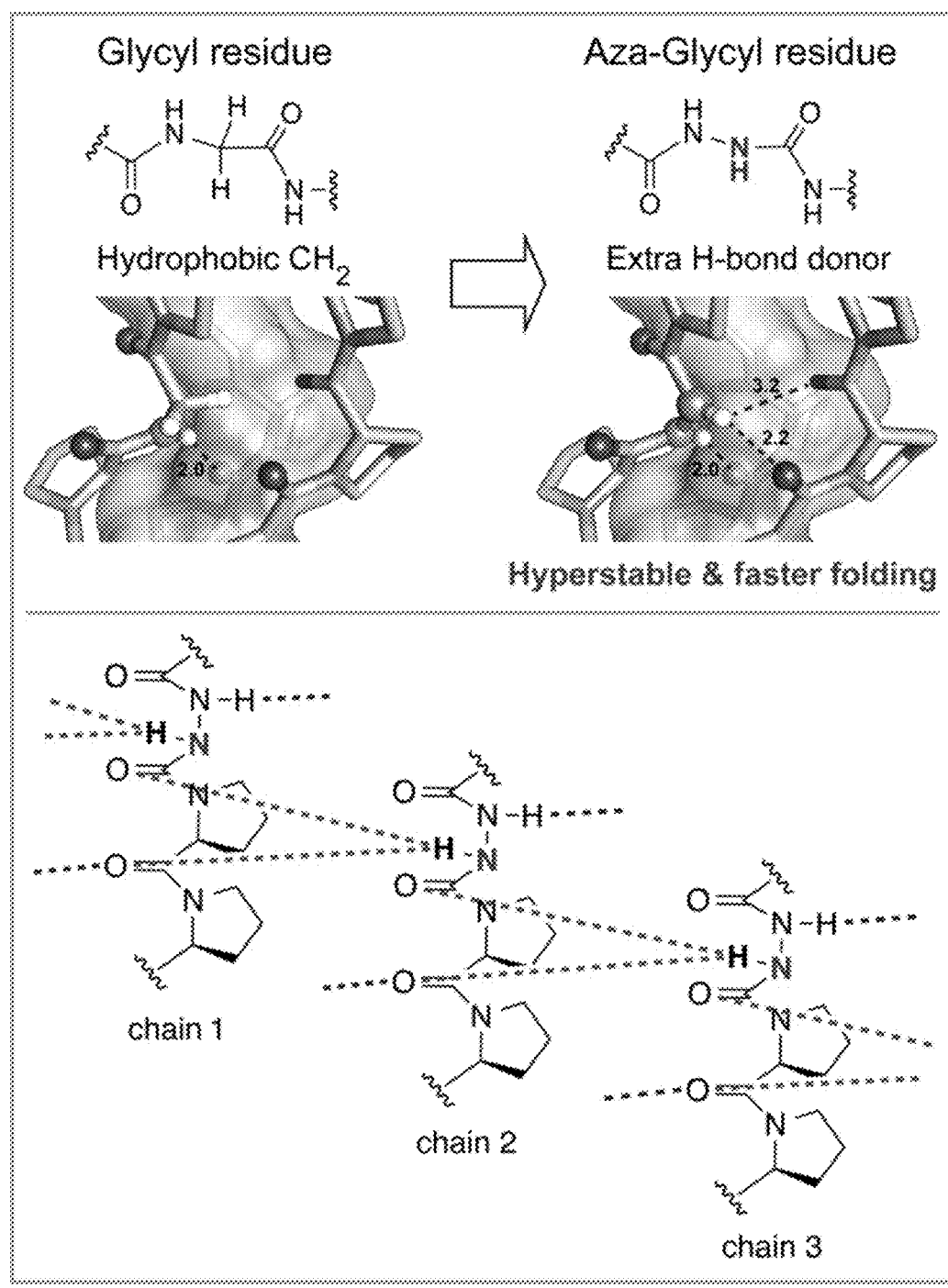
FIG. 2 shows the structure of glycyl versus aza-glycyl residues and how the substitution of aza-glycine for glycine introduces a new hydrogen bond donor to the collagen backbone. The bottom portion of FIG. 2 shows the hydrogen bond map of collagen containing the unnatural azGly modification. Natural collagen hydrogen bonds shown as blue dashed lines between strands. Proposed additional hydrogen bonds from azGly substitution shown as red dashed lines. AzGly N-atom shown in blue.

In one aspect, the present invention is directed to novel collagen peptides comprising aza-derivatized amino acids, generally either glycine or proline, resulting in aza-glycine containing collagen peptides and/or aza-proline containing collagen peptides. As is described herein, these aza-amino acid containing collagen peptides self-assemble into surprisingly stable structures, due apparently to the presence of the additional hydrogen bond contributed by the addition of the -aza secondary amine nitrogen in the glycine structure. When all three of the collagen monomers contain these additional amines and thus the additional hydrogen bonds as shown in FIG. 2, the resulting triplex is significantly more stable and has faster folding kinetics. Additionally surprising is that this stability is increased even when the aza-amino acids are placed at the termini of the collagen peptide, as in naturally occurring collagen triplexes there is some "breathing" of these ends.

Accordingly, the present invention provides novel collagen peptides, both in monomeric form as well as in self-assembled triplex forms, which are surprisingly stable.

Design of collagen mimetic peptides (CMPs) can be done either by modifying the side-chains of the peptides, the backbone of the peptides, or both. As noted above, while substitution of collagen peptides with unnatural amino acid side-chains had been a successful approach to collagen mimetic peptide design, prior attempts to modify the backbone of collagen peptides had largely been unsuccessful. In the present invention a strategy was developed for circumventing the current limitations in the field of collagen-protein interactions by using hyperstable collagen azapeptide technology.

Surprisingly, collagen peptides incorporating aza-amino acids (amino acids in which the α carbon of the backbone is replaced with a nitrogen) are able to self-assemble into collagen-like triple helical supramolecular structures. Moreover, similarly surprisingly, CMPs containing aza-amino acids show a number of hyperstability behaviors including but not limited to the unexpected stability at the terminal ends, and the ability to retain triple helical structure even with CMPs as short as 12 residues. These results are surprising because in naturally occurring collagens, longer peptides (at least 21 residues) are generally needed to achieve supramolecular stability.

Unexpectedly, azGly conferred a general stabilizing effect regardless of the position in the chain or the number of azGly incorporated. As a general rule, the further away the azGly substitution is from the center of the chain, the weaker the stabilizing effect is achieved. Conversely, single azGly substitution achieved the greatest stabilizing effect when the substitution is located at the center of the chain. Moreover, the stabilizing effect conferred by azGly also increased with the number of azGly residues incorporated.

Insofar as all collagen peptides have a strictly conserved glycine at every third position of the polypeptide chain, the ability to replace this conserved glycine with aza-glycine to enhance stability in a dose-dependent manner provides a generalized design principle to create collagen mimetic materials with tunable properties. The ease with which aza-amino acids can be integrated into small molecules and small peptides using standard synthetic methods is very advantageous. Aza-amino acids can be incorporated site specifically into natural peptides, creating a modular platform for the creation of highly customizable supramolecular biomaterials. Each of the biomedical applications of collagen peptides outlined benefit from the formidable stability, efficient self-assembly, and unique biocompatibility that collagen azapeptides provide. Aza-peptides are also less susceptible to proteolytic degradation and data showing that collagen aza-peptides are inert to collagenase degradation is included in Example 8.

Surprisingly, azPro conferred a selective stabilizing effect that is dependent on the position of the substitution in the chain, the identity of the neighboring non-conserved residue, and the number of azPro incorporated in the chain. As a general rule, azPro positioned at the Y position of the C-(X-Y-G)n-N 3-residue sequence motif, or when multiple azPro residues were incorporated, formation of triple helix was precluded. But when a single azPro was introduced at the X position, triple helical structure can still be obtained. In this position, placing a hydroxyproline next to the azPro greatly enhances the stability of the triple helical structure and improves the folding kinetics to almost native level.

Taken together, these facts form a set of design principles for CMPs with enhanced stability over naturally occurring collagen peptides. The surprising ability of the CMPs disclosed herein to self-assemble into stable triple helical structures enables the design of compositions, materials, and devices with properties and functions not previously available in the art.

Thus, the present invention solves the aforementioned long-standing problem in the art by providing novel backbone-modified collagen mimetic peptides (CMPs) that are capable of self-assembling into collagen-like triple helices as well as methods for designing and making the CMPs. The methods and CMPs disclosed herein may be used to formulate compositions and biomimetic materials and probes with a wide range of applications including to create collagen Homo- and Heterotrimeric Parallel Triple-helix mimics (HPT-mimics).

Accordingly, in a first aspect, the present invention provides CMPs containing one or more aza-amino acids (hereinafter referred to as aza-CMPs).

Aza-CMPs of the present invention will have the general formula of C-(X-Y-G)n-N where X and Y can be any amino acid and G can be Glycine or aza-Glycine, and n is an integer. The C and N terminals of the aza-CMP do not have to include a complete three-residue unit. They can be any of 1-3 residues of the (X-Y-G) triplet. For example, in the N-terminus, it may be R-(X-Y-G)-X-N, R-(X-Y-G)-X-Y-N, or R-(X-Y-G)-X-Y-G-N, where R represents the C-terminal portion of the peptide. Similarly, on the C-terminus, it may be C-G-(X-Y-G)-R, C-Y-G-(X-Y-G)-R', or C-X-Y-G-(X-Y-G)-R', where R' represents the N terminal portion of the chain.

It should be noted that while aza-CMPs of the present invention all have the surprising ability to form stable collagen-like triple-helical structure, they may differ in their secondary, tertiary, or quaternary structures, thermal stability, immunogenicity, biological interactions, enzymatic processing, as well as folding kinetics, each may find utilities in different settings. Thus, in some embodiments, the aza-CMPs may be found in monomeric form. In some other embodiments, the aza-CMPs may be found in self-assembled triple helical supramolecular complex.

Triple-helical complexes may be formed by peptides of three identical monomers (homo-trimers) or by different monomers (hetero-trimers). In hetero-trimers, not all three monomers of the triple helix need to be aza-CMPs. In some embodiments, only 1 or 2 monomers need to be aza-CMP while the remaining monomer(s) can be naturally occurring collagen peptide or a collagen peptide without backbone modification. In some other embodiments, at least one monomer can have different sequence and/or length from the other monomers.

Aza-amino acids suitable for the X and Y positions are preferably aza-Pro or aza-Gly. In general, the longer the aza-CMP, the more stable the resulting triple-helix is. Naturally occurring and synthetic triple helical collagens generally include peptides with 21 residues or longer, which is the shortest length that naturally occurring peptides will self-assemble. However, aza-CMPs of the present invention are able to form triple-helix with as few as 12 residues although shorter aza-CMPs may form triple helices at lower temperatures or in combination with previous side chain stabilizing residues. Thus, in a preferred embodiment, aza-CMPs of the present invention are preferably 12 residues or longer, more preferably from 12-21 residues or longer, including 12, 13, 14, 15, 16, 17, 18, 19 and 20 residues in length. It will be understood by those skilled in the art that the length of the aza-CMP is only limited by the synthesis technology, and thus peptides with longer lengths (greater than 21 residues, from at least about 25, 30, 35, 40, 45 or 50 or greater can be made.

Optionally, aza-CMPs of the present invention may also include one or more protein recognition sequences. Incorporation of a protein recognition sequence may find utility in strategic protein localization or site specific protein processing.

In a second aspect, the present invention provides compositions that incorporate one or more aza-CMPs described above. As noted above, aza-CMPs of the present invention are extremely versatile and may be used to construct a wide variety of materials such as hydrogels, structural scaffolds, and other hierarchical polymeric materials incorporating 1D, 2D, and 3D networks of aza-CMPs.

In 1D networks, aza-CMPs and their triple-helical complexes will generally be connected by a linear linker molecule and capped with telechelic end units.

In 2D networks, aza-CMPs and their triple-helical complexes will generally be connected by a "hub-like" connector molecule. The hub connector is preferably rigid and flat with linear protruding linkers having —COOH or —NH$_2$ functional groups at the distal end from the hub for connecting to an aza-CMP or any other reactive functional groups that facilitate connection.

In 3D networks, aza-CMPs and their networks will generally be connected by a 3D hub connector molecule with linear protruding linkers having —COOH or —NH$_2$ functional groups at the distal end from the hub. Alternatively, 3D networks may be a combination of 1D and 2D networks, which will generally be in the form of a diamond lattice. In linking together 1D and 2D networks, the addition of a linking agent may be optionally used such that the 3D network may behave like an epoxy.

In a third aspect, the present invention also provides methods for making the aza-CMPs and compositions described above.

In the present invention, it was unexpectedly discovered that the use of Proline-Hydroxyproline-Glycine (POG) tripeptide as a synthon in solid-phase peptide synthesis resulted in greater efficiency, higher yield, and lower number of reaction steps per synthesis. Accordingly, aza-CMPs of the present invention are preferably synthesized using solid-phase peptide synthesis but can also be accessed by solution phase or polymerization methods. In a preferred embodiment, methods for synthesizing an aza-CMP will generally having the steps of providing a POG tripeptide synthon and a solid support with a first protected amino acid or peptide synthon attached to the solid support; deprotecting the first protected amino acid or peptide synthon; coupling a second peptide synthon or an amino acid to the deprotected peptide synthon or amino acid; repeating the process until the desired aza-CMP sequence is completed; and cleaving the completed aza-CMP from the solid support.

The above described aza-CMPs and compositions of the present invention have applications in a wide range of settings, including but not limited to imaging agents, research tools, biomaterials for wound treatment, hydrogel matrices, microspheres, substrates for attachment of functional molecular entities, mini-proteins for therapeutic applications, peptidomimetics for therapeutic applications and numerous others. Hence, in a fourth aspect, the present invention is directed to methods, material constructs, and devices that utilize the aza-CMPs and compositions described above.

The various aspects and embodiments of the present invention offer many advantages. The synthetic method for making the aza-CMPs of the present invention is scalable, inexpensive and compatible with existing manufacturing setup, thus, making the technology easy to adopt in a commercial setting. The general stability enhancing nature of aza-Gly substitution provides a very useful tool for creating short, stable collagen mimetic peptides that were previously impossible to do. The tunable nature of the peptide properties and the ability to create hierarchical materials also opens the door to numerous previously difficult or impossible biomedical applications.

Other aspects and advantages of the present invention will be apparent from the following detailed descriptions, drawings, and the appended claims.

2. Definitions

Unless otherwise indicated, all terms used herein have the meanings given below, and are generally consistent with same meaning that the terms have to those skilled in the art of the present invention. All publications cited herein are expressly incorporated herein by reference for the purpose of describing and disclosing compositions and methodologies that might be used in connection with the invention.

As used herein, an "amino acid" or "amino acid residue" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; a-methyl-alanine; para-benzoylphenylalanine; phenylglycine; propargylglycine; sarcosine; and tert-butylglycine). The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a (C1-C6)alkyl, phenyl or benzyl ester or amide). Other suitable amino and carboxy protecting groups are known to those skilled in the art (See for example, T. W. Greene, Protecting Groups In Organic Synthesis; Wiley: New York, 1981; D. Voet, Biochemistry, Wiley: New York, 1990; L. Stryer, Biochemistry, (3rd Ed.), W. H. Freeman and Co.: New York, 1975; J. March, Advanced Organic Chemistry, Reactions, Mechanisms and Structure, (2nd Ed.), McGraw Hill: New York, 1977; F. Carey and R. Sundberg, Advanced Organic Chemistry, Part B: Reactions and Synthesis, (2nd Ed.), Plenum: New York, 1977; and references cited therein). According to the invention, the amino or carboxy protecting group can also comprise a radionuclide (e.g., Fluorine-18, Iodine-123, or Iodine-124).

The term "amino acid" specifically include the amino acid analogs aza proline and aza glycine as outlined herein.

As used herein, a "peptide" is a sequence of 2 to 25 to 50 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

The term "polypeptide" refers to a biopolymer compound made up of a single chain of amino acid residues linked by peptide bonds. The term "protein" as used herein may be synonymous with the term "polypeptide" or may refer, in addition, to a complex of two or more polypeptides.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless The terms "residue" or "amino acid residue" or "amino acid" are used interchangeably herein to refer to an amino acid that is incorporated into a protein, polypeptide, or peptide (collectively, "protein"). The amino acid may be a naturally occurring amino acid and, unless otherwise limited, may encompass known analogues of natural amino acids that can function in a similar manner as naturally occurring amino acids.

3. Collagen Structure

As is known in the art, the collagen protein is a trimeric protein structure, comprising a triple helix of three collagen monomers (sometimes referred to as a "triplex"). The most common motifs in the amino acid sequence of naturally occurring collagen are amino acid triplets of glycine-proline-X and glycine-X-hydroxyproline, where X is any amino acid other than glycine, proline or hydroxyproline. However, some of the synthetic collagen structures herein rely on combinations of proline, hydroxyproline and glycine, with aza-glycine or aza-proline included as outlined herein. The glycine occurring at every third position of the chain is strictly conserved. The other two residues of the tripeptide unit may be any amino acid. In fact, the sequence variability in these two is what gives rise to the various different forms of collagen.

The triplex stability comes from the steric repulsion of the pyrrolidine rings of proline and hydroxyproline, and the hydrogen bonding between the —NH groups of the glycine residues (hydrogen bond donor) and the CO groups on other chains (acceptors), with the —OH group of hydroxyproline also contributing to hydrogen bonding. Glycine is also important in that the assembly of the triple helix puts these residues in the interior (axis) of the helix, where there is no space for a larger side group.

As is known in the art, the shortest peptide of collagen monomers that will self-assemble into the trimeric helix structure is 21 amino acids, generally thought of as seven distinct amino acid triplets. Accordingly, in some embodiments, the present invention provides collagen monomers that are at least 21 amino acids in length, in general comprising at least seven amino acid triplets. By "collagen monomer" (sometimes referred to in the art as tropocollagen) herein is meant a peptide that will self-assemble with two other collagen monomers into a collagen triple helix (or "triplex"). Tropocollagen variants can contain one or more aza-glycine or aza-proline. In hetero-trimers, not all three tropocollagens of the triple helix need to be aza-CMP tropocollagen variants. In some embodiments, 1, 2 or 3 are a aza-CMP tropocollagen variant while the remaining tropocollagen(s) can be naturally occurring collagen peptide or a collagen peptide without backbone modification. In some other embodiments, at least one monomer can have different sequence and/or length from the other tropocollagen variants. A number of useful collagen monomers are depicted throughout.

Accordingly, the present invention provides collagen peptides that are at least about 21 amino acids in length (21mer), with 21 amino acid lengths finding particular use in many embodiments, with 22 and 23 amino acids also finding use in the present invention.

Longer monomers, generally but not always in extensions of three amino acids (amino acid triplets), can also be used. The length of these collagen monomers is essentially only limited by the ease, ability and cost of chemically synthesizing the monomers. Thus, preferred total lengths of the collagen monomers is $[(AA)_3]_n$, where n is from 7 to about 50, with 7, 8, 9, 10, 11, 12, 13, 14, 15, 16, 17, 18, 19, 20 all finding use in particular embodiments. As for the 21mers, these higher lengths can include one or two extra amino acids, for example AA-$[(AA)_3]_n$, AA-AA-$[(AA)_3]_n$, AA-AA-$[(AA)_3]_n$-AA, AA-$[(AA)_3]_n$-AA and AA-AA-$[(AA)_3]_n$-AA-AA all finding use in some embodiments, as well as higher analogs. AA in this case refers to Amino Acid. By "amino acid" herein is meant any of the naturally occurring amino acids, including hydroxyproline, as well as non-naturally occurring amino acids, generally in the L-enantiomer formation, although in some cases, the D-form can be used. For example, the inclusion of one or more D-forms is also possible.

As discussed herein, while other amino acids can be used, amino acid triplets of particular use in some embodiments comprise only two prolines ("P"; including hydroxyproline, "O") and one glycine ("G", including aza-glycine ("azG" or "azG"). Accordingly, useful triplets include GPP, GPO, GOP, PGP, PGO, OGP, POG, PPG, OPG, with at least one of the triplets of the monomer including an azG as outlined below.

As further described below, one of the AA residues in these formulas is an aza glycine or aza-proline residue as outlined herein, with aza-glycine residues finding use.

In addition, the individual monomers of the triplexes of the invention can be the same length or different lengths. In some embodiments, when larger self-assembling structures are desired, mixtures of different monomer lengths can result in ends (termini) that are free to interact with additional monomers, analogous to the "sticky ends" of nucleic acids.

4. Collagen Mimetic Peptides Incorporating Aza-Amino Acids (Aza-CMPs)

While not intending to be bound by any particular theory, it is believed that the enhanced stability of the aza-CMPs as compared to naturally occurring collagen peptides of the same sequence is due to the presence of the additional hydrogen bond contributed by the addition of the -aza secondary amine nitrogen in the glycine structure. As illustrated in FIG. 2, molecular modeling studies show that when all three strands of the collagen peptides contain aza-amino acids, the additional hydrogen bonds renders the resulting triplex significantly more stable and faster folding kinetics. Experimental findings disclosed herein below further illustrate the general design principles of aza-amino acid collagen mimetic peptides.

As is also known in the art, the shortest peptide of collagen monomers that will self-assembled into the trimeric helix structure is 21 amino acids, generally thought of as seven distinct tripeptide units. While longer collagen peptides tend to be more stable, they also introduces more complicated interactions and are more difficult to synthesize. Therefore, finding shorter peptides that will self-assemble into collagen-like triple helix supramolecular complex has been a challenge in the art. As noted above, it is an unexpected discovery of the present invention that CMPs as short as 12 residues will self-assemble into triple helix with the incorporation of aza-amino acids.

Accordingly, in some embodiments, the present invention provides aza-CMPs containing one or more aza-amino acids. Aza-CMPs of the present invention will have the general formula of C-(X-Y-G)n-N where X and Y can be any amino acid and G can be Glycine or aza-Glycine, and n is an integer. The C and N terminals of the aza-CMP do not have to include a complete three-residue unit. They can be any of 1-3 residues of the (X-Y-G) triplet. For example, in the N-terminus, it may be R-(X-Y-G)-X-N, R-(X-Y-G)-X-Y-N, or R-(X-Y-G)-X-Y-G-N, where R represents the C-terminal portion of the peptide. Similarly, on the C-terminus, it may be C-G-(X-Y-G)-R', C-Y-G-(X-Y-G)-R', or C-X-Y-G-(X-Y-G)-R', where R' represents the N terminal portion of the chain.

It should be noted that while aza-CMPs of the present invention all have the surprising ability to form stable collagen-like triple-helical structure, they may differ in their secondary, tertiary, or quaternary structures, thermal stability, immunogenicity, as well as folding kinetics, each may find utilities in different settings. Thus, in some embodiments, the aza-CMPs may be found in monomeric form. In some other embodiments, the aza-CMPs may be found in self-assembled triple helical supramolecular complex.

Triple-helical complexes may be formed by peptides of three identical monomers (homo-trimers) or by different monomers (hetero-trimers). In hetero-trimers, not all three monomers of the triple helix need to be aza-CMPs. In some embodiments, only 1 or 2 monomers need to be aza-CMP while the remaining monomer(s) can be naturally occurring collagen peptide or a collagen peptide without backbone modification. In some other embodiments, at least one monomer can have different sequence and/or length from the other monomers.

Aza-amino acids suitable for the X and Y positions are preferably azPro or azGly. In general, the longer the aza-CMP, the more stable the resulting triplex is. Naturally occurring collagens generally include peptides with 21 residues or longer. However, aza-CMPs of the present invention are able to form triple-helix with as few as 12 residues. Thus, in a preferred embodiment, aza-CMPs of the present invention are preferably 12 residues or longer, more preferably from 12-21 residues, including 12, 1,34 1,4 15, 16, 17, 18, 19 and 20, with higher numbers allowed as well, generally only limited by synthetic methods.

Longer monomers, generally but not always in extensions of three amino acids (amino acid triplets), can also be used. The length of these aza-CMP monomers is essentially only limited by the ease, ability and cost of chemically synthesizing the monomers. Thus, preferred total lengths of the aza-CMP monomers is $[(AA)_3]_n$, where n is from 4 to about 50, with 7, 8, 9, 10, 11, 12, 13, 14, 15, 16, 17, 18, 19, 20 all finding use in particular embodiments. As noted above, longer length aza-CMPs are only limited by the synthesis technology used.

As for the 21mers, these higher lengths can include one or two extra amino acids, for example AA-$[(AA)_3]_n$, AA-AA-$[(AA)_3]_n$, AA-AA-$[(AA)_3]_n$-AA, AA-$[(AA)_3]_n$-AA and AA-AA-$[(AA)_3]_n$-AA-AA all finding use in some embodiments. AA in this case refers to Amino Acid. By "amino acid" herein is meant any of the naturally occurring amino acids, including hydroxyproline, as well as non-naturally occurring amino acids, generally in the L-enantiomer formation, although in some cases, the D-form can be used. For example, the inclusion of one or more D-forms can prevent trimerization. It will also be understood by those skilled in the art that each AA within the repeating $(AA)_3$ unit can be independently chosen and do not have to be all the same.

While aza-substitution can potentially be made at any position of a CMP chain, and the X and Y position of the tripeptide motif can potentially be any amino acid, the G position is generally conserved if formation of triple helix is desired. In a preferred embodiment, aza-CMPs preferrably include only azGly, in other preferred embodiment, aza-CMPs preferrably include only azPro, in still other preferred embodiment, aza-CMPs preferrably include a mix of azGly and azPro. Thus, useful triplets include GPP, GPO, GOP, PGP, PGO, OGP, POG, PPG, OPG, with at least one of the triplets of the monomer including an azGly as outlined below.

4.1 azGly Collagen Peptides

The structure of aza-glycine (sometimes abbreviated herein as "azGly" or "azG" is shown in FIG. 2.

As will be appreciated by those in the art, the placement of the azGly within the collagen monomer peptide can vary. In some cases, it is in an "internal" position, e.g. not on either the N- or C-terminus of the peptide monomer (although as described herein, there can be additional groups on the termini that are not amino acid derived). For example, in the case of a 21mer, the azGly can be in the center triplet $((AA)_3$-azG-AA-AA-$(AA)_3$, $(AA)_3$-AA-azG-AA-$(AA)_3$ or $(AA)_3$-AA-AA-azG-$(AA)_3$, for example. Alternatively, the azGly can be at a peptide terminus (again, there can be additional groups on the termini that are not amino acid derived). Stated differently, when the collagen monomer comprises only proline (including hydroxyproline) and glycine, suitable azG-triplets are selected from the group consisting of azGPP, azGPO, azGOP, PazGP, PazGO, OazGP, POazG, PPazG and OPazG.

It should be noted that most of the structures herein depict triplets of proline, hydroxyproline and glycine in various combinations. However, as will be appreciated by those in the art, additional amino acids can be included in the structures of the invention, as long as the ability to self-assemble into triplexes is not destroyed. Thus, for example, in some embodiments, different amino acids (including both naturally occurring and non-naturally occurring) may be used in a site specific way to allow for chemical attachment of additional moieties, as outlined below for chromophore attachment.

In one embodiment, the collagen monomers have an amino acid triplet with the structure below, where the azGly is in the "first position" of the triplet:

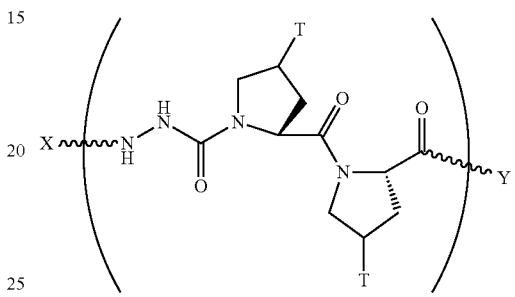

In one embodiment, the collagen monomers have an amino acid triplet with the structure below, where the azGly is in the "second position" of the triplet:

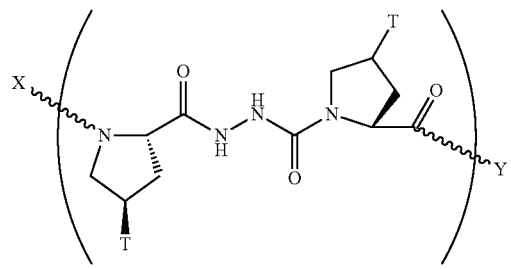

In one embodiment, the collagen monomers have an amino acid triplet with the structure below, where the azGly is in the "third position" of the triplet:

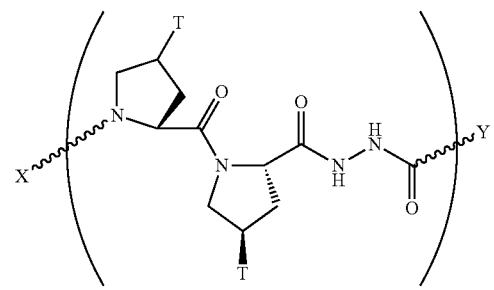

In these structures, T is independently selected from —OH (e.g. hydroxyproline) or —H (proline). In all structures outlined herein, there may be additional unlabeled hydrogen atoms. That is, when T is hydrogen, there is actually a second hydrogen on the carbon atom for a valency of 4. X and Y are independently selected from peptides including amino acid triplets (including those with azGly in the triplet, forming collagen monomers with more than one azGly, as outlined below) and other chemical functionalities as needed.

Additional aza-tripeptide structures are shown in FIG. 26 and FIG. 27. Again, these structures depict proline and hydroxyproline as the other amino acids in the triplet, but one of these may be substituted with a different amino acid.

In some embodiments, the aza-CMP monomers can include additional azGly residues to form monomers with two or more azGly residues, as is more fully described herein.

In many embodiments, the invention provides compositions of three collagen monomers, generally referred to herein as "first, second and third" monomers, that are self-assembled into a triplex formation. Again, as discussed herein, these monomers may be identical or different, including differences in length, azG position within the chain and/or in number of azGly residues. In some embodiments, the azG position is the same in each monomer. In some embodiments, collagen monomers containing both azG residues as well as other azAAs, such as azP and azO, can be used as well.

4.2 azGly as a General Aza-CMP Design Element

As will be appreciated by those in the art, there are a wide variety of potential uses for the aza-CMP monomers and the trimeric complexes of the invention, due to their increased stability. Collagen is the main structural protein in the animal kingdom and is the most abundant protein in mammals (accounting for 25-35% protein content in body). Collagen occurs in tendons, ligaments, skin, finger- and toenails, corneas, lens, cartilage, bones, blood vessels, the gut, intervertebral discs, dentin in teeth, muscle (endomysium), cardiac valve rings, central heart body, cardiac skeleton and the extracellular matrix.

Accordingly, the azGly and azPro collagen monomers and the corresponding trimeric complexes of the invention, particularly the increased stability azGly collagen monomers, find use in bone grafts, cosmetic surgery, cosmeceuticals such as skin fillers, burn surgery and treatment, tissue regeneration, reconstructive surgery, wound care management, and as scaffolds for cell growth for grafts (e.g. bioengineering). For example, collagen has been used as implantable carriers for bone inducing proteins or as bone substitutes due to its osteoinductive activity. Similarly, the collagen peptides of the invention can be used in the construction of artificial skin substitutes (sometimes used with silicones, glycosaminoglycans, fibroblasts, growth factors and other substances). Similarly, collagen films can be made for use as barrier membranes, for example in conjunction with drugs that are loaded into or onto collagen membranes to deliver drugs to the eyes and over wounds. Collagen sponges are used in the treatment of severe burns and as a dressing for many kinds of wounds including pressure and bed sores, leg ulcers, donor sites of skin, etc.

The enhanced stability conferred by azGly was unexpectedly discovered in the present invention to be a general property, meaning that azGly substitution will result in enhanced stability no matter which Gly position along the monomer chain or number of Gly's replaced. This finding enables incorporation of destabilizing modifications because the destablizing effect may potentially be balanced out by introducing one or more azGly substitutions. Thus, aza-CMPs having comprising three peptide repeats of XaaYaaAzaGly where Xaa and Yaa can be any natural or unnatural amino acid are all possible. Moreover, tripeptide monomers having the general structure XaaYaaAzaGly wherein Xaa and Yaa can independently be any natural or unnatural amino acid may be polymerized to form longer peptides.

4.3 Aza-Proline as a Supplemental Aza-CMP Design Element

As noted above, azPro's stailizing effect on the triple helical complex is selective, depending on where it is located and what neighboring residues are present. Thus, azPro may serve as a supplemental design element in tuning the properties of aza-CMPs.

The structure of aza-proline (sometimes abbreviated herein as "azPro" or "azP" is shown in FIG. 14.

As will be appreciated by those in the art, the placement of the azPro within the collagen monomer peptide can vary. In some cases, it is in an "internal" position, e.g. not on either the N- or C-terminus of the peptide monomer (although as described herein, there can be additional groups on the termini that are not amino acid derived). For example, in the case of a 21mer, the azPro can be in the center triplet $((AA)_3\text{-azP-AA-AA-}(AA)_3$, $(AA)_3\text{-AA-azP-AA-}(AA)_3$ or $(AA)_3\text{-AA-AA-azP-}(AA)_3$, for example. Alternatively, the azPro can be at a peptide terminus (again, there can be additional groups on the termini that are not amino acid derived).

Similar to above, when the collagen monomer comprises only proline (including hydroxyproline) and glycine, suitable azP-triplets are selected from the group consisting of azPPG, azPGP, azPGO, PazPG, OazPG, GazPO, GazPP, GPazP, GOazP, OGazP and PGazP.

It should be noted that most of the structures herein depict triplets of proline, hydroxyproline and glycine in various combinations. However, as will be appreciated by those in the art, additional amino acids can be included in the structures of the invention, as long as the ability to self-assemble into triplexes is not destroyed. Thus, for example, in some embodiments, different amino acids (including both naturally occurring and non-naturally occurring) may be used in a site specific way to allow for chemical attachment of additional moieties, as outlined below for chromophore attachment.

Accordingly, in some further embodiments, aza-CMPs of the present invention may also include one or more protein recognition sequence. Methods for making such aza-CMPs and their uses are further described below.

5. Synthesis of Aza-CMPs

Ideally, methods for producing aza-CMPs should preferably have the characteristics of easy to scale-up, inexpensive, and capable of high purity yield. While aza-CMPs may be manufactured with any methods known in the art, the present invention provides a method that is particularly efficient in making aza-CMPs.

In the present invention, it was surprisingly discovered that the use of Proline-Hydroxyproline-Glycine (POG) tripeptide as a synthon in solid-phase peptide synthesis resulted in greater efficiency, higher yield, and lower number of reaction steps per synthesis. Accordingly, aza-CMPs of the present invention are preferably synthesized using solid-phase peptide synthesis.

In a preferred embodiment, methods for synthesizing an aza-CMP will generally have the steps of providing a POG tripeptide synthon and a solid support with a first protected amino acid or peptide synthon attached to the solid support; deprotecting the first protected amino acid or peptide synthon; coupling a second peptide synthon or an amino acid to the deprotected peptide synthon or amino acid; repeating the process until the desired aza-CMP sequence is completed; and cleaving the completed aza-CMP from the solid support.

Reaction conditions, suitable solid support, protection groups and coupling chemistry are known in the art and as described below in the Examples.

6. Design and Uses of Biomimetic Collagens Containing Aza-CMPs

The above described aza-CMPs may be used to formulate compositions and materials useful in any number of applications, including but not limited to imaging agents, research tools, biomaterials for wound treatment, research tools, hydrogel matrices, microspheres, substrate for attachment of functional molecular entities, and numerous others. Hence, some embodiments of the present invention also provide methods, material constructs, and devices that utilize the aza-CMPs and compositions described above.

Aza-CMPs of the present invention are extremely versatile and may be used to construct a wide variety of materials such as hydrogels, structural scaffolds, and other hierarchical polymeric materials incorporating 1D, 2D, and 3D networks of aza-CMPs (see FIGS. 28-30).

In 1D networks, aza-CMPs and their triple-helical complexes will generally be connected by a linear linker molecule and capped with telechelic end units. Exemplary linear linker molecule may include a poly(ethylene glycol) (PEG) linker having the general formula H—(O—CH$_2$—CH$_2$)$_n$—OH, where n can be any integer but is preferably a small number below 10, more preferably below 5. Linkers can be aliphatic, PEG, or any common linker structure and may also include embedded functionality. Exemplary telechelic end units may be any known telechelic ends or host-guest pair known in the art.

In 2D networks, aza-CMPs and their triple-helical complexes will generally be connected by a "hub-like" connector molecule. The hub connector is preferably rigid and flat with linear protruding linkers having —COO or —NH$_2$ functional groups at the distal end from the hub for connecting to an aza-CMP. Exemplary 2D hub connectors may include any appropriately substituted aromatic or saturated ring systems or branched aliphatic systems. Exemplary linear linkers may include but not limited to 1,3,5-substituted benzene ring systems.

In 3D networks, aza-CMPs and their networks will generally be connected by a 3D hub connector molecule with linear protruding linkers having —COO or —NH$_2$ functional groups at the distal end from the hub. Exemplary 3D hub connector molecule are preferably multi-branched connectors containing 3 or more arms. Example 3D hub connectors may include but not limited to tetra-substituted carbon connectors and substituted adamantane derivatives that present a rigid 4-arm tetrahedral arrangement as connecting points. Exemplary linear protruding linkers may include but not limited to PEG and aliphatic connectors. Alternatively, 3D networks may be a combination of 1D and 2D networks, which will generally be in the form of a diamond lattice. In some embodiments, linking together 1D and 2D networks may require the addition of a linking agent. In such embodiments, the 3D network may behave like an epoxy.

Materials constructed using aza-CMPs of the present invention find numerous uses in medical, dental, pharmaceutical, and other areas.

In one exemplary embodiment, the present invention provides an imaging agent. Collagen is present in many areas of the human body. Short aza-CMPs capable of binding and integrating into specific locations such as defect sites or undergo strand invasion may offer opportunity for disease diagnosis or use in fundamental biology. Short aza-CMPs with fluorophores may be attached to dyes for use as imaging agents. Imaging tumor microenvironments presents another application of such imaging agents or tracking extracellular matrix remodeling. Such imaging agents may also find use for enhanced contrast in imagining the anatomy of joints, tendons, cartilage, etc.

In another exemplary embodiment, the present invention also provides a substrate for a scratch assay. Such substrate will provide a superior matrix for cell growth that is less susceptible to degradation by collagenases and secreted matrix metalloproteins.

In another exemplary embodiment, the present invention also provides a substrate for a cell migration assay. Collagens are often used as or components of 3D cell culture media and the use of aza-CMPs will have the benefits that they are more stable and less prone to enzymatic degradation.

In another exemplary embodiment, the present invention also provides a combinatorial library of aza-CMPs. Members of such a library may include a plurality of peptides with aza-amino acids incorporated at various positions of the peptides in a combinatorial scheme. Those skilled in the art will recognize that the combinatorial scheme is not particularly limited but may be chosen depending on the purpose for the library.

In another exemplary embodiment, the present invention also provides a system for screening and analyzing molecular recognition. Systems in accordance with this embodiment will generally include one or more aza-CMP having a target recognition sequence to be analyzed for molecular recognition. Proteins or other molecules to be tested for recognition of the target sequence may be brought in contact with the target sequence. Depending on the interaction to be analyzed, a suitable detection device or method may also be included. Protein recognition sequences are preferably selected from a collagen protein recognition sequence. Examples of recognition sequences may include integrin recognition sequence, von Wildebrand Factor binding sequences, and other sequences known in the art. Other examplary sequences that are known to be relevant in mechanobiology of collagens may include those listed in Table 1 as well as integrin and matrix metalloprotein sequences.

In another exemplary embodiment, the present invention also provides methods and tools for treating a skin wound. In some embodiments, skin wounds may be treated by applying a wound dressing that utilizes aza-CMP as a dressing material. The aza-CMP may be pre-seeded with any known or future discovered wound healing factors such as growth factors including but not limited to VEGF, FGF, PDG, etc. Other components that may be used to form a device for wound healing may include integrin and or endoethlial cells.

In some embodiments, chronic wounds may be treated by applying aza-CMP. There are a vast number of collagen-protein interactions and a comprehensive structural and biophysical analysis of the collagen interacome will thus be distinctly useful in the design of novel therapies for human health such as chronic wound healing. As an example, over six million Americans suffer annually from complications of either chronic wounds or pathologic dermal scarring, with an associated health care cost exceeding $35 billion. Despite significant advances in wound care, the therapeutic challenge of chronic wounds has increased due to an expanding at-risk aging population and associated common geriatric comorbidities, such as diabetes and peripheral vascular disease. The development of new collagen-protein interaction modulators will contribute to a better understanding of the collagen interactome pathways, helping to address many of the problems outlined above. Support for novel research efforts such as those outlined in this proposal will be critical. Recent results from our laboratory show that a simple synthetic modification to collagen peptides results in extra hydrogen bonding and dramatic improvements in the properties of higher order collagen peptide assembly. As such, these novel hyperstable peptides open new possibilities for the design of novel and robust collagen-protein interaction modulators and chemical tools to aid in the development of novel therapeutics.

In another exemplary embodiment, the present invention also provides a chromophore assembly having an aza-CMP scaffold that precisely controls excitonic states in the chromophores. Aza-CMPs useful as scaffolds in this embodiment may further include functionalizable side-chain via the hydroxyl group of the hydroxyproline residue. Suitable side-chains may be an aliphatic linker. Chromophores that may be attached to the scaffold are preferably organic chromophores or fluorophores.

In still another exemplary embodiment, the present invention also provides a hydrogel microsphere useful for delivering a molecular payload. The hydrogels may optionally be functionalized molecular recognition moieties to facilitate interaction with biological targets. Those skilled in the art will recognize that any payload that may be loaded with conventional hydrogel microsphere may be used together with aza-CMP microspheres of the present invention and benefit from the unique properties of the microspheres of the present invention.

In yet another exemplary embodiment, the present invention provides a pair of crystal structures for homotrimers of (Pro-Hyp-Gly)$_3$-Pro-Arg-Gly-(Pro-Hyp-Xaa)$_4$-NH$_2$ where Xaa is Gly in one crystal and aza-Gly in another crystal. This pair of crystal structures is useful in aiding the design and modeling of other aza-CMPs that may form triple helical supramolecular complexes.

Given the importance of biocompatibility and robustness for biomaterials, it will be useful to assess the mechanical integrity of the collagen azapeptides. This may be accomplished in part by electrospinning the peptides into fibers. Upon preparation, these fibers may be analyzed in terms of ultimate tensile strength (UTS) and yield strength. Furthermore, the secondary structure of these peptide fibers may be characterized using CD spectroscopy. This information will provide insight on how these peptides will self-assemble in vivo as compared to non-azapeptide collagenous sequences. Given that stable fibril formation is a staple of collagen peptide functionality, this property could be a crucial distinguishing factor for these novel azapeptides.

The collagen azapeptide hydrogels designed and fabricated as described above may be further characterized in terms of their influence on cell migration. By analyzing an array of collagen hydrogels in parallel, the influence of a wide range of collagen azapeptides on the mechanobiology of cells in 3D culture may be indexed. For example, by spreading the hydrogels into a standard culture plate, the biocompatibility of the hydrogels may be assessed using cell culture assays. Treating the hydrogels with bacterial and mammalian collagenases such as C. histolyticum and matrix metalloproteinases (MMPs) or enzymes such as trypsin will provide valuable insight into their ability to resist premature degradation. Monitoring changes in the rate of enzymatic or bacterial degradation in relation to the type of azapeptide used to synthesize the hydrogel, for example, would indicate how to use the number and position of azGly substitutions in the sequence to tune the degradation rate of the overall material properties.

Similarly, by seeding stem cells onto the surface of these hydrogel culture plates, the influence of the hydrogels on cell development may be assessed. Cell viability and proliferation assays may be conducted using normal human adipose-derived mesenchymal stem cells (MSCs) (ATCC PCS-500-011) based on standard procedures known in the art. Previous work in this area has focused on the integration of binding sequences for biomolecules such as integrins and endothelial cells to promote wound healing specific to the site of implantation and these same binding sequences may be integrated into collagen peptide materials of the present invention. This will enable prediction of cell viability at the cell-hydrogel interface in vivo.

In addition to the properties of controlled degradation and bioactivity discussed above, a high-throughput scratch assay may provide a model for the self-healing properties of the hydrogels. A rough approximation of a general in vivo hydrogel environment for the cells may be created by preparing a hydrogel culture plate and seeding the gels with mesenchymal stem cells (MSCs). This experimental model may be scaled for high-throughput analysis, for example, by plating different hydrogels in each well of a 96- or 384-well microplate. By uniformly scraping each cell-coated hydrogel assembly with a 96- or 384-pin scratcher to disrupt their distribution atop the hydrogel, a "wound" may be introduced to the matrices. This will allow monitoring of the rate at which the cells migrate to their previous distribution and "heal" the wounds in each system. By comparing hydrogels of varying peptide composition, useful information about how azapeptides may alter the process of cell migration may be gathered. Addition of different collagen protein recognition sequences and protein factors will allow further tuning of the bioactivity of these hydrogels.

In another exemplary embodiment, the present invention also provides for advances in PPI regulation and modulation. Interactions between proteins and collagen are many in number and far from uniform. Many important proteins interact with collagen through characteristic binding sequences, but in the case of proteins such as SPARC, von Willebrand factor (VWF), and discoidin domain receptor 2 (DDR2), these binding sequences overlap substantially (FIG. 1). Furthermore, each of these proteins will only bind to collagen once it has folded into a triple-helical state. This specificity is shared by heat-shock protein 47 (HSP47), a chaperone protein found in the endoplasmic reticulum that supports mammalian collagen synthesis, and also by matrix metalloproteinase-1 (MMP-1), a prominent collagenase. Considering the breadth and complexity of collagen-protein interactions, detailed characterization of these relationships would allow for profound advances in PPI regulation and modulation.

In another exemplary embodiment, the present invention also provides HSP47 inhibitors useful as antifibrotic therapies to treat pathologies. In some embodiments, pathologies such as liver cirrhosis may be treated by HSP47 inhibitors. While many collagen-protein interactions have been characterized, all studies to date have utilized homotrimeric triple helical peptides. This situation is far from the reality of the heterotrimeric collagen-protein interfaces that occur in biology. Information on the specificity of protein interactions between genetic and fibrillar types of collagen is also lacking. The entire field of collagen-protein interactions has suffered from a lack of tools for investigating these unique PPIs and there is much to be uncovered with the right chemical tools. For example, the specific structure of the collagen-HSP47 binding complex is not fully elucidated and the only co-crystal structure to date is complexed with a homotrimeric collagen peptide triple helix. HSP47 has been implicated as important in embryonic development and its overexpression has also been linked to fibrosis, making it an important target for new therapeutic development and fundamental investigations. These intriguing properties indicate that novel HSP47 inhibitors could be useful as antifibrotic therapies designed to treat pathologies such as liver cirrhosis.

In another exemplary embodiment, the present invention also provides for the production of hyperstable CMPs of minimal length that contain triplet sequences of the form Xaa-Arg-Gly in homotrimeric and heterotrimeric forms. In another exemplary embodiment, the present invention also provides for a rational design approach based on incorporating aza-Gly containing collagen peptides into heterotrimeric triple helix mimics to extend to numerous biomedically relevant binding sequences and collagen-protein interactions of therapeutic importance. In another exemplary embodiment, the present invention also provides for the studying of structure and binding interactions of important collagen sequences and chaperone complexes that have previously been difficult to attain at high resolution. Triplet sequences of the form Xaa-Arg-Gly have been shown to be particularly effective binding sites for HSP47 in both native and synthetic collagen peptides, although all these studies have been conducted with homotrimeric triple helical peptides. As such, it would be useful to use our newly discovered azGly substitutions produce hyperstable CMPs of minimal length that contain this sequence in not only homotrimeric form but also heterotrimeric. Similarly, highly specific MMP modulators would be an important advance since the interaction between collagen and MMPs has been shown to be important in the progression of cancerous tumors. A rational design approach based on incorporating aza-Gly containing collagen peptides into heterotrimeric triple helix mimics would extended to numerous other biomedically relevant binding sequences and collagen-protein interactions of therapeutic importance (see Table 2). These azapeptides could then be used to study the structure and binding interactions of important collagen sequences and chaperone complexes that would be difficult to attain at high resolution otherwise.

In another exemplary embodiment, the present invention also provides for the control cell adhesion and morphology, modulation of cellular phenotypic functions, and the interplay of chemomechanical cues at the cell-matrix interface by modulating collagen-protein interactions with specific chemical tools. The response of tissue to injury is a complex, orchestrated event involving a variety of cells, soluble factors, and ECM proteins, including collagens. Collagen is a principal component of the extracellular matrix, a dynamic network of biochemical factors and physiochemical forces that mediates countless vital cellular and tissue-level processes. Recent efforts toward the systematic design of effective hierarchical biomaterial systems have worked to control cell adhesion and morphology, modulation of cellular phenotypic functions, and the interplay of chemomechanical cues at the cell-matrix interface. This, in principle, can also be accomplished by modulating collagen-protein interactions with specific chemical tools.

In another exemplary embodiment, the present invention also provides azapeptides to synthesize collagen triple helix mimics, HPT-mimics, in order to target and modulate collagen-protein interactions. The unprecedented stability offered by aza-glycine substitution in minimal collagen mimetic peptides makes them an innovative building block for higher-order structures. Specifically, the present invention utilizes these azapeptides to synthesize collagen triple helix mimics, HPT-mimics, in order to target and modulate collagen-protein interactions. These tunable, modular systems will be distinctly useful in characterizing the collagen interactome through peptide-protein binding assays and other related experiments. One subtle but very important distinction that separates the present aza-glycine stabilization method from all other technologies to date is that the present modification doesn't alter or change the overall triple helix surface topology. This is critical for maintaining the molecular recognition properties with interacting proteins. This ability to tune the thermodynamic and kinetic properties at the core without changing the surface structure is novel and highly innovative. Moreover, this is a conceptually novel approach utilizing aza-amino acid incorporation into collagen peptides that has not been explored to date. This approach overcomes many limitations in the field by providing a general way to stabilize short collagen peptide triple helical assemblies in novel manner that has not been pursued by any other research group in the past.

In another exemplary embodiment, the present invention also allows for the systematic incorporation of azGly at each position within collagen model peptides to assess the positional preference in terms of triple helix stability and folding kinetics. Multiple azGly residues can also be incorporated in a systematic fashion toward all azGly containing collagen peptide systems and minimal peptide motifs. In some embodiments, the present invention incorporates important protein recognition sequences into new minimal peptide motifs. For example, some important protein recognition sequences are listed in Table 2 and target 5 different and important collagen-protein interactions. The peptide sequences listed in Table 2 can be synthesized in their native form and aza-glycine containing form. These peptides can then be compared using standard biophysical techniques such as CD, SEC-MALS, AUC, and NMR including 2D-NMR methods.

In another exemplary embodiment, the present invention also provides for the synthesis of hyperstable collagen azapeptides using solid-phase peptide synthesis (SPPS). In some embodiments, the process of SPPS can occur as follows: first synthesize the amino acid trimers Proline-Hydroxyproline-Glycine (Fmoc-PO(tBu)G-OH) and Aza-Glycine-Proline-Hydroxyproline (Fmoc-azGPO(tBu)-OH), each with a 9-fluoroenylmethoxycarbonyl (Fmoc) protecting group, to use as the primary building blocks in the azapeptides. The use of these tripeptide synthons also allows for greater efficiency and higher yields by lowering the total number of reaction steps per synthesis. Next, an iterative series of deprotection and coupling reactions to sequentially add new building blocks to the growing peptides can be carried out. When the desired sequence deviates from the POG trimer, amino acids will be coupled individually using commercially available reagents (e.g. Fmoc-Hyp(tBu)-OH). In the same manner, when the use of the azGPO trimer is not feasible for a given peptide sequence, individual aza-amino acid residues will be integrated at various locations using Fmoc-protected hydrazine (Fmoc-NH—$NH_2$) and 1-1'-carbonyldiimidazole (CDI). By synthesizing an array of azapeptides in this manner, a determination of the ideal number and position of aza-amino acids to integrate into each peptide in order to optimize properties for particular collagen-protein interactions can be made. For each azapeptide produced, a corresponding non-azapeptide can also be synthesized as a control.

Following SPPS, the azapeptides can be precipitated in cold ether and purified using high-performance liquid chromatography (HPLC). The chemical composition of the chromatographic fractions can then be analyzed by matrix-assisted laser desorption/ionization time-of-flight mass spectrometry (MALDI-TOF MS). The fractions can then be pooled according to purity prior to lyophilization. Because the aza-glycine containing collagen peptides of the present invention are much shorter than traditional collagen mimetic peptides, high purity peptides can be obtained directly after cleavage from resin. The solid-phase procedures can also be further optimized in order to obtain high purity peptides directly from resin cleavage with the goal of avoiding HPLC purification. Furthermore, alternative resins for high purity peptide synthesis such as more modern PEG-containing resins can also be utilized to improve yield and purity. Precipitation of the peptides after resin cleavage can result in high purity products and facilitate scale-up and decrease the overall cost of peptide production.

In another exemplary embodiment, the present invention provides for the characterization of collagen peptides. Understanding the thermodynamic stability of these collagen azapeptides is important in assessing their usefulness as collagen-protein interaction modulators. To this end, circular dichroism (CD) can be used to characterize the processes of melting, refolding, and self-assembly for each azapeptide. This data can then be compared to corresponding data for each non-azapeptide in order to assess how the presence of aza-amino acids influences the kinetic and thermodynamic properties of collagen. Collagen peptides can be characterized using CD for unfolding and kinetic refolding experiments in addition to several other biophysical approaches such as analytical ultracentrifugation and SEC/MALS for characterization of the multimeric state. MD simulations can also be used for investigating the dynamics associated with amino acid substitutions in collagen peptides and for modeling synthetic modifications.

In another exemplary embodiment, the present invention provides for the characterization of collagen peptides using X-ray diffraction (XRD). Crystallography is an important aspect of characterization, as it provides fundamental information about the peptide's 3D structure following self-assembly and allows for structure based design and inspiration for new modifications. In order to fully understand the chemistry and molecular interactions of the novel collagen azapeptides or the present invention, crystallization of each new peptide using sitting drop vapor diffusion and solve their respective structures at a resolution of ≤1.5 Å using X-ray diffraction (XRD). This structural information is vital to the subsequent design of new collagen peptides and their interactions with important proteins such as HSP47 and MMP-1. Due to the importance of HSP47 and MMP1, both proteins are available in pure form from various vendors and are easily expressed. Moreover, synchrotron data collection at SSRL and APS beamlines can be used to obtain high resolution crystal structures of collagen azapeptide triple helices. For example, the first high resolution crystal structure of a collagen azapeptide triple helix with a resolution of 1.1 Å is provided in the example section. This data provides a firm structural basis for stabilization of the collagen triple helix using aza-glycine substitutions.

Figure 3:
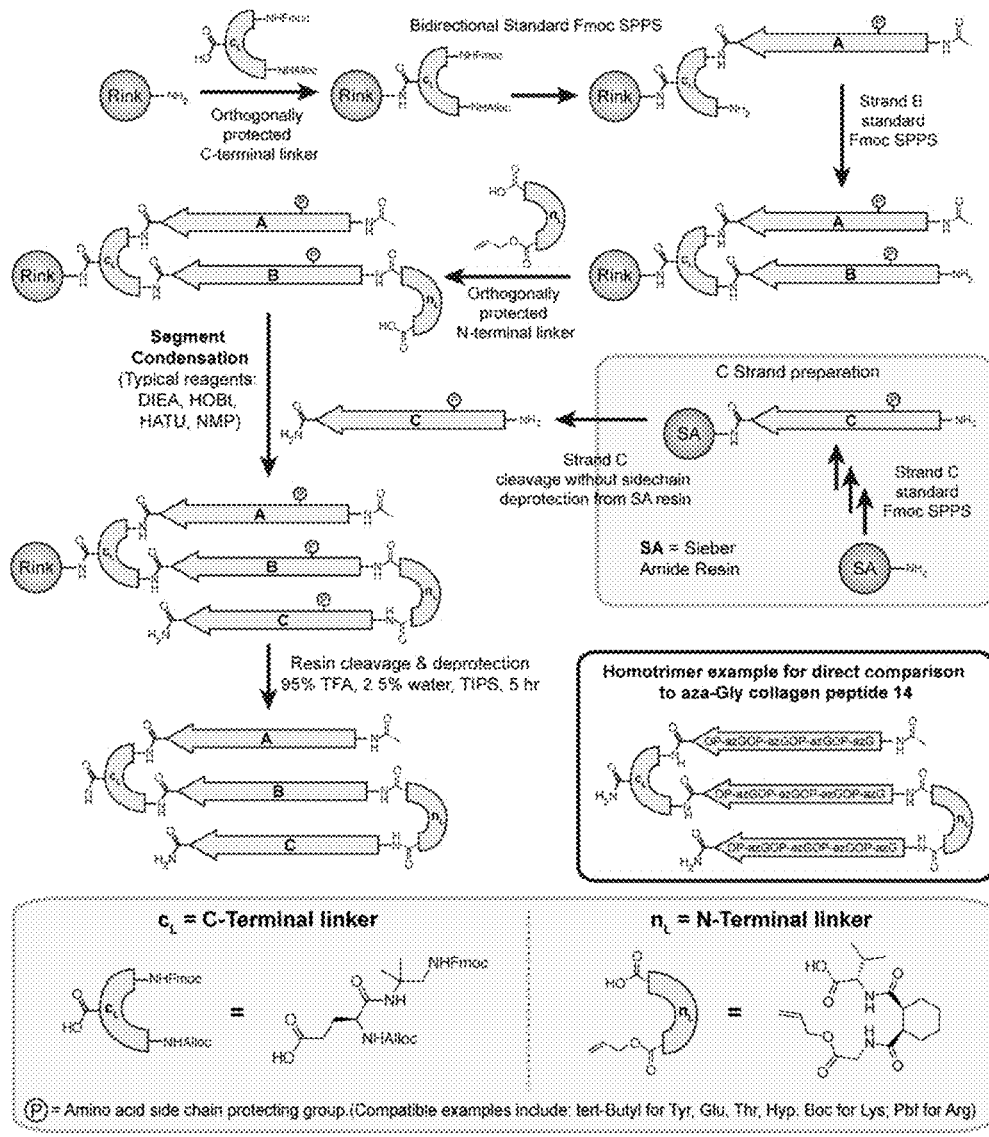
FIG. 3 shows the graphical reaction scheme for synthesis of HPT-mimics. Using convergent solid-phase synthesis, allows the preparation of novel Heterotrimeric Parallel Triple-helix mimics (HPT-mimics). The unique modularity of this system will allows the tuning of biophysical properties of these HPT-mimics by integrating modular azapeptide sequences to each HPT system. This can create an unprecedented opportunity to study biologically relevant synthetic heterotrimeric sequences.
Figure 5A:
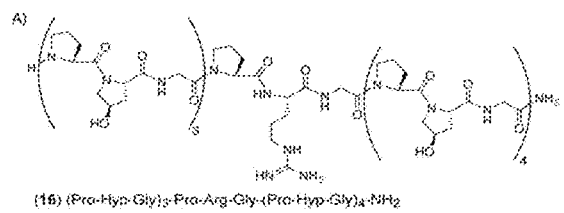
FIG. 5A-FIG. 5H shows a structural basis for aza-glycine substitution. A) Structural illustration of aza-glycine substitution in an Arg-containing CMP sequence. B) CD thermal melting curves of 16 and 17 showing an 8.8° C. increase in melting temperature following azGly substitution. C) CD kinetic refolding curves indicating enhanced refolding kinetics after thermal denaturation due to azGly substitution. D) Structure of 17 (1.13 Å resolution) shown as anisotropic thermal ellipsoids (left) and with complete hydration shell and sulfate ion as anisotropic thermal ellipsoids (right). E-H)
Figure 5B:
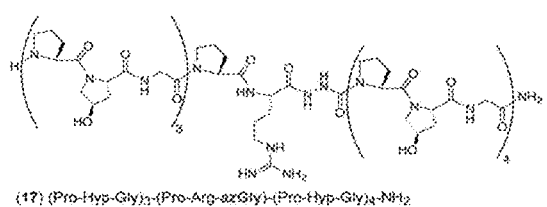
Figure 5C:
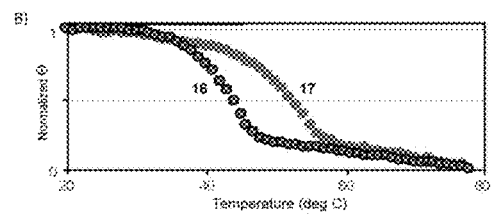
Figure 5D:
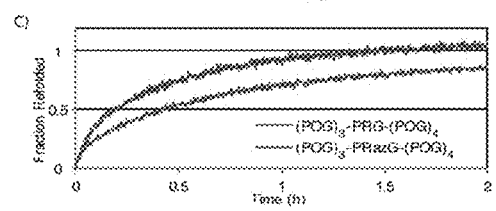
Figure 5E:
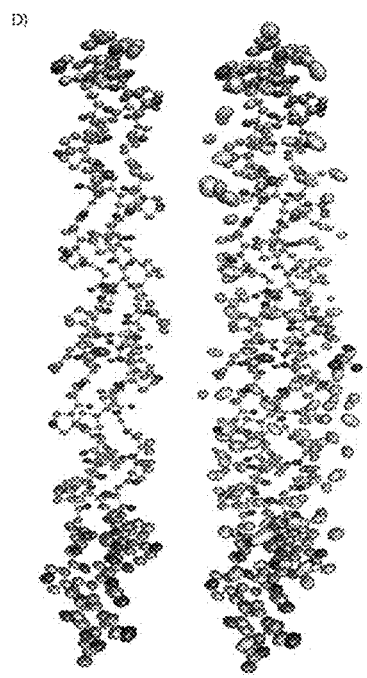
Figure 5F:
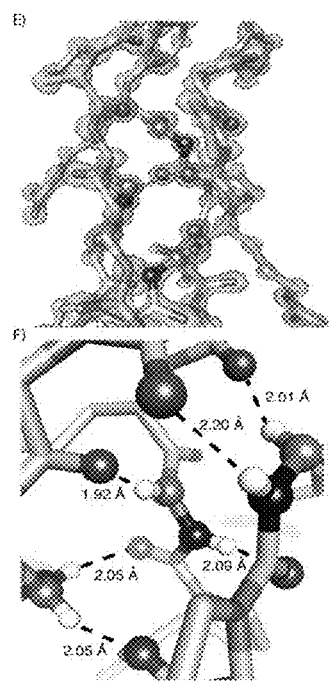
Figure 5G:
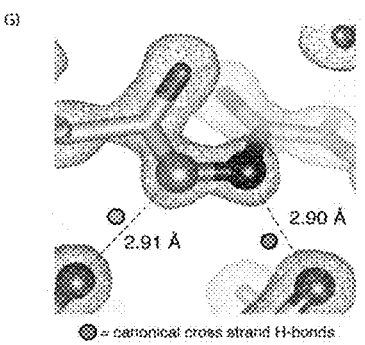
Figure 5H:
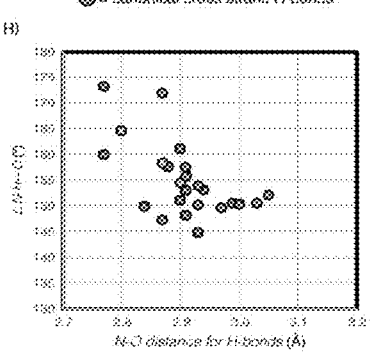

In another exemplary embodiment, the present invention also provides for the design and synthesis of an array of collagen HPT-mimics. Those skilled in the art will recognize that the syntheses rely on standard SPPS methods as outlined in FIG. 3. After verifying that collagen azapeptides can be effectively integrated into HPT-mimics, analysis of the effect that the presence of aza-amino acids has on the properties of these higher-order structures can be explored. This analysis follows the same paradigm as outlined above for single peptides: for each aza-amino acid-containing HPT-mimic, a control protein containing no aza-amino acid residues can also be prepared. These pairs of collagen helix mimics can then be compared in terms of thermal stability and folding properties, conformational tendencies, and overall propensity towards triple helical conformation using a combination of CD spectroscopy, NMR, and MD simulations. Structural insight can also be gained by 2D-NMR, molecular dynamics (MD) simulations and X-ray crystallography. Crystal structures can be analyzed and compared to homotrimeric collagen crystal structures and MD simulation data. This structural information can then be used to inform future design and re-design of minimal linker and peptide regions for creating new protein targeting motifs.

In order to further parallel analysis of individual azapeptides, it is useful to characterize the influence of aza-amino acid substitution on the kinetics of refolding in the context of higher-order structures. To this end, CD spectroscopy can be used to examine the kinetics of refolding after thermal denaturation. It is possible that the addition of new hydrogen bonds to the HPT-mimic secondary structure may greatly expedite their rate of refolding ($\Delta t_{1/2} \geq 10$ min, where $t_{1/2}$=the time at which the peptide regains 50% of its initial triple helicity). Chemical denaturing conditions such as guadinium-HCl can be used to assess folding/unfolding. In addition, using variable temperature NMR and can be very useful for all studies of the present invention.

In another exemplary embodiment, the present invention provides for design minimal synthetic collagen triple helix mimics for modulating collagen-protein interactions. It is understood the stabilizing effect of aza-glycine is general and at least additive without perturbation to overall collagen topological structure or recognition properties important for collagen-protein interactions. This provides for a wealth of opportunities using short but stable triple helix-forming collagen peptides, as the novel aza-glycine substitution allows for complete flexibility in tuning the stability and assembly properties of collagen independent of length or collagen recognition sequences. Outside of the materials applications outlined in this proposal there are myriad important applications in the area of new collagen peptide imaging agents and new tools for structural biology. In structural biology, these modifications can allow for the determination of new collagen-protein structures that have remained elusive to date.

Although collagen is characterized primarily by the repeating trimer sequences POG and PPG, the >29 known types of collagen are distinguished by the other amino acids included in their peptide sequences that confer many of the molecular recognition properties and specificity toward interacting proteins. As such, synthesizing collagen peptides containing non-POG sequences and investigating their stability, biocompatibility, and interactions with other relevant biomolecules such as the proteins listed in Table 2 in addition to important proteins like integrins would be beneficial. In addition, synthesis of an array of such peptides, each with a different recognition peptide or a combination of recognition peptides Table 2 and use of these peptides for biophysical studies with all relevant proteins listed in Table 2 would be also beneficial. All proteins listed in Table 2 are commercially available in their purified human recombinant form and we are already working with HSP47 and MMP-1.

Recent studies indicate, for instance, that a single aza-glycine substitution in an arginine-containing collagen sequence can substantially increase the thermal stability of the peptide by ~9° C. as shown in the preliminary data in FIG. 5 This result is significant because this represents an important part of the collagen recognition sequence for HSP47. Another studies focus on the synthesis of a collagen azapeptide composed of the shortest stable binding sequence for the von Willdebrand Factor (VWF) Boudko and Bachinger have previously synthesized this sequence, (GPR)(GQO)(GVM)(GFO), without any aza-amino acids.[6] Although the sequence was synthetically supplemented with two GPO tripeptides on either end of the primary sequence, it was reported that the secondary structure of each strand in the resulting triple helix suffered from disorder. This type of observation has plagued the collagen filed since most short collagen peptide sequences containing non-POG triplets do not form stable triple helices at physiologically relevant temperatures. For this reason, synthesis of this VWF sequence using 4 azGly substitutions: (azGPR)(azGQO)(azGVM)(azGFO) is important. The VWF protein is readily available in human recombinant form and can be used this to study interactions with HPT-mimics. The previously noted enhancements to interstrand hydrogen bonding that this substitution provides may create the added stability needed to induce triple helix self-assembly for this sequence. The CMP sequences are presented in Table 2. As the research progresses, the list of proteins in FIG. 1 and Table 2 will expand to include an expansive library of relevant sequences that explore the collagen interactome in addition to exploration of the chemomechanical utility of cell-matrix PPI interactions induced by binding the adhesome of transmembrane proteins and matrisome of ECM proteins.

In another exemplary embodiment, the present invention provides for the characterization of the influence of backbone modifications on collagen-protein interactions. After designing and synthesizing a library of biologically relevant collagen azapeptide sequences, characterization the bioactivity of these sequences using an array of biophysical assays can be achieved. The biophysical characterization begins by extensively probing the specific relationship between aza-amino acid substitution and higher-order structural and biological properties. Moreover, serial solid-phase peptide synthesis can be utilized in order to characterize the impact of various azGly substitutions in a given collagen peptide template sequence. This positional scanning allows manipulation of the thermal and kinetic stability of minimal collagen peptides by varying the number, location, and spacing of aza-amino acids in a collagen peptide. Using a similar methodology, tuning and optimization of the higher-order properties of these important protein binding sequences using aza-amino acid substitution can be obtained. Because the aforementioned HPT-mimics are composed of modular peptide chains, it will be feasible to integrate specific binding sequences into a biologically relevant higher-order protein structure using well-defined synthetic protocols. This process will make these sequences highly viable and allow for their efficient production for subsequent biophysical analyses.

In another exemplary embodiment, the present invention provides for the determination of influence of azGly substitution on exclusive protein binding in folded and unfolded states. It has been observed that the propensity of several important proteins to bind to collagen is dependent upon the folding state of the collagen sequence in question. That is, several enzymes that promote the collagen folding process (e.g. lysyl hydroxylase, prolyl 4-hydroxylase) exclusively bind to unfolded collagen. Conversely, proteins important in cell-cell interactions and collagen degradation (e.g. VWF, MMP1, DDR2) as well as the aforementioned chaperone HSP47 bind only to folded collagens. Given the apparent selectivity with which many of these proteins bind to collagen, it will be useful to determine whether the presence of aza-amino acids in these protein binding sequences will influence the efficacy of their binding. This can accomplished using solid-phase and solution-phase peptide binding assays that can compare the protein binding ability of specific collagen peptides alongside a range of azapeptide variants of this same collagen sequence (e.g. (POG)5 vs. (POG)(POazG)(POG)3 vs. (POG)2(POazG)(POG)2, etc.). To examine the changes in peptide-protein binding in the folded vs. unfolded states, these assays can be carried out at both low and high temperatures via a circulating water bath in order to relegate the chosen peptide into either the triple helical or single-stranded state. In the case of HSP47, these results can be supplemented with a fluorescence quenching assay in which the quenching of the fluorescence signal emitted by the Trp residues in HSP47 (measured by spectrofluorometer) indicate successful peptide-protein binding.

In another exemplary embodiment, the present invention provides for the examination of the effect of non-enzymatic post-translational modifications on collagen peptide-protein interactions. To expand on the biophysical assays described above, the susceptibility of azapeptide sequences to non-enzymatic post-translational modifications which effect collagen protein recognition and build up during the aging process can also be examined. Through a Maillard reaction with arginine residues, methylglyoxal has been shown to function in the production of detrimental advanced glycation end products that advance the development of diabetes and neurodegenerative disease, among others. Using similar assays as those described above, the reactivity of methylglyoxal toward an arginine-containing collagen peptide and a range of azapeptide mimics thereof (FIG. 5—Arg CMP structural illustration) can be compared. This directly relates to the ability of collagen to participate in critical protein-protein interactions important to human physiology and pathologies. It can then be determined if the methyl glyoxal treated Arg containing CMPs retain the capacity to interact with HSP47. This has important implications in human aging and the complex interplay of collagen.

In another exemplary embodiment, the present invention provides for the structural characterization of synthetic collagen peptide-protein interactions. In order to complement these biophysical analyses, XRD can be used to gather crucial structural information for each peptide-protein binding complex being studied. This canallow us to use hyperstable minimal azapeptides to achieve high-resolution structures of CMPs bound to biologically relevant proteins. Detailed knowledge of the local conformational intricacies of specific collagen sequences could provide crucial information for the design of therapies targeting HSP47.

The following specific examples further illustrate the structural basis, design principles, manufacturing methods and practical applications of the aza-CMPs disclosed herein.

REFERENCES FOR BACKGROUND AND BRIEF DESCRIPTION OF THE INVENTION

1. Goodman, M.; Bhumralkar, M.; Jefferson, E. A.; Kwak, J.; Locardi, E. Biopolymers 1998, 47, 127.

2. Newberry, R. W.; VanVeller, B.; Raines, R. T. Chem. Commun. 2015, 51, 9624.
3. Jenkins, C. L.; Vasbinder, M. M.; Miller, S. J.; Raines, R. T. Org. Lett. 2005, 7, 2619.
4. Dai, N.; Etzkorn, F. A. J. Am. Chem. Soc. 2009, 131, 13728.
5. (a) Shah, N. K.; Brodsky, B.; Kirkpatrick, A.; Ramshaw, J. A. M. Biopolymers 1999, 49, 297-302. (b) Jenkins, C. L.; Vasbinder, M. M.; Miller, S. J.; Raines, R. T. Org. Lett. 2005, 7, 2619. (c) Dai, N.; Etzkorn, F. A. J. Am. Chem. Soc. 2009, 131, 13728. (d) Newberry, R. W.; VanVeller, B.; Raines, R. T. Chem. Commun. 2015, 51, 9624.
6. Boudko S. P.; Bachinger H. P. J Biol Chem. 2012; 287(53):44536-45. doi: 10.1074/jbc.M112.417543.

EXAMPLES

Example 1: azGly Confers Stabilizing Effect to Aza-CMP Triple Helices

Recently, new insight has been provided into the fundamental importance of stereochemistry as a pre-organizing element in biomolecular folding and assembly events by introducing stereodynamic centers at key locations within biomolecules.[14] It was demonstrated that the rate of triple helix self-assembly in a stereodynamic collagen model peptide is dramatically altered with little to no effect on the thermal unfolding. In this example, replacing the alpha carbon of glycine with a nitrogen atom and shows that addition of an extra hydrogen bond donor in the backbone can lead to a hyperstable collagen triple helix. Described herein is the first atomic modification to the main chain backbone of collagen that has resulted in significant triple helix hyperstability and significantly faster folding kinetics. These results have important implications for the design of new self-assembling biomimetic materials.

Peptides 1-4 shown in FIG. 7 to assess the effects of substituting glycine (Gly) with aza-glycine (azGly)[15,16] in the context of a collagen model peptide system have been synthesized. Our design constitutes replacement of a single CH with a single nitrogen atom at the central location in a 260 atom (21 amino acid) peptide system (FIG. 7). Circular dichroism (CD) spectroscopy was used to evaluate self-assembly of the triple helix for each of our collagen model peptides. CD measurements of solutions containing collagen model peptide 3 and 4 both exhibit characteristic maxima at approximately 224 nm, indicating the presence of triple helix structure. Thermal denaturation experiments showed that all peptides underwent cooperative unfolding transition upon heating (see S.I.). The data from CD thermal denaturation experiments were fitted to a two-state model, as previously described. 17 The melting temperatures, at which 50% of the triple helix unfolds, are shown in FIG. 3A for peptides 1-4. A striking increase of approximately 10° C. in melting temperature was observed compared to the corresponding control compounds, 1 and 2. The results show that replacement of a single glycine alpha CH with a nitrogen atom results in a significant increase in triple helix thermal stability. In addition to being the first favorable replacement for a glycine residue in a collagen model peptide, 8c, 18 this substitution results in the highest stabilizing effect of any single residue mutation in a collagen PPG or POG peptide system. 19 Raines and co-workers reported a seminal study where replacement of a single Pro residue with a fluorinated Pro (Flp) residue results in a 5° C. increase in thermal stability.20 Pairing the azGly residue with the fluoroproline discovery of Raines could result in extremely stable collagen peptide systems with unique and new material properties.

A model based on a known collagen crystal structure in which a glycine was substituted by azGly shows the azGly alpha NH is 2.2 Å from the carbonyl of Gly and 3.2 Å from the carbonyl of Pro in a neighboring peptide chain. This is similar in length to the key canonical interstrand hydrogen bond from the Gly amide NH to the carbonyl preceding Pro in the Yaa position. Additional hydrogen bonding from azGly could increase the number of interchain hydrogen bonds within a triplet of Xaa-Yaa-Gly, providing a connection between all three peptide chains through multiple dynamic hydrogen bonds.

Next, we assessed the kinetics of triple helix formation for peptides 1-4. Peptides 1-4, at a concentration of 0.2 mM in PBS buffer, were denatured at 80° C. for 15 min and their CD profiles were monitored at 4° C. until both peptides recovered (>50%) ellipticity at 224 nm.[21] The refolding rate of peptides containing the azGly moiety were enhanced in both comparisons. The presence of trimers was confirmed for collagen peptides 1-4 by SEC-MALS analysis using a D-proline containing collagen peptide (5) as a monomeric control (FIG. 7e).[14] In addition, the trimeric state of azGly containing peptides 3 and 4 was also verified by sedimentation equilibrium analysis using analytical ultracentrifugation (AUC).

A hysteresis study was performed to gain further insight into the stability of peptides 3 and 4.22 The free energy difference of the peptides was in accord with the difference in Tm and previous reports using this method. The ΔG's were found to be −11 and −12 kcal/mol for peptide 1 and 2, respectively. Peptides 3 and 4 both displayed ΔG values of −13 and −15 kcal/mol respectively. The origin of the free energy difference is primarily consistent with an increase in the enthalpic gain from the ability of azGly to form extra hydrogen bonds, although this will require verification by calorimetric methods. The large difference in half time values for triple helix self-assembly for azGly containing peptides are striking in comparison to our previous results with aza-proline, where we elucidated the role of stereochemistry with respect to biopolymer preorganization and self-assembly.[14]

Our model suggests the incorporation of azGly into the triplet adds the possibility for extra hydrogen bonding between the new alpha NH and two different amide carbonyls on an adjacent peptide strand in addition to the already present amide hydrogen bond. To gain further insight into the azGly substitution we performed MD calculations using GROMACS (see supporting information for details). Simulations on full triple helical models of peptides 1-4 revealed heavy atom RMSD values of <0.07 for the central 5 amino acid triplets of peptides 1 and 2 and slightly higher RMSD values for the N- (0.2) and C-terminal (0.14) triplets compared to a common starting model (FIG. 8).

Figures 9A, 9B, 9C, 9D:
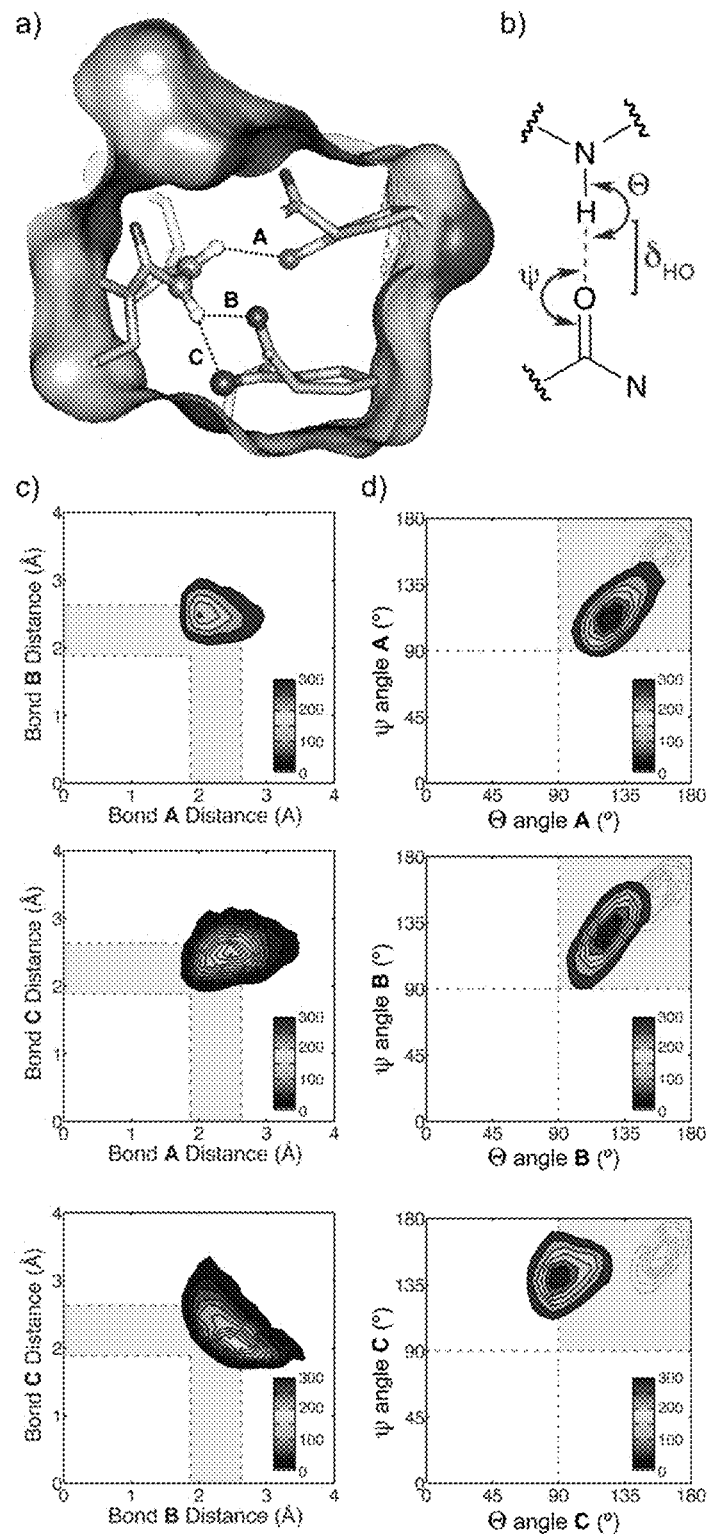

The azGly containing triple helical structures 3 and 4 showed similar RMSD values as the parent systems except at the azGly position near the central triplet, where the RMSD values increased to 0.10 for peptide 3 and 0.08 for peptide 4. Analysis of the azGly hydrogen bonding parameters revealed the possibility of three different hydrogen bonds at each azGly residue with the new alpha NH participating in up to two hydrogen bonds (FIG. 8). Hydrogen bond distances are shown in FIG. 9c with angles shown in FIG. 9d, revealing the possibility for three dynamic hydrogen bonds with slightly less optimal parameters than the standard amide hydrogen bond present in collagen. The MD simulation data implies that multiple dynamic but weak hydrogen bonds with non-optimal distance and angle parameters may be more favorable in certain cases than strong hydrogen bonds.

Peptide backbone substitutions have provided a wealth of insightful information regarding protein structure. Additionally, they have led to the discovery of new interactions of fundamental importance such as the gauche effect in collagen and n-π* interactions. Previous reports of heteroatom replacement in the collagen peptide backbone have resulted in either severe destabilization or a complete lack of triple helix formation. Amide-to-ester substitutions have provided a wealth of information regarding hydrogen bond strength and have a detrimental impact on collagen triple helix stability. In addition, trans alkene amide bond isosteres greatly destabilize the triple helical structure of collagen irrespective of positioning and involvement in hydrogen bonding. To date, these efforts have demonstrated an intolerance of the collagen peptide backbone to molecular editing.[13]

Our study suggests that nature's limited set of building blocks are not sufficient for optimizing the stability of self assembled biopolymer systems such as collagen, and there is much to be gained from judicious synthetic modifications such as azGly incorporation. In addition to insight into the fundamental importance of hydrogen bonding as a stabilizing element in natural systems, these studies may provide insight into optimization of self-assembling biomimetic materials. Beyond collagen, these studies suggest the opportunity for protein stabilization in a broader context via azGly scanning, which could identify unique positions for increasing thermal stability in addition to decreasing proteolytic degradation as already reported for aza-amino acids.

REFERENCES FOR EXAMPLE 1

1. Srinivasan, R.; Rose, G. D. *Proc. Natl. Acad. Sci. USA* 1999, 96, 14258.
2. Anfinsen, C. B. *Science* 1973, 181, 223.
3. (a) Černý, J.; Hobza, P. *Phys. Chem. Chem. Phys.* 2007, 9, 5291. (b) Dunitz, J. D. *Chem. Biol.* 1995, 2, 709. (c) Schneider, H.-J. *Angew. Chem. Int. Ed.* 2009, 48, 3924. (d) Williams, D. H.; Stephens, E.; O'Brien, D. P.; Zhou, M. *Angew. Chem. Int. Ed.* 2004, 43, 6596.
4. (a) Mirsky, A. E.; Pauling, L. *Proc. Natl. Acad. Sci. USA* 1936, 22, 439. (b) Pauling, L.; Corey, R. B.; Branson, H. R. *Proc. Natl. Acad. Sci. USA* 1951, 37, 205. (c) Pauling, L.; Corey, R. B. *Proc. Natl. Acad. Sci. USA* 1951, 37, 729.
5. (a) Hubbard, R. E.; Kamran Haider, M. In eLS; John Wiley & Sons, Ltd, 2001. (b) Deechongkit, S.; Nguyen, H.; Powers, E. T.; Dawson, P. E.; Gruebele, M.; Kelly, J. W. *Nature* 2004, 430, 101. (c) Pace, C. N. *Nat. Struct. Mol. Biol.* 2009, 16, 681. (d) Gao, J.; Bosco, D. A.; Powers, E. T.; Kelly, J. W. *Nat. Struct. Mol. Biol.* 2009, 16, 684. (e) Bowie, J. U. *Curr. Opin. Struc. Biol.* 2011, 21, 42.
6. (a) Pauling, L.; Corey, R. B. *Nature,* 1951, 168, 550. (b) Pauling, L.; Corey, R. B. *Proc. Natl. Acad. Sci. USA* 1951, 37, 241. (c) Crick, F. H. C. *Nature* 1952, 170, 882. (d) Watson, J. D.; Crick, F. H. C. *Nature* 1953, 171, 737.
7. (a) He, M.; Bode, J. W. *Proc. Natl. Acad. Sci. USA* 2011, 108, 14752. (b) Barrett, K. T.; Metrano, A. J.; Rablen, P. R.; Miller, S. J. *Nature* 2014, 509, 71. (c) Wang, J.; Feringa, B. L. *Science* 2011, 331, 1429. (d) Clayden, J.; Lund, A.; Vallverdú, L.; Helliwell, M. *Nature* 2004, 431, 966.
8. (a) Ramachandran, G. N.; Kartha, G. *Nature* 1954, 174, 269. (b) Rich, A.; Crick, F. H. *J. Mol. Biol.* 1961, 3, 483. (c) Shoulders, M. D.; Raines, R. T. *Annu. Rev. Biochem.* 2009, 78, 929.
9. (a) Bella, J.; Eaton, M.; Brodsky, B.; Berman, H. M. *Science* 1994, 266, 75. (b) Holmgren, S. K.; Taylor, K. M.; Bretscher, L. E.; Raines, R. T. *Nature* 1998, 392, 666. (c) Fields, G. B.; Prockop, D. J. *Biopolymers* 1996, 40, 345. (f) Schumacher, M.; Mizuno, K.; Bachinger, H. P. *J. Mol. Biol.* 2005, 280, 20397. (d) Goodman, M.; Melacini, G.; Feng, Y. *J. Am. Chem. Soc.* 1996, 118, 10928. (e) Kawahara, K.; Nishi, Y.; Nakamura, S.; Uchiyama, S.; Nishiuchi, Y.; Nakazawa, T.; Ohkubo, T.; Kobayashi, Y. *Biochemistry* 2005, 44, 15812. (f) Berisio, R.; Vitagliano, L.; Mazzarella, L.; Zagari, A. *Protein Sci.* 2002, 11, 262. (m) Gauba, V.; Hartgerink, J. D. *J. Am. Chem. Soc.* 2007, 129, 2683. (g) Gauba, V.; Hartgerink, J. D. *J. Am. Chem. Soc.* 2007, 129, 15034. (h) Lee, S.-G.; Lee, J. Y.; Chmielewski, J. *Angew. Chem. Int. Ed.* 2008, 47, 8429.
10. (a) Kusebauch, U.; Cadamuro, S. A.; Musiol, H.-J.; Lenz, M. O.; Wachtveitl, J.; Moroder, L.; Renner, C. *Angew. Chem. Int. Ed.* 2006, 45, 7015. (b) Cejas, M. A.; Kinney, W. A.; Chen, C.; Leo, G. C.; Tounge, B. A.; Vinter, J. G.; Joshi, P. P.; Maryanoff, B. E. *J. Am. Chem. Soc.* 2007, 129, 2202. (c) Rele, S.; Song, Y.; Apkarian, R. P.; Qu, Z.; Conticello, V. P.; Chaikof, E. L. *J. Am. Chem. Soc.* 2007, 129, 14780. (d) Wang, A. Y.; Mo, X.; Chen, C. S.; Yu, S. M. *J. Am. Chem. Soc.* 2005, 127, 4130. (e) Przybyla, D. E.; Chmielewski, J. *J. Am. Chem. Soc.* 2008, 130, 12610. (f) Fallas, J. A.; Gauba, V.; Hartgerink, J. D. *J. Biol. Chem.* 2009, 284, 26851.
11. (a) Holmgren, S. K.; Taylor, K. M.; Bretscher, L. E.; Raines, R. T. *Nature* 1998, 392, 666. (b) Bretscher, L. E.; Jenkins, C. L.; Taylor, K. M.; DeRider, M. L.; Raines, R. T. *J. Am. Chem. Soc.* 2001, 123, 777. (c) Hodges, J. A.; Raines, R. T. *J. Am. Chem. Soc.* 2003, 125, 9262. (d) Shoulders, M. D.; Hodges, J. A.; Raines, R. T. *J. Am. Chem. Soc.* 2006, 128, 8112. (e) Kotch, F. W.; Guzei, I. A.; Raines, R. T. *J. Am. Chem. Soc.* 2008, 130, 2952. (f) Cadamuro, S. A.; Reichold, R.; Kusebauch, U.; Musiol, H.-J.; Renner, C.; Tavan, P.; Moroder, L. *Angew. Chem.* 2008, 120, 2174. (g) Umashankara, M.; Babu, I. R.; Ganesh, K. N.; *Chem. Commun.* 2003, 2606. (h) Erdmann, R. S.; Wennemers, H. *J. Am. Chem. Soc.* 2010, 132, 13957. (i) Shoulders, M. D.; Satyshur, K. A.; Forest, K. T.; Raines, R. T. *Proc. Natl. Acad. Sci. USA* 2010, 107, 559. (j) Bartlett, G. J.; Choudhary, A.; Raines, R. T.; Woolfson, D. N. *Nat. Chem. Biol.* 2010, 6, 615. (k) Choudhary, A.; Gandla, D.; Krow, G. R.; Raines, R. T. *J. Am. Chem. Soc.* 2009, 131, 7244. (l) Jakobsche, C. E.; Choudhary, A.; Miller, S. J.; Raines, R. T. *J. Am. Chem. Soc.* 2010, 132, 6651. (m) Erdmann, R. S.; Wennemers, H. *Angew. Chem. Int. Ed.* 2011, 50, 6835. (n) Erdmann, R. S.; Wennemers, H. *J. Am. Chem. Soc.* 2012, 134, 17117. (o) Siebler, C.; Erdmann, R. S.; Wennemers, H. *Angew. Chem. Int. Ed.* 2014, 53, 10340. (p) Newberry, R. W.; Bartlett, G. J.; VanVeller, B.; Woolfson, D. N.; Raines, R. T. *Protein Sci.* 2014, 23, 284.
12. Goodman, M.; Bhumralkar, M.; Jefferson, E. A.; Kwak, J.; Locardi, E. *Biopolymers* 1998, 47, 127.
13. (a) Frey, P.; Nitschmann, H. *Helv. Chim. Acta.* 1976, 59, 1401. (b) Shah, N. K.; Brodsky, B.; Kirkpatrick, A. Ramshaw, J. A. M. *Biopolymers* 1999, 49, 297-302; (c) Jenkins, C. L.; Vasbinder, M. M.; Miller, S. J.; Raines, R. T. *Org. Lett.* 2005, 7, 2619. (d) Dai, N.; Wang, X. J.; Etzkorn, F. A. *J. Am. Chem. Soc.* 2008, 130, 5396. (e) Dai, N.; Etzkorn, F. A. *J. Am. Chem. Soc.* 2009, 131, 13728. (f) Newberry, R. W.; VanVeller, B.; Raines, R. T. *Chem. Commun.* 2015, 51, 9624.
14. Zhang, Y.; Malamakal, R. M.; Chenoweth, D. M. *Angew. Chem. Int. Ed.* 2015, 54, 10826.
15. Sabatino, D.; Proulx, C.; Klocek, S.; Bourguet, C. B.; Boeglin, D.; Ong, H.; Lubell, W. D. *Org. Lett.* 2009, 11, 3650.
16. Reviews and selected work on incorporating azGly into biologically active peptides: (a) Zega, A. *Cur. Med. Chem.* 2005, 12, 589. (b) Proulx, C.; Sabatino, D.; Hopewell, R.; Spiegel, J.; Garcia Ramos, Y.; Lubell, W. D. *Chem Med. Chem.*, 2011, 3, 1139.
17. Engel, J.; Chen, H. T.; Prockop, D. J.; Klump, H. *Biopolymers* 1977, 16, 601.
18. Replacing Gly by Ala, Arg, Asp, Glu, Cys, Ser, Val, or selected $_D$-amino acid all lead to dramatic destabilization of the model host-guest system. (a) Beck, K.; Chan, V. C.; Shenoy, N.; Kirkpatrick, A.; Ramshaw, J. A. M.; Brodsky, B. *Proc. Natl. Acad. Sci. USA*, 2000, 97, 4273. (b) Horng, J. C.; Kotch, F. W.; Raines, R. T. *Protein Sci.* 2007, 16, 208. (c) Chen, Y. S.; Chen, C. C.; Horng, J. C. *Biopolymers* 2011, 96, 60.
19. Natural amino acids do not outcompete Pro in X and Hyp in Y: (a) Persikov, A. V.; Ramshaw, J. A. M.; Kirkpatrick, A.; Brodsky, B. *Biochemistry*, 2000, 39, 14940. (b) Jenkins, C. L.; Bretscher, L. E.; Guzei, I. A.; Raines, R. T. *J. Am. Chem. Soc.* 2003, 125, 6422.
20. Shoulders, M. D.; Kamer, K. J.; Raines, R. T. *Bioorg. Med. Chem. Lett.* 2009, 19, 3859.
21. See the Supporting Information for details. Mizuno, K.; Boudko, S. P.; Engel, J.; Bachinger, H. P. *Biophys. J.* 2010, 98, 3004.

Example 2: AzGly's Stabilizing Effect is General

One of the most ubiquitous non-covalent interactions in nature is the hydrogen bond, exemplified by Watson-Crick base pairing in the double helix of B-form DNA and the alpha helices and beta sheet secondary structures in proteins.[1-3] In fact, helical architectural motifs are one of the most common recurring structures in natural systems and they are often rich with hydrogen bonding interactions at their subunit interfaces. In the 1930's, Linus Pauling suggested in regard to protein structure that " . . . this chain is folded into a uniquely defined configuration, in which it is held by hydrogen bonds between the peptide nitrogen and oxygen atoms . . . . The importance of the hydrogen bond in protein structure can hardly be overemphasized."[2a] Historically, speculative model building by pioneers such as Pauling, Watson, and Crick has led to some of the greatest achievements in structural biology, many of which hinged on the correct pairing or maximizing of inter- and intra-chain hydrogen bonds in biopolymers.[4] Some of these early models, such as Pauling's original proposal for the structure of collagen, included too many hydrogen bonds at the expense of other structural perturbations (FIG. 10, top)

As the most prevalent protein in the human body, collagen has been the subject of research for decades on both the fundamental forces stabilizing its structure and biomaterial design.[5,6] Collagen is a right-handed super helix formed by three parallel left-handed polypeptide chains that mimic the polyproline II helix. The component chains of collagen may be conveniently described as repeating units of XaaYaaGly, in which Xaa and Yaa are usually occupied by (2S)-proline and (2S, 4R)-hydroxyproline (Hyp) respectively. Previous studies have revealed that side-chain modification using unnatural amino acid building blocks can modulate or enhance the stability of the triple-helical structure.[7] By contrast, collagen backbone modifications, with the exception of aza-proline replacing proline in the Xaa position by our lab and a thioamide incorporation in a Yaa proline reported by Raines et. al., have typically resulted in destabilized structures or no triple helix formation.[8]

In Example 1 above, we showed that replacing a single α-carbon of glycine with a nitrogen atom (substituting glycine for aza-glycine) in a collagen model peptide leads to a stabilized collagen triple helix.[9] We believe that this modification minimally perturbs the chemistry of the system and adds additional bifurcated hydrogen bonds in addition to the canonical hydrogen bonds identified in collagen[10] (see FIG. 2, middle). In that example, the aza-glycine (azGly) substitution occurred at the central location of a 21-mer peptide (FIG. 11A, peptide 2). Herein, we demonstrate that azGly substitution confers stability at all locations investigated in a model peptide, and extra stabilization was observed when multiple azGly residues are incorporated. Most importantly, the replacement of all "strictly conserved" glycine residues was achieved and a peptide as short as 12 amino acids in length is able to self-assemble into a stable triple helix under physiologically relevant conditions.

First, we synthesized collagen model peptides 3-7 using solid-phase synthesis methods[11] in addition to peptide 2 to assess the dependence of substitution location on conferred stability (FIG. 11A, B top). Purified peptides were incubated in PBS buffer for at least 24 hours. Circular dichroism (CD) spectra of aqueous solutions containing 3-7 all exhibit characteristic local maxima at approximately 224 nm in peptides containing a single aza-glycine, indicating the presence of triple-helical structure. Thermal denaturation experiments showed cooperative unfolding transitions for all peptides, like control peptide 1 and previously reported peptide 2. The data from CD thermal denaturation experiments were fitted to a two-state model as previously described.[12,13] The melting temperatures (Tm), at which 50% of the triple helix unfolds, are listed next to the peptides in FIG. 11. Peptides 1-7 (FIG. 11B, top) show the positional effect for substitution with a single aza-glycine residue. In-creases in Tm ranging from 6-11° C. were observed for peptides 2-7 compared to control peptide 1. A marked increase in stability caused by a single azGly in a POG-based system, regardless of which glycine residue is altered. The stabilization increases as the azGly moves from either end towards the center location with 2 exhibiting the highest Tm increase (11° C.) over the control peptide 1. The stabilizing effect of aza-glycine correlates with the dynamics along the collagen triple helix. functions as a "commander," which organizes the hydrogen bonding networks within the interior of the triple helix and achieves better optimization as it moves toward the central location on the chain.

Next, we synthesized peptides 8-12 to determine the effect of multiple azGly substitutions on the thermal stability of triple helical collagen peptides (FIG. 11B, middle). Confirmation of triple-helix self-assembly, thermal denaturation experiments, and curve fitting were carried out as described for 2-7. Increases in Tm of 17-21° C. relative to 1 were observed for disubstituted peptides 8, 9, and 10; while in-creases of ~30° C. were observed for tri-substituted peptides 11 and 12. The fact that two azGly substitutions add an extra ~20° C. of thermal stability to our $(POG)_7$ reference system while three azGly substitutions add ~30° C. seem to suggest that the thermal stability conferred upon a collagen-like system by multiple azGly substitutions is additive. This is the case for peptide 9, with a stabilization of 19° C. equal to the sum of stabilization from single substitution as seen in peptide 5 (+10) and 6 (+9). Surprisingly, an added increase of 1-4° C. is observed for peptides 8, 10-12, suggesting a synergistic effect when multiple aza-glycines are incorporated.

To have a sense of how fast a "homo-azGly-peptide" folds into a triple helix, refolding kinetic CD experiment was performed on peptide 13 and 14. The two peptides, at a concentration of 0.2 mM in PBS buffer, were denatured at 95° C. for 15 min and their CD signals were monitored at 4° C. until both peptides recovered (>50%) ellipticity at 215 nm. Initial CD data were normalized into fraction refolded plots (FIG. 12D) from which half-refolding times ($t_{1/2}$) were obtained as the time values at which 50% of the peptide recovered triple helicity.[15] Determined $t_{1/2}$ values for 13 and 14 are 8±2 and 6±1 minutes respectively, much faster than the consensus control peptide 1 with a $t_{1/2}$ of 24±6 minutes.[16]

In summary, our study has provided valuable insights into the utility of aza-glycine incorporation in collagen-like peptides and the optimization of their physical properties. We have demonstrated that azGly has no strong positional preference with respect to the thermal stability it introduces in our model, and that the inclusion of multiple azGly residues synergistically facilitate the peptide on self-assembling into a triple helix. Peptides with all natural glycine replaced by aza-glycine result in the most stable structure at any given lengths and a 12-mer peptide can now initiate the process of self-assembly into a defined tertiary structure. In addition to insight into the fundamental importance of hydrogen bonding in natural systems, these studies may provide insight into diverse areas ranging from self-assembling materials and drug design to catalysis and synthetic receptors. Future directions include crystallographic trials, and the development of possible new biomaterials with properties alternative to those of conventional collagen-type fibrous materials.

REFERENCES FOR EXAMPLE 2

1. Anfinsen, C. B. *Science* 1973, 181, 223.
2. (a) Mirsky, A. E.; Pauling, L. *Proc. Natl. Acad. Sci. USA* 1936, 22, 439. (b) Pauling, L.; Corey, R. B.; Branson, H. R. *Proc. Natl. Acad. Sci. USA* 1951, 37, 205. (c) Pauling, L.; Corey, R. B. *Proc. Natl. Acad. Sci. USA* 1951, 37, 729.
3. (a) Hubbard, R. E.; Kamran Haider, M. In eLS; John Wiley & Sons, Ltd, 2001. (b) Deechongkit, S.; Nguyen, H.; Powers, E. T.; Dawson, P. E.; Gruebele, M.; Kelly, J. W. *Nature* 2004, 430, 101. (c) Fu, Y. W.; Gao, J. M.; Bieschke, J.; Dendle, M. A.; Kelly, J. W. *J. Am. Chem. Soc.* 2006, 128, 15948. (d) Pace, C. N. *Nat. Struct. Mol. Biol.* 2009, 16, 681. (e) Gao, J.; Bosco, D. A.; Powers, E. T.; Kelly, J. W. *Nat. Struct. Mol. Biol.* 2009, 16, 684. (f) Bowie, J. U. *Curr. Opin. Struc. Biol.* 2011, 21, 42. (g) Pedersen, S. W.; Pedersen, S. B.; Anker, L.; Hultqvist, G.; Kristensen, A. S.; Jemth, P.; Stromgaard, K. *Nat. Commun.* 2014, 5, 3215.
4. (a) Pauling, L.; Corey, R. B. *Nature*, 1951, 168, 550. (b) Pauling, L.; Corey, R. B. *Proc. Natl. Acad. Sci. USA* 1951, 37, 241. (c) Crick, F. H. C. *Nature* 1952, 170, 882. (d) Watson, J. D.; Crick, F. H. C. *Nature* 1953, 171, 737. (e) Crick, F. H. C.; Rich, A. *Nature* 1955, 176, 780. (f) Rich, A.; Crick, F. H. C. *Nature* 1955, 176, 915. (g) Chou, P. Y.; Fasman, G. D. *J. Mol. Biol.* 1977, 115, 135.
5. (a) Engel, J.; Bachinger, H. P. *Top. Curr. Chem.* 2005, 247, 7. (b) Shoulders, M. D.; Raines, R. T. *Annu. Rev Biochem.* 2009, 78, 929.
6. (a) Kusebauch, U.; Cadamuro, S. A.; Musiol, H.-J.; Lenz, M. O.; Wachtveitl, J.; Moroder, L.; Renner, C. *Angew. Chem. Int. Ed.* 2006, 45, 7015. (b) Wang, A. Y; Mo, X.; Chen, C. S.; Yu, S. M. *J. Am. Chem. Soc.* 2005, 127, 4130. (c) Rele, S.; Song, Y; Apkarian, R. P.; Qu, Z.; Conticello, V. P.; Chaikof, E. L. *J. Am. Chem. Soc.* 2007, 129, 14780. (d) Cejas, M. A.; Kinney, W. A.; Chen, C.; Leo, G. C.; Tounge, B. A.; Vinter, J. G.; Joshi, P. P.; Maryanoff, B. E. *J. Am. Chem. Soc.* 2007, 129, 2202. (e) Przybyla, D. E.; Chmielewski, J. *J. Am. Chem. Soc.* 2008, 130, 12610. (f) Yamazaki, C. M.; Asada, S.; Kitagawa, K.; Koide, T. *Biopolymers* 2008, 90, 816. (g) Fallas, J. A.; Gauba, V.; Hartgerink, J. D. *J. Biol. Chem.* 2009, 284, 26851. (h) Fields, G. B. *Org. Biomol. Chem.* 2010, 8, 1237. (i) Jiang, T.; Xu, C.; Zuo, X.; Conticello, V. P. *Angew. Chem. Int. Ed.* 2014, 53, 8367.
7. (a) J. A. M. Ramshaw, N. K. Shah, B. Brodsky, *J. Struc. Biol.* 1998, 122, 86-91. b) S. K. Holmgren, K. M. Taylor, L. E. Bretscher, R. T. Raines, *Nature*, 392, 666-667 (1998). b) J. A. Hodges, R. T. Raines, *J. Am. Chem. Soc.* 2003, 125, 9262-9263. (c) M. D. Shoulders, K. A. Satyshur, K. T. Forest, R. T. Raines, *Proc. Natl. Acad. Sci. USA* 107, 559-564 (2010). (d) J. A. Fallas, L. E. R. O'Leary, J. D. Hartgerink, *Chem. Soc. Rev,* 2010, 39, 3510-3527. (e) G. J. Bartlett, A. Choudhary, R. T. Raines, D. N. Woolfson, *Nat. Chem.* Biol. 6, 615-620 (2010). (f) Erdmann, R. S. & Wennemers, H. *J. Am. Chem. Soc.* 134, 17117-17124 (2012).
8. (a) Goodman, M.; Bhumralkar, M.; Jefferson, E. A.; Kwak, J.; Locardi, E. *Biopolymers* 1998, 47, 127 (b) C. L. Jenkins, M. M. Vasbinder, S. J. Miller, R. T. Raines, *Org Lett,* 7, 2619-2622 (2005). (c) N. Dai, F. A. Etzkorn, *J. Am. Chem. Soc.* 2009, 131, 13728-13732. (d) Y Zhang, R. M. Malamakal, D. M. Chenoweth, Angew. Chem. Int. Ed. 2015, 54, 10826-10832. (e) R. W. Newberry, B. VanVeller, R. T. Raines, Chem. Commun. 2015, 51, 9624-9627.
9. Y Zhang, R. M. Malamakal, D. M. Chenoweth. J. Am. Chem. Soc. 2015, 137, 12422-12425.
10. a) G. N. Ramachandran, M. Bansal, R. S. Bhatnagar, *Biochim. Biophys. Acta.,* 1973, 322, 166. b) E. Suzuki, R. D. B. Fraser, T. P. Macrae, *Int. J. Biol. Macromol.,* 1980, 2, 54. c) J. Bella, M. Eaton, B. Brodsky, H. M. Berman, *Science* 266, 75-81 (1994).
11. For synthesis of collagen model peptides, see Supporting Information.
12. Engel, J.; Chen, H. T.; Prockop, D. J.; Klump, H. *Biopolymers* 1977, 16, 601.
13. R. S. Erdmann, H. Wennemers, *Angew. Chem., Int. Ed.* 50, 6835-6838 (2011).
14. For synthesis of Fmoc-azGly-Pro-Hyp(tBu)-OH, see Supporting Information.
15. See the Supporting Information for details
16. Data taken from ref. 9.

Example 3: azPro Confers a Selective Stabilizing Effect to Aza-CMP Triple Helices Unnatural amino acid substitutions can provide a wealth of information about protein and peptide folding events. Collagen, the most abundant protein in the animal kingdom, has served as an important model system for unnatural amino acid substitutions due to its broad importance in human disease and use in constructing synthetic biomaterials.[1,2] Recently, we incorporated the unnatural amino acid Aza-Proline and demonstrated its utility as a stereodynamic replacement for proline to provide key insights into collagen peptide folding and recognition processes.[3] Previous reports by Raines and Miller established that substituting a glycine amide for either an ester or a trans alkene greatly destabilized the triple helical structure of collagen.[4] Etzkorn et al. demonstrated that substitution of any amide bond with (E)-alkene, regardless of whether it was involved in interchain hydrogen bonding, prevented triple helix formation even though the trans alkene locked the pseudo amide bond in a trans conformation.[5,6] Peptoid substitution by Goodman in the 90s, and thioamide incorporation into collagen mimetic peptides by the Raines group led to comparable or slightly more stable triple helix structures depending on the positions.[7-9] In 2015, we reported a hyperstable collagen peptide via aza-glycine substitution of a glycine residue, demonstrating a simple and effective way of stabilizing the collagen triple helix by addition of extra hydrogen bond donors at the helix interface.[10]

Our recent report on the replacement of a proline stereocenter with a nitrogen atom in a collagen model peptide resulted in stereochemical mimicry and a stable triple helix structure.[2] In our first report, we replaced the proline α-stereocenter in the Xaa position with a nitrogen atom (FIG. 13, peptide 3). When constrained in the triple helix form, the α□carbon of the proline in the Xaa position projects a hydrogen toward solvent. After replacement with nitrogen, the resulting lone-pair is also solvent exposed in the triple helix, providing an effective α□C stereochemical mimic in the Xaa position with an absence of unfavourable interactions. For the first time, this single result demonstrated the effect of stereodynamics[11] in the context of collagen triple helix assembly, however the positional and contextual dependence of stereodynamics remains to be investigated. The effect of neighboring hydroxyproline and the positional effects of AzPro substitution have not been studied. In addition, substitution of AzPro in the Yaa position remains to be investigated.

Herein we define the impact of AzPro incorporation on collagen triple helix self-assembly by addressing the following four unresolved questions. One, what is the effect of Aza-Proline substitution in the Y position of the collagen peptide chain? Two, what is the effect of hydroxyproline substitution on adjacent Aza-Proline stereodynamics? Three, what is the effect of AzaProline positional scanning along the collagen peptide chain? Four, what is the effect of incorporating multiple AzaProline residues into the collagen peptide chain? Collectively, the answers we provide to these questions shed light on the importance of stereochemical constraints in collagen peptide self-assembly and more broadly in biopolymer assembly and folding processes.

Results and Discussion

Aza-Proline Substitution in the Y Position:

To investigate the effect of AzPro replacement of a Y-position amino acid, peptide 4 (Ac-(POG)$_3$(PAzPG)(POG)$_3$-NH$_2$ (N-terminal acylated and C-terminal amidated)) was synthesized on solid phase (FIG. 14).

CD experiments revealed that peptide 4 remains in the monomer state based on the linear decrease in the CD signal as a function of increasing temperature. The effect of preventing triple helix formation runs counter to the result observed when aza-proline is incorporated at the Xaa position (FIG. 15). Examination of known crystal structures reveals two dramatically different micro-environments for the Xaa versus Yaa positions, as shown in FIG. 16. Although the proline α-center was solvent exposed in the Xaa position, the Yaa position orients the proline such that the α-CH is directed toward the interior of the central core. The exchange of the α-CH with N results in an unfavorable lone pair-lone pair repulsion with the same carbonyl involved in the collagen cross-strand hydrogen bond. The severe penalty for aza-proline substitution in the Yaa position highlights the intricate differences in the chemical environment at each position along the triplet. Intolerance for a C to N substitution in the Yaa position also illustrates the importance of avoiding lone pair-lone pair interactions at desolvated biopolymer interfaces.

Influence of Neighboring Hydroxyproline Substitution on Aza-Proline:

Next, we investigated using additional modification's to tune the refolding behavior of AzPro containing CMP. Previous studies have demonstrated that electronegative elements at the C-4 position of Yaa prolyl residue induces an exo pucker formation, which pre-organizes the φ, ψ angles and the cis-to-trans isomerization of the amide bond (ω).[1a,12] Earlier studies performed by Raines et al. suggest that a favorable n to π* delocalization can occur in the amide trans conformer due to a shorter distance between the oxygen lone pair and the π* of the carbonyl.[13] We investigated the effect of a neighboring hydroxyproline residue on the adjacent aza-proline with the thought that there could be a remote preorganizing effect transmitted through adjacent residues. hydroxyl group in a biological context where post-translational hydroxylationl[14] was employed to convert Pro (Yaa) to Hyp to thermodynamically and kinetically stabilize collagen (as shown for 1 and 2 in FIGS. 14 and 15).

To elucidate this effect, the corresponding Fmoc-AzPro-Hyp(tBu)Gly-OH SPPS building block was synthesized via a solid-phase assisted route (for synthesis, see S. I.). Then, the trimer unit was installed onto the growing peptide on a Rink Amide resin to construct the 21 amino-acid long collagen model peptide. Resulting peptide 5 was purified by HPLC and incubated at a concentration of 0.2 mM in PBS buffer (pH 7) for 24 h. Peptide 2 was also prepared to serve as the natural control group. (see FIG. 15 below dashline). The CD wavelength scan of peptide 5 exhibited a characteristic maximum at approximately 224 nm and a minimum at approximately 195 nm. This result indicates a possible highly organized collagen triple-helical conformation. However, because the unfolded single PPII-type chain also exhibits similar trends, a thermal denaturation experiment was performed to confirm the triple helix formation. Upon heating at a constant rate, the solution of peptide 5 exhibited a cooperative transition with a Tm of 39° C., which is one degree less stable than natural peptide 2, (POG)$_7$, but 3° C. higher than that of the AzPro containing peptide that lacks a central Hyp residue (peptide 3) (FIG. 15). This result indicates that due to the presence of Hyp, the AzPro containing trimer exhibited a thermal stabilization that was more than that of the "natural" ProProGly trimer unit (i.e., peptide 1).

Next, we investigated the effect of this modification on the refolding kinetics of the collagen model peptide. Peptide solutions were heated at 80° C. to achieve denaturation. Then, these solutions were transferred to a pre-cooled CD cuvette. The ellipticity was monitored as a function of time with a dead time of approximately 65 s. Then, the obtained data were plotted as the fraction refolded. The time required to reach 50% re-assembly was defined as $t_{1/2}$. In a host-guest system, this value indicates the contribution of the central triplet unit to the overall assembly. The results indicate that peptide 5 folds much faster than corresponding peptide 3, which lacks a central hydroxyproline (FIG. 15). Therefore, the neighboring Hyp dramatically enhanced the folding rate of the collagen model peptide that contained a stereodynamic center.

To estimate the free energy differences associated with aza-proline incorporation, hysteresis studies were performed according to previously reported protocols. (see ref. 14-16 and supporting information). The results are shown in FIG. 15. A more favorable AG was observed for peptide 5 compared to that for 3, and this results is similar to that observed for the two 'natural' control peptides (1 and 2).

Aza-Proline Positional Scanning:

Then, we investigated the possibility of a positional difference in (AzProHypGly) in the collagen peptide sequence. The AzPro-Hyp-Gly trimer was scanned at six different positions with peptide 5, which contained a trimer in the center of a total 7 trimer unit as the new 'control' compound (FIG. 17A) As shown in FIG. 17, the AzPOG trimer destabilized the collagen model peptide to a greater extent when it was located closer to the N- or C-termini. This behavior is different from that of other proline derivatives, which typically cause more destabilization in the center.[17,18] Therefore, the fluxional dynamic moiety is best tolerated in an environment where the neighboring groups aid in the organization of the main chain dihedral angles. In terms of the refolding kinetics, as the AzPOG triplet was shifted towards the terminal, AzPro decreased the rate of trimer assembly for peptide 6, and 9 and 10 exhibited a refolding rate that was faster or within the range of control peptide 2. However, the lower stability associated with these peptides, which may adopt a loosely packed overall structure, may contribute to the rapid refolding behavior. The refolding results indicate no clear difference for the mutation being closer to the N or C terminus, which is in agreement with the results from a previous study where a synthetic collagen model peptide that lacked a trimerization domain initiated association from either side with at least two (POG) units.[19] As the number of (POG) units increase, the assembly becomes faster.

Multiple aza-Proline residues: Finally, we determined the number of stereodynamic center (i.e., AzProHypGly trimer) that can be incorporated into a collagen model peptide without perturbing the triple-helix formation. Three peptides with two or three aza-prolines (11-13) were synthesized, and none of these peptides exhibited a triple helical formation in our investigation. The results indicate that the number of the trimer is limited to no more than one even though AzPOG has a higher host-guest thermal stability than the "natural" PPG. We attribute this phenomenon to the high entropic cost introduced by the flexible nitrogen atom.

Conclusion:

In summary, we have defined the impact of AzPro incorporation on collagen triple helix self-assembly by answering four key questions. First, we demonstrated the importance of avoiding lone-pair lone-pair interactions at desolvated interfaces by showing that AzPro substitution in the Yaa collagen triplet position precludes self-assembly. Second, a remote preorganizing effect was observed when AzPro was incorporated adjacent to hydroxyproline. This result hints at the possibility of a remote preorganizing effect induced by the hydroxyproline post-translational modification in addition to the inherent stereoelectronic effects. Third, we observed that triple helix stabilization is maximized for AzPro substitution at the central triplet position and destabilizes by as much as 10° C. as the substitution is moved toward the N or C terminus. Additionally, the rate of self-assembly was slowest for substitution at the three central positions and more rapid toward the termini, where initial triple helix nucleation is critical. This result reflects the increased configurational entropy present in the AzPro stereodynamic probe versus the fixed proline stereocenter, providing a unique way to probe biopolymer systems. Fourth, The effect of incorporating multiple AzPro residues was found to completely abrogate triple helix self-assembly, also a reflection of increased configurational entropy, except in this case from multiple stereodynamic probes. Taken together, these results defined the impact of AzPro incorporation on collagen triple helix self-assembly and set the stage for the use of AzPro as a stereodynamic probe in future studies of biopolymer assembly and folding.

REFERENCES FOR EXAMPLE 3

1. (a) Shoulders, M. D.; Raines, R. T. *Annu. Rev Biochem.* 2009, 78, 929. (b) Engel, J.; Bächinger, H. P. *Top. Curr. Chem.* 2005, 247, 7. (c) Fallas, J. A.; O'Leary, L. E. R.; Hartgerink, J. D. *Chem. Soc. Rev,* 2010, 39, 3510-3527.
2. (a) Tuckwell, D. S.; Ayad, S.; Grant, M.; Takigawa, M. E.; Humphries, M. J. *J. Cell Sci.,* 1994, 107, 993. (b) Kalluri, R. *Nat. Rev Cancer,* 2003, 3, 422. (c) Lauer-Fields, J. L.; Juska, D.; Fields, G. B. *Biopolymers,* 2002, 66, 19. (d) Ricard-Blum, S.; Ruggiero, F.; van der Rest, M. *Top. Curr Chem.* 2005, 247, 35. (e) Byers, P. H. *Philos. Trans. R. Soc,* B 2001, 356, 151-157. (f) Myllyharju, J.; Kivirikko, K. I. *Trends Genet.* 2004, 20, 33-43.
3. Zhang, Y; Malamakal, R. M.; Chenoweth, D. M. *Angew. Chem. Int. Ed.* 2015, 54, 10826-10832.
4. Jenkins, C. L.; Vasbinder, M. M.; Miller, S. J.; Raines, R. T. *Org Lett,* 2005, 7, 2619-2622.
5. Dai, N.; Wang, X. J.; Etzkom, F. A. *J. Am. Chem. Soc.* 2008, 130, 5396-5397;
6. Dai, N. Etzkom, F. A. *J. Am. Chem. Soc.* 2009, 131, 13728-13732.
7. Goodman, M.; Melacini, G.; Feng, Y *J. Am. Chem. Soc.* 1996, 118, 10928.
8. Goodman, M.; Bhumralkar, M.; Jefferson, E. A.; Kwak, J.; Locardi, E. *Biopolymers* 1998, 47, 127
9. R. W. Newberry, B. VanVeller, R. T. Raines, *Chem. Commun.* 2015, 51, 9624-9627.
10. Zhang, Y; Malamakal, R. M.; Chenoweth, D. M. *J. Am. Chen. Soc.* 2015, 137, 12422-12425.
11. Lambert, J. B. *Organonitrogen Stereodynamics, Vol. 1,* 1st ed., VCH, New York, 1992. (a) Holmgren, S. K.; Taylor, K. M.; Bretscher, L. E.; Raines, R. T. *Nature,* 1998, 392, 666-667. (b) Hodges, I. A.; Raines, R. T. *J. Am. Chem. Soc.* 2003, 125, 9262-9263. (c) Kotch, F. W.; Guzei, I. A.; Raines, R. T. *J. Am. Chem. Soc.* 2008, 130, 2952-2953. (d) Shoulders, M. D.; Satyshur, K. A.; Forest, K. T.; Raines, R. T. *Proc. Natl. Acad. Sci. USA* 2010, 107, 559-564.
12. (a) Choudhary, A.; Gandla, D.; Krow, G. R.; Raines, R. T. *J. Am. Chem. Soc.* 2009, 131, 7244-7246. (b) Bartlett, G. J.; Choudhary, A.; Raines, R. T.; Woolfson, D. N. *Nat. Chem. Biol.* 2010, 6, 615-620. (c) Jakobsche, C. E.; Choudhary, A.; Miller, S. J.; Raines, R. T. *J. Am. Chem. Soc.* 2010, 132, 6651-6653; (d) Newberry, R. W.; VanVeller, B.; Guzei, I. A.; Raines, R. T. *J. Am. Chem. Soc.* 2013, 135, 7843-7846; (e) Choudhary, A.; Newberry, R. W.; Raines, R. T. *Org. Lett.* 2014, 16, 3421-3423; (f) Newberry, R. W.; Bartlett, G. J.; VanVeller, B.; Woolfson, D. N.; Raines, R. T. *Protein Sci.* 2014, 23, 284-288;
13. (a) Berg, R. A.; Prockop, D. *J. Biochem. Biophys. Res. Commun.,* 1973, 52, 115. (b) Inouye, K.; Kobayashi, Y; Kyogoku, Y; Kishida, Y; Sakakibara, S.; Prockop, D. J. *Arch. Biochem. Biophys.,* 1982, 219, 198.
14. Erdmann, R. S.; Wennemers, H. *Angew. Chem., Int. Ed.* 2011, 50, 6835-6838.

15. Mizuno, K.; Boudko, S. P.; Engel, J.; Bachinger, H. P. *Biophys. J.* 2010, 98, 3004-3014.
16. Erdmann, R. S.; Wennemers, H. *J. Am. Chem. Soc.* 2012, 134, 17117-17124.
17. Ramshaw, J. A. M.; Shah, N. K.; Brodsky, B. *J. Struc. Biol.* 1998, 122, 86-91.
18. Chen, Y. S.; Chen, C. C.; Horng, J. C. *Biopolymers* 2011, 96, 60.
19. Buevich, A. V.; Silva, T.; Brodsky, B.; Baum. J. *J. Biol. Chem.* 2004, 279, 46890-46895.

Example 4: Crystal Structures of an Exemplary Aza-CMP Triple Helix Complex

Collagen is an essential protein in mammals, providing structure to skin, bones, cartilage, and the extracellular matrix. Native collagen is characterized by the variable amino acid sequence XYG. The variable X and Y positions in the XYG tripeptide are typically occupied by proline and hydroxyproline, respectively. Conversely, glycine is strictly conserved, and glycine mutations can propagate structural instability and collagen-related disease. This hallmark sequence promotes collagen's self-assembly into a distinctive triple helical supramolecular structure. However, it has been shown that certain synthetic modifications can lead to useful and intriguing biomechanical properties in collagen model peptides (CMPs). Recently, we reported that replacing a single α-carbon of glycine with a nitrogen atom (substituting glycine for aza-glycine) in a CMP leads to significantly enhanced triple helix stability. In an effort to understand this increased stability, our previous molecular dynamics (MD) calculations pointed toward the possibility of a new hydrogen bond to aza-glycine (azGly or azG) from one of two carbonyls on adjacent peptide strands or a bifurcated hydrogen bond to both, in addition to the canonical cross-strand hydrogen bonds already present in collagen. This possible enhancement of collagen's native hydrogen bonding motif warranted further investigation. In addition, MD simulations performed in conjunction with the XRD analyses are useful in the structural characterization of these higher-order mini-protein structures.

In Example 1 above, we demonstrated that a single azGly substitution placed at the central location of a 21-mer peptide resulted in significant stabilization of the collagen triple helix. In a separate study we demonstrated that the incorporation of multiple azGly residues resulted in additive stability with synergistic effects when adjacent. In addition, fully azGly-substituted peptides were stable even at minimal lengths. These previous studies incorporated azGly residues in all POG and PPG-containing collagen peptides. However the ability to use azGly stabilization with alternate residues could be extremely important for many areas such as structural biology of protein-collagen interactions.

Peptide Synthesis and Purification:

We synthesized control peptide 1, $(POG)_3$-PRG-$(POG)_4$, and its azapeptide analog 2, $(POG)_3$-PRazG-$(POG)_4$ (FIG. 19, bottom) using solid-phase peptide synthesis (SPPS). The peptides were pre-pared on Rink amide resin using a fluoroenylmethoxycar-bonyl chloride (Fmoc) protecting group. The tripeptide synthon Pro-Hyp-Gly (Fmoc-PO(tBu)G-OH) was prepared in-house for use as the primary SPPS building block. This allowed for greater efficiency and higher yields by lowering the total number of reaction steps. AzGly was integrated into 2 by coupling with Fmoc-hydrazine (Fmoc-NH—NH$_2$). The side-chain protecting groups for Arg and Hyp were 2,2,4,6,7-pentamethyldihydrobenzofuran-5-sulfonyl (Pbf) and tert-butyl (tBu), respectively. The completed peptides were cleaved from the resin by mixing with a cleavage cocktail of trifluoroacetic acid (TFA), phenol, H2O, and ethane-1,2-dithiol (EDT) in an 87:5:5:3 (v/v) ratio for 1.5 h.

Following SPPS, the peptides were precipitated in cold ether and purified using preparative reverse-phase high-performance liquid chromatography (HPLC) with a mobile phase gradient of 10-20% acetonitrile in H$_2$O (Phenomenex Luna C$_1$8(2) column, 5 µm particle size, 100 Å pore size). The chromatographic fractions were analyzed by matrix-assisted laser desorption/ionization time-of-flight mass spectrometry (MALDI-TOF MS) and lyophilized for maximum purity.

Thermal Stability and Folding Kinetics:

In order to examine the enhancement of thermal stability due to azGly substitution, peptides 1 and 2 were heated at 12° C./h to induce gradual unfolding of the triple helix. The change in molar ellipticity, 0, of each peptide was monitored by circular dichroism (CD) spectroscopy. The resulting curves (FIG. 20A) were analyzed using JASCO Spectra Man-ager software (JASCO, Inc., Easton, Md.) in order to determine their respective thermal transition temperatures, Tm. Comparison of these data for 1 and 2 indicated an increase in Tm of 8.8° C. as a result of the enhanced stability imparted by the azGly residue in 2.

Furthermore, the kinetics of triple helical self-assembly for 1 and 2 were also analyzed by CD. Samples of each peptide were incubated overnight at 4° C. in PBS (0.2 mM). Solutions were denatured at 80° C. for 15 min and then quickly transferred to the CD spectrophotometer, which was held at 4° C. The gradual increase of θ was monitored and used to calculate t½, the time at which the peptide regained 50% of its initial triple helicity (FIG. 20B). The results of this experiment indicated that the t½ of 2 is 13.0 min shorter than that of 1, denoting more efficient folding kinetics as a result of azGly substitution.

Peptide Crystallization and X-Ray Diffraction:

We attribute the extra stability conferred by additional azGly insertion to the added H-bond network positioned at the desolvated interface of the three collagen peptide strands. Each azGly residue adds one extra hydrogen bond donor to the peptide sequence. To investigate this bonding motif in more detail, we crystallized peptide 2 using a sitting-drop vapor diffusion methodology adapted from Okuyama et al. Briefly, a peptide stock solution was prepared by dissolving the purified solid product in 18 MΩ H$_2$O to a final concentration of 8.4 mg/mL as verified by UV-vis spectroscopy. Crystal trials were prepared by combining 1 µL of the peptide solution with 1 µL of a reservoir solution of 0.095 M Tris-HCl (pH 7.6), 30% (w/v) PEG4000, and 0.01 M Li$_2$SO$_4$.H$_2$O. Trays were incubated at 4° C., and crystals became visible within approximately 1 week. Crystals were cryoprotected in 30% (w/v) PEG4000 before final freezing in liquid N$_2$.

Structural Refinement and Analysis:

In order to more precisely quantify the influence of azGly substitution on the triple helical structure of this CMP system, the data collected during XRD was refined using the CCP$_4$ software suite. (FIGS. 21 and 22). Moreover, the positional preference and effect of incorporating multiple aza-glycine substitutions in collagen model peptides was explored. For example, the atomic resolution of peptide sequence $(POG)_3(PRazG)(POG)_4$ was found to yield an atomic resolution (1.13 Å) crystal structure (FIG. 5). This crystal structure provides a model by which other Arg-containing CMPs can be crystallized and compared. These results further support the generality of the enhanced stability imparted by azGly substitution by verifying its viability in a CMP system containing Arg, a relatively infrequent residue in native collagen sequences. To this end, this project will also explore azGly substitution in other unconventional CMPs, as well as the influence of substituting all Gly residues in a CMP containing unnatural residues with azGly. Furthermore, the ability to synthesize and characterize the structure hyperstable CMPs containing unnatural residues provides the freedom to explore the binding of any given collagen sequence by a range of proteins and other biomolecules.

Conclusion:

In summary, an azapeptide analog of a 24-mer Arg-containing CMP was synthesized on solid phase by substituting a central Gly atom with azGly. This integrated an additional hydrogen bond donor to each strand of the triple helix, which in turn propagated increased thermal stability and faster folding kinetics. The structural basis for this increased stability was verified by using XRD to produce an atomic resolution crystal structure for the azapeptide. These results further support the generality of the enhanced stability imparted by azGly substitution by verifying its viability in a CMP system containing Arg, an uncommon residue in native collagen. To this end, azGly substitution in other unconventional CMPs, as well as the influence of multiple azGly substitutions within a single CMP containing unnatural residues are all contemplated. These collagenous azapeptide sequences will provide the basis for biomaterials in applications where tunable hyperstability would provide crucial enhancements in performance, such as chronic wound healing and controlled release drug delivery.

Example 5: Precision Scaffold Using Aza-CMPs

In this example, the central hypothesis is that side chain functionalized collagen peptides can be utilized as a supramolecular scaffold to create new classes of multi-chromophore assemblies with unique and emergent photophysical properties. When chromophores lie within close proximity to one another, they can act collectively form molecular excitons when excited. The electronic wavefunction associated with molecular excitons is delocalized over the individual contributing units, which gives rise to unique photophysical properties that are more than the sum of the individual parts. For example, shifts in the linear absorption spectrum may be observed that are associated with the excitonic states. Depending on the molecular geometry, the optically active excitonic states will be either red-shifted or blue-shifted with respect to the absorption of the individual chromophore, and in some cases, both of these excitonic states can be optically active. The spectral shift in the linear absorption spectrum is directly proportional to the interaction between the transition dipole moments of the individual chromophores (the electronic coupling, V). We envision collagen as providing a scaffold for precisely controlling excitonic states in chromophore assemblies (FIG. 23). The collagen scaffold provides an opportunity for chromophore spacings very similar in distance (~9 angstroms) to the pigments in natural photosynthetic proteins. FIG. 24 shows a depiction of the collagen based multichromophore assemblies that we envision with distance measurements from potential points of conjugation for chromophore attachment (FIG. 23).

The addition of functionalizable side chains of the hydroxyl group of hydroxyproline can be optimized and utilized to construct a collagen based supramolecular scaffold for organizing functional molecules. We have already tested a two-carbon linker containing a primary amine, and this system exhibited very encouraging results. We have worked out the monomer synthesis and established expertise in the laboratory for the synthesis of substituted hydroxyproline building blocks. We will vary the linker region by extending the aliphatic chain and adding aromatic groups to determine the impact on the self-assembly process. This objective will identify a set of side chains (linkers) that can be applied for conjugation chemistry, and we will assess their impact on the self-assembly process. To start, we will focus on linker regions terminated with primary amines due to their reliability for conjugation chemistry with activated acids.

We will synthesize multi-chromophore assemblies using collagen model peptides as a scaffold. We have already tested this idea, as shown in our preliminary data presented in the following section, and we are now ready to build collagen model peptides with a range of different chromophores. We will conjugate several types of organic chromophores commonly utilized in model systems of multi-chromophore assemblies as well as new chromophores recently developed in our laboratory. Pyrene will be conjugated due to its propensity for excimer formation. For this approach, pyrene carboxylic acids will be attached to the primary amine of the functionalized collagen peptides (FIG. 23 and FIG. 24). A series of red-shifted dyes will also be conjugated based on commercially available Rylene dyes. With the demand for fluorescent probes in the biological sciences, numerous pre-activated fluorescent probes are readily available for reaction with amines. These probes may be advantageously used to examine a broader selection of fluorescent conjugates. Pyrene chromophores will be used to probe the proximity of the dyes through the possibility of excimer emission from closely interacting chromophores, and these model studies will be combined with theory to develop a deeper understanding of the system as well as the effect of dye positioning on the photophysical properties of the assembled structures. These experiments will be conducted with a panel of linkers consisting of different lengths and functionalities to produce indirect information about the impact of the linker on chromophore spatial positioning from the excimer emission. The chromophores will be conjugated via an active ester version of the dye. This approach involves standard chemistry that we have already worked out, as shown in the preliminary data section. With a set of dye labeled collagen peptides in hand, we will characterize their self-assembly properties and photophysical behavior in the assembled and denatured form. New photophysical behavior in the triple helix form due to precise periodic arrangement is expected. In addition to homotrimeric assemblies, we will explore heterotrimeric assemblies containing donor and acceptor dyes. This study will be initially conducted by varying the mole fraction of the different components and characterizing its effect on the spectroscopic properties. Self-sorting is a possibility in these systems and will be very interesting if observed. We will also systematically vary the position and spacing between the dyes along the collagen backbone. UV-Vis and fluorescence spectroscopies will be utilized in conjunction with CD and other techniques in the RLBL. The kinetics and thermodynamics of the self-assembly process will be used in conjunction with the photophysical properties and systematic structural modification to gain insight into the assemblies. TD-DFT calculations will be performed on the individual chromophores to determine the optically active electronic excited states and their corresponding transition dipole moments. From the MD simulations we will determine the most likely ground state configurations associated with the chromophores to predict the inter-chromophore distances. From the calculated transition dipole moment and distances, we will determine the electronic coupling. We will also use the results from the MD simulations and DFT calculations to model the linear absorption spectrum and make predictions regarding the positioning for future experiments.

Additional experiments will include the generation of thiol-terminated versions of the peptide-chromophore conjugates for the fabrication of self-assembled monolayers of donor and acceptor dyes on gold (Au) electrodes. These systems will be used to evaluate their potential in photovoltaic applications by measuring the photocurrent generation of the assemblies. The collagen assemblies should be uniquely suited for this because they can provide a vertically aligned coaxial arrangement of chromophore assemblies on the gold surface. Photoelectrochemical measurements will be evaluated using an electrochemical analyzer and a Xe light source, and the light intensity will be monitored with an optical power meter.

We have already synthesized unnatural hydroxyproline amino acid residues with a two-carbon linker containing chromophore conjugation domains. In preliminary studies, these unnatural residues have been incorporated into collagen peptides, and we have demonstrated that they retain the ability to self-assemble into a triple helical structure using CD spectroscopy. These systems exhibit a cooperative unfolding curve with an inflection point of 51° C. for melting of the triple helical form, which indicates minimal destabilization from side chain modification. This result gives us our first benchmark and paves the way for a broader study of linker length and functionality incorporated into the linker. In addition, this result provides a starting point for constructing chromophore assemblies. We also have initial results demonstrating that linker length is very important for the photophysical properties of chromophore-chromophore interactions.

We were able to successfully conjugate both methoxy coumarin and pyrene derivatives at all 3 positions on a collagen peptide, and using CD and fluorescence spectroscopy, we demonstrated that a stable triple helix is formed (FIG. 25). In addition, we observed very interesting properties in the chromophore assembly compared to those of the denatured single strand. In the triple helical assembly, a pronounced increase in brightness was observed based on fluorescence denaturation studies (FIG. 25). The triple helical assembly containing a total of 9 coumarin dyes was determined to be 2.4 times brighter than a single peptide strand containing 3 dyes and 3.3 times brighter than a single coumarin dye. In addition to the increase in brightness, a 60 nm bathochromic shift was observed in the emission maximum from 398 nm to 458 nm. This shift has not been previously observed for coumarin dyes of this kind. With optimal chromophore spacing, we expect to achieve an increase in brightness of >5 times that of a single chromophore. We also expect that chromophore optimization for high quantum yield, high extinction coefficient, and large stokes shift will also significantly improve the brightness by helping to prevent chromophore-chromophore reabsorption. We are currently performing more photophysical studies on the coumarin system and expanding our studies to other chromophores. In addition to coumarin, we also have preliminary results on pyrene-collagen chromophore assemblies that contain a total of 9 dyes (3 per collagen strand). Self-assembly of these peptides results in highly efficient excimer formation, as shown in FIG. 25. These preliminary results are very exciting and validate the ideas proposed in this application.

Methods and Techniques:

Traditional organic synthesis may be used to construct the building blocks or unnatural amino acids. Then, solid-phase peptide synthesis may be used to build the peptides needed for key studies. A summary of methods is given below.

Synthesis: Small Molecule Building Blocks & Peptides:

Small molecule building blocks (unnatural amino acid monomers) and peptides will be synthesized by standard procedures.

Small Molecule & Peptide Purification & Characterization:

Small molecule purification will be carried out using standard chromatography and crystallization methods. The peptides will be purified by standard HPLC and precipitation methods. HPLC at multiple wavelengths will aid in the identification and verification of the number of chromophores attached to each collagen peptide. Standard mass spectrometry techniques, such as MALDI-MS and ESI, will be used to verify the molecular weight of the synthesized peptides and small molecules. All of the small molecule building blocks will be characterized by standard techniques to establish identity and purity.

Self-Assembly Thermodynamics & Kinetics:

CD spectroscopy will be used to follow the assembly and disassembly process and obtain thermodynamic and kinetic information. In addition, temperature dependent fluorescence spectroscopy will be used along with a new stopped-flow kinetics instrument recently acquired by our department. With this instrument, we have the capability of working in UV or fluorescence mode.

Structural Characterization:

Structural characterization will be carried out using NMR and X-ray techniques. Other techniques that will be used to look for ordered assemblies and higher order structures include AFM and TEM. Structural characterization by NMR is possible using instruments available in the chemistry department, and our group has begun to apply these methods.

Photophysical Property Characterization:

Photophysical properties will be evaluated by standard UV-Vis and fluorescence spectroscopy based methods, including transient absorption spectroscopy, multi-dimensional infrared spectroscopy, pump-probe spectroscopy, and optical triggering experiments at the UPenn Regional Laser Biomedical Technology Laboratory (RLBL).

Example 6: Aza-CMP is Resistant to Collagenase

The above examples have demonstrated that aza-CMPs possess enhanced thermal stability compare to natural collagen peptides. However, in the above examples, a question remains as to whether the enhanced thermal stability also translates to enhanced collagenase resistance. In this example, it was discovered that aza-CMPs do indeed show enhanced resistance to collagenases. Moreover, the inventors had also demonstrated that the enhanced collagenase resistance is not due to the improved thermal stability but is rooted in the chemical ligation caused by simple C to N mutation in the aza-amino acid residues.

As shown in FIGS. 31-36, incorporation of aza-Glycine into collagen peptides renders the peptides completely resistant to degradation by collagenase enzymes. The experiments conducted in these figures uses purified collagenase I from Worthington Biochemical Corporations (product code CLSPA, cat no. LS005275, LS005273, LS005277).

Starting with FIG. 31-35, we showed that in a 12mer CMP in which all G are replaced with azG, the aza-CMP is completely resistant to collagenase. In FIG. 36, we further showed that the resistance holds regardless of the secondary/tertiary structure of the peptide. This indicates that the resistance is not due to the enhanced thermal stability but to the C to N substitution.

This is a really important result because you can now use aza-Gly incorporation into collagen peptides for site-specific blocking of enzymatic degradation. Exemplary utilities for this discovery may include:

Use of the aza-CMPs as a tool for structural biology. For example, incorporation of aza-amino acid may facilitate co-crystalization of catalytically active forms of important enzymes such as MMP's involved in cancer. The current strategies for co-crystallizing MMP's all rely on making a catalytically inactive mutant enzyme. Incorporating aza-amino acids into the proteins or peptides offers a new strategy to obtain structures with the active enzymes, which was previously difficult if not impossible to do.

A general strategy for designing inhibitors: of cancer-related proteins/proteases that act on collagen. Peptide fragments or currently known inhibitors that have glycine could just be substituted with aza-Gly to obtain new or more effective inhibitors.

Applications in collagen-based imaging probes that don't readily degrade: azapeptides could be used to image things like tumor microenvironments without the problem of MMP degradation.

Due to the ability of azapeptides to resist collagenase degradation, those skilled in the art will recognize that aza-CMPs of the present invention are not limited to the above exemplary uses, but will find general applicability in biomaterials design where collagenase degradation is a problem.

Example 7: Multichromophore Systems Using Aza-CMP Scaffold

Self-Assembly of Multi-Chromophore Systems:

Multi-chromophore systems offer unique advantages compared to their monomeric counterparts primarily due to their ability to produce novel photophysical properties through interactions between subunits.[13, 48] Nature has demonstrated the powerful utility of multichromophore systems, especially with regard to photosynthetic proteins and their associated chromophore assemblies. Proteins in biological systems arrange pigments with a high degree of specificity to optimize the collection of light energy and its transformation to chemical energy.[13,49] In an effort to expand the utility of these systems, many researchers have developed novel methods for organizing chromophores in artificial systems with the hopes of optimizing light harvesting and energy transfer properties. These methods typically fall into two categories as follows: covalent and noncovalent assemblies. Noncovalent assemblies are governed by intermolecular interactions, and therefore, these assemblies are advantageous in producing very large chromophore arrays. One approach for building self-assembled chromophores involves the creation of amphiphilic substrates that exploit solvophobic interactions.[50] This concept has been readily applied to perylene bisimides, where substitution of the imide or the aromatic core with hydrophilic side chains, such as PEG, resulted in rapid aggregation.[12,51] Substitution of the side chains with varying degrees of branching or functionality allows for control over the aggregation and optical properties of the structure. Another interesting approach for self-assembly has been the utilization of ion-ion interactions, which has been employed for construction of supramolecular assemblies of porphyrin rings.[50] In addition, other intermolecular interactions, such as hydrogen bonding, have often been exploited to aid the organization of i-conjugated molecules.[52] While noncovalent approaches are attractive from the viewpoint of ease of synthesis, a common disadvantage to this approach is that precision in the assembly of the chromophores is often lacking.[48] In an effort to remedy this shortcoming, researchers have experimented with using polymers to template specific arrangement. Numerous backbones have been constructed for this purpose with each utilizing various combinations and degrees of the aforementioned intermolecular interactions.[53] In addition to these unnatural polymer backbones, researchers have also investigated using natural biopolymers for chromophore arrangement, and DNA has been extensively investigated as a promising scaffold. One strategy used by Meijer and Schenning involved arranging various chromophores via hydrogen bonding interactions with thymine residues attached to a single strand of DNA.[54] Another approach was discovered by Armitage and co-workers, who found that certain chromophores could be intercalated within the base pairs of DNA to generate highly fluorescent dye assemblies while avoiding adverse effects from self-quenching.[55] Although these noncovalent approaches have made great strides over the last decade, their transient lifetimes and nonspecificity favor the formation of covalent chromophore assemblies. DNA has been extensively used to create covalent multichromophore assemblies. Strategies range from the replacement of nucleobases and the substitution of nucleotides or backbone to the complete removal of the nucleosides and replacement with a phosphate substituted chromophore.[48,56] A potential issue in the utilization of the scaffolds detailed above for chromophore assembly involves carefully balancing maximum chromophore incorporation while retaining the capacity for self-assembly of compact and stable structures. Methods for overcoming this obstacle have involved modification of chromophore interactions through the addition and variation of different types of linkers or modification of the chromophores to optimize stacking interactions.[48] Continued research is required to discover novel techniques for precisely arranging chromophores to optimize electron transport and optoelectronic properties through self-assembly and for the discovery of new and unique properties that only emerge from uniquely ordered structures, which can be difficult to predict a priori or through the use of computational methods.

As discussed herein, collagen model peptides self-assemble into topologically unique supramolecular scaffolds with advantages over existing scaffolds for chromophore assembly. Although nucleic acids have been extensively utilized in the self-assembly of soft materials, proteins have been drastically underutilized. Currently, much interest has been focused on programmable protein materials, and collagen represents a unique protein scaffold that has received little attention as a template for the construction of nanoscale materials and multi-chromophore assemblies. To date, only one recent example reported the attachment of chromophores to a polyproline peptide (Chem Rev. 2014 Apr. 23; 114(8): 4564-4601., the content of which is incorporated herein by reference). However, polyproline peptides are not capable of triple helical self-assembly, and we do not consider this study relevant to the proposed work. Collagen peptides share the same ease of synthesis as DNA as well as many of its positive attributes, such as water solubility and tunable self-assembly properties. One major advantage of collagen over nucleic acids is the added possibility of self-assembly in organic solvents in addition to water, not possible with nucleic acid scaffolds. As a biological scaffold, much research has been focused on investigating the tolerance of collagen self-assembly to various amino acid perturbations, providing many options for rational modification.[24, 27, 57, 58] The unique trimeric assembly of the collagen triple helix allows for new and novel high-density arrangements of chromophores. Covalent attachment of chromophores also allows for precise control over spatial positioning and valency. These new chromophore arrangements are expected to give rise to unique collective photophysical properties that are more than the sum of the individual parts, analogous to natural multichromophore systems. Discovering new and useful optical properties from collagen multichromophore assemblies will have a broader impact in many areas.

Accordingly, the present invention further provides new and novel approaches for controlling and tuning the stability of collagen triple helical assemblies using single atom backbone substitutions. The tolerance of the scaffold to chromophore addition and placement is determined as well as the effect of self-assembly on their optical properties. The invention provides tunable and thermally responsive self-assembled multichromophore materials. The attachment of a photosensitizer at the terminus of the light-harvesting antenna could also provide insight into the energy transfer mechanisms and efficiency of these systems. Chromophore assemblies have broader impacts on the ability to create light harvesting materials for artificial photosynthetic pathways[12, 49] and brightly fluorescent compounds for imaging applications[55,59,60] that may have potential for use in solar energy conversion for photovoltaic devices.[61-63] The insight gained from this particular scaffold can also be applied to other polymeric scaffolds, thereby collectively contributing to the general understanding of how these photonic assemblies function and the general knowledge base for building new functional assemblies.

Accordingly, the present invention provides triplets comprising chromophores. As for the aza-amino acids, these are also incorporated via triplets (again, generally of combinations of glycine, proline and hydroxyproline, with additional amino acids also included if tolerated). As will be appreciated by those in the art, the placement of the chromophore within the collagen monomer peptide can vary. In some cases, it is in an "internal" position, e.g. not on either the N- or C-terminus of the peptide monomer (although as described herein, there can be additional groups on the termini that are not amino acid derived). For example, in the case of a 21mer, the -L-Ch group (the linker and chromophore, generally linked via the oxygen atom of hydroxyproline, (e.g. "O-L-Ch") as further described below) can be in the center triplet ((AA)$_3$-OL-Ch-AA-AA-(AA)$_3$, (AA)$_3$-AA-OL-Ch-AA-(AA)$_3$ or (AA)$_3$-AA-AA-OL-Ch-(AA)$_3$, for example. Alternatively, the O-L-Ch can be at a peptide terminus (again, there can be additional groups on the termini that are not amino acid derived). Stated differently, when the collagen monomer comprises only proline (including hydroxyproline) and glycine, suitable L-Ch-triplets are selected from the group consisting of O-L-ChPG, O-L-ChGP, O-L-ChGO, PO-L-ChG, OO-L-ChG, GO-L-ChO, GO-L-ChP, GPO-L-Ch, GOO-L-Ch, OGO-L-Ch and PGO-L-Ch.

As above, it should be noted that most of the structures herein depict triplets of proline, hydroxyproline and glycine in various combinations. However, as will be appreciated by those in the art, additional amino acids can be included in the structures of the invention, as long as the ability to self-assemble into triplexes is not destroyed. Thus, for example, in some embodiments, different amino acids (including both naturally occurring and non-naturally occurring) may be used in a site specific way to allow for chemical attachment of additional moieties, as outlined below for chromophore attachment.

In one embodiment, the collagen monomers have an amino acid triplet with the structure below, where the —O-L-Ch is in the "middle position" of the triplet:

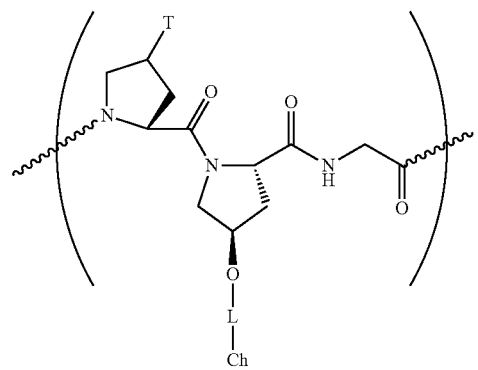

In one embodiment, the collagen monomers have an amino acid triplet with the structure below, where the —O-L-Ch is in the "first position" of the triplet:

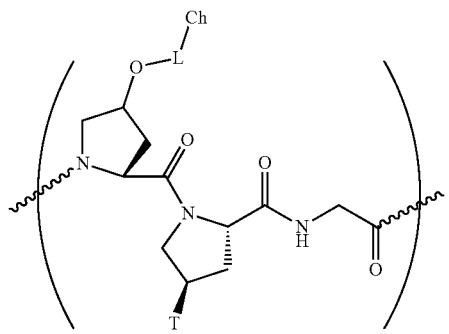

In one embodiment the collagen monomers have an amino acid triplet with the structure below, where $S_1$ and $S_2$ are independently selected from —OH, —H and -L-Ch, wherein one and only one of $S_1$ and $S_2$ are -L-Ch.

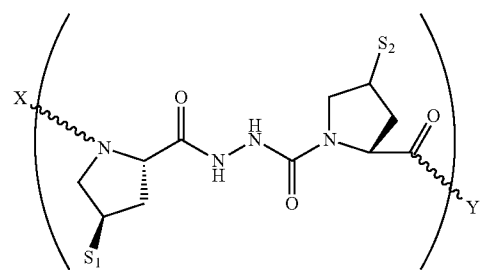

An additional chromophore structure of the invention is shown below:

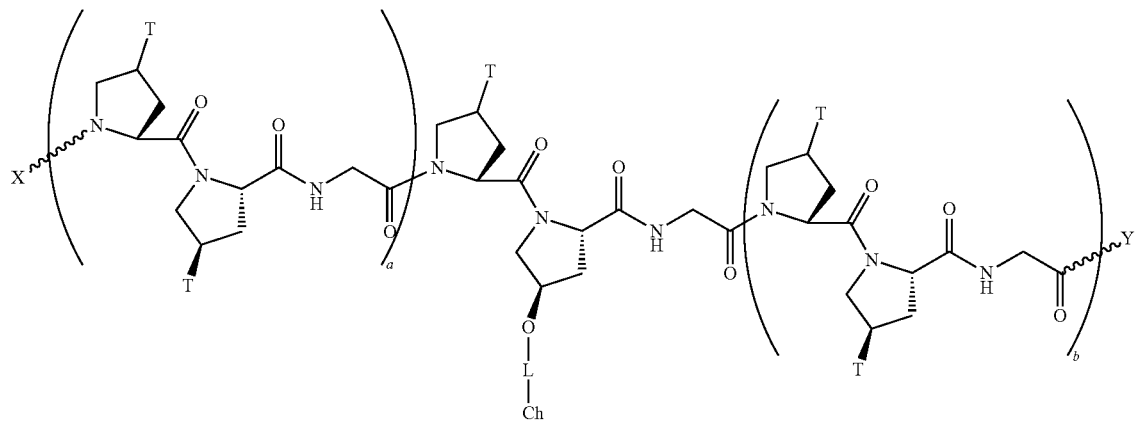

Accordingly, the present invention provides triplets comprising chromophores, generally linked to the amino acid backbone using the oxygen atom of a hydroxyproline residue and a linker.

Suitable linkers can be any flexible linker comprising alkyl group and heteroalkyl group linkers, generally at least two carbon atoms with optional heteroatoms such as nitrogen atoms. By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Alkyl also includes heteroalkyl, with heteroatoms of sulfur, oxygen, nitrogen, and silicone being preferred. In addition, the linkers can contain additional functionalities for solubility if needed.

Accordingly, the present invention provides triplets comprising chromophores. Suitable chromophores include, but are not limited to, optical dyes, including, but not limited to, chromophores, phosphors and fluorophores, with the latter being specific in many instances. Suitable non-fluorescent chromophores include rylene dyes, based on perylene frameworks, including perylenediimide and other poly(perinaphthalene)s—such as terrylene, quarterrylene. Fluorophores can be either "small molecule" fluores, or proteinaceous fluores. By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, entirely incorporated by reference.

As shown in FIG. 24 and FIG. 25, the present invention provides a number of chromophore collagen monomers and triplexes.

REFERENCES FOR EXAMPLES 5, 6 AND 7

1. Atwood J L, Lehn J M. Comprehensive supramolecular chemistry. 1st ed. New York: Pergamon; 1996.
2. Lehn J M. Supramolecular chemistry: receptors, catalysts, and carriers. Science. 1985; 227(4689):849-56. Epub 1985 Feb. 22. doi: 10.1126/science.227.4689.849. PubMed PMID: 17821215.
3. Lehn J M. Supramolecular chemistry. Science. 1993; 260(5115):1762-3. Epub 1993/06/18. PubMed PMID: 8511582.
4. Lehn J M. Supramolecular chemistry: concepts and perspectives: a personal account built upon the George Fisher Baker lectures in chemistry at Cornell University [and] Lezioni Lincee, Accademia nazionale dei Lincei, Roma. Weinheim; New York: VCH; 1995. x, 271 p. p.
5. Lehn J M. Toward complex matter: supramolecular chemistry and self-organization. Proc Natl Acad Sci USA. 2002; 99(8):4763-8. Epub 2002 Apr. 4. doi: 10.1073/pnas.072065599. PubMed PMID: 11929970; PMCID: 122664.
6. Lehn J M. Constitutional dynamic chemistry: bridge from supramolecular chemistry to adaptive chemistry. Top Curr Chem. 2012; 322:1-32. Epub 2011 Dec. 16. doi: 10.1007/128_2011_256. PubMed PMID: 22169958.
7. Terfort A, Bowden N, Whitesides G M. Three-dimensional self-assembly of millimeter-scale components. Nature. 1997; 386(6621): 162-4. doi: Doi 10.1038/386162a0. PubMed PMID: ISI:A1997WM97300058.
8. Whitesides G M. Molecular recognition in water. Abstr Pap Am Chem S. 2013; 245. PubMed PMID: ISI: 000324303603036.
9. Whitesides G M, Mathias J P, Seto C T. Molecular Self-Assembly and Nanochemistry—a Chemical Strategy for the Synthesis of Nanostructures. Science. 1991; 254 (5036): 1312-9. doi: Doi 10.1126/Science.1962191. PubMed PMID: ISI:A1991GR77700041.
10. Whitesides G M, Simanek E E, Mathias J P, Seto C T, Chin D N, Mammen M, Gordon D M. Noncovalent Synthesis—Using Physical-Organic Chemistry to Make Aggregates. Accounts of chemical research. 1995; 28(1):37-44. doi: Doi 10.1021/Ar00049a006. PubMed PMID: ISI: A1995QD24000006.

11. Shoulders M D, Raines R T. Collagen structure and stability. Annu Rev Biochem. 2009; 78:929-58. Epub 2009 Apr. 7. doi: 10.1146/annurev.biochem.77.032207.120833. PubMed PMID: 19344236; PMCID: 2846778.
12. Frischmann P D, Mahata K, Würthner F. Powering the future of molecular artificial photosynthesis with light-harvesting metallosupramolecular dye assemblies. Chemical Society reviews. 2013; 42:1847-70. doi: 10.1039/c2cs35223k. PubMed PMID: 22850767.
13. Wasielewski M R. Self-assembly strategies for integrating light harvesting and charge separation in artificial photosynthetic systems. Accounts of chemical research. 2009; 42:1910-21. doi: 10.1021/ar9001735. PubMed PMID: 19803479.
14. Okuyama K. Revisiting the molecular structure of collagen. Connective tissue research. 2008; 49(5):299-310. Epub 2008 Nov. 11. doi: 10.1080/03008200802325110. PubMed PMID: 18991083.
15. Kramer R Z, Vitagliano L, Bella J, Berisio R, Mazzarella L, Brodsky B, Zagari A, Berman H M. X-ray crystallographic determination of a collagen-like peptide with the repeating sequence (Pro-Pro-Gly). J Mol Biol. 1998; 280(4):623-38. Epub 1998 Jul. 25. doi: 10.1006/jmbi.1998.1881. PubMed PMID: 9677293.
16. Okuyama K, Okuyama K, Arnott S, Takayanagi M, Kakudo M. Crystal and molecular structure of a collagen-like polypeptide (Pro-Pro-Gly)10. J Mol Biol. 1981; 152 (2):427-43. Epub 1981 Oct. 25. PubMed PMID: 7328660.
17. Rich A, Crick F H. The molecular structure of collagen. J Mol Biol. 1961; 3:483-506. Epub 1961 Oct. 1. PubMed PMID: 14491907.
18. Ramachandran G N, Kartha G. Structure of collagen. Nature. 1954; 174(4423):269-70. Epub 1954 Aug. 7. PubMed PMID: 13185286.
19. Ramachandran G N, Kartha G. Structure of collagen. Nature. 1955; 176(4482):593-5. Epub 1955 Sep. 24. PubMed PMID: 13265783.
20. Bella J, Eaton M, Brodsky B, Berman H M. Crystal and molecular structure of a collagen-like peptide at 1.9 Å resolution. Science. 1994; 266(5182):75-81. Epub 1994 Oct. 7. PubMed PMID: 7695699.
21. Bella J, Brodsky B, Berman H M. Hydration structure of a collagen peptide. Structure. 1995; 3(9):893-906. Epub 1995 Sep. 15. PubMed PMID: 8535783.
22. van Goor H, Coers W, van der Horst M L, Huitema S, Suurmeijer A J. Distribution of cytoskeletal proteins, integrins, leukocyte adhesion molecules and extracellular matrix proteins in plastic-embedded human and rat kidneys. Analytical and quantitative cytology and histology/the International Academy of Cytology [and] American Society of Cytology. 2001; 23(5):345-54. Epub 2001 Nov. 6. PubMed PMID: 11693560.
23. Berisio R, Vitagliano L, Mazzarella L, Zagari A. Recent progress on collagen triple helix structure, stability and assembly. Protein Pept Lett. 2002; 9(2): 107-16. Epub 2002/07/27. PubMed PMID: 12141907.
24. Holmgren S K, Bretscher L E, Taylor K M, Raines R T. A hyperstable collagen mimic. Chemistry & biology. 1999; 6:63-70. doi: 10.1016/S1074-5521(99)80003-9. PubMed PMID: 10021421.
25. Shoulders M D, Kotch F W, Choudhary A, Guzei I A, Raines R T. The aberrance of the 4S diastereomer of 4-hydroxyproline. J Am Chem Soc. 2010; 132(31):10857-65. Epub 2010/08/05. doi: 10.1021/ja103082y. PubMed PMID: 20681719; PMCID: 2931826.
26. Kramer R Z, Bella J, Mayville P, Brodsky B, Berman H M. Sequence dependent conformational variations of collagen triple-helical structure. Nature structural biology. 1999; 6(5):454-7. Epub 1999 May 20. doi: 10.1038/8259. PubMed PMID: 10331873.
27. Holmgren S K, Taylor K M, Bretscher L E, Raines R T. Code for collagen's stability deciphered. Nature. 1998; 392(6677):666-7. Epub 1998 May 16. doi: 10.1038/33573. PubMed PMID: 9565027.
28. Lee J, Chmielewski J. Folding studies of pH-dependent collagen peptides. Chem Biol Drug Des. 2010; 75(2): 161-8. Epub 2009 Dec. 24. doi: 10.1111/j.1747-0285.2009.00929.x. PubMed PMID: 20028399.
29. Lee S G, Lee J Y, Chmielewski J. Investigation of pH-dependent collagen triple-helix formation. Angew Chem Int Ed Engl. 2008; 47(44):8429-32. Epub 2008 Sep. 26. doi: 10.1002/anie.200802224. PubMed PMID: 18816568.
30. Pires M M, Lee J, Emenwein D, Chmielewski J. Controlling the morphology of metal-promoted higher ordered assemblies of collagen peptides with varied core lengths. Langmuir. 2012; 28(4):1993-7. Epub 2011 Dec. 15. doi: 10.1021/1a203848r. PubMed PMID: 22165843.
31. Przybyla D E, Chmielewski J. Higher-order assembly of collagen peptides into nano- and microscale materials. Biochemistry-Us. 2010; 49(21):4411-9. Epub 2010 Apr. 27. doi: 10.1021/bi902129p. PubMed PMID: 20415447.
32. Przybyla D E, Rubert Perez C M, Gleaton J, Nandwana V, Chmielewski J. Hierarchical assembly of collagen peptide triple helices into curved disks and metal ion-promoted hollow spheres. J Am Chem Soc. 2013; 135(9): 3418-22. Epub 2013 Feb. 14. doi: 10.1021/ja307651e. PubMed PMID: 23402552.
33. Rubert Perez C M, Rank L A, Chmielewski J. Tuning the thermosensitive properties of hybrid collagen peptide-polymer hydrogels. Chem Commun (Camb). 2014; 50(60):8174-6. Epub 2014 Jun. 14. doi: 10.1039/c4cc03171g. PubMed PMID: 24926620.
34. Jalan A A, Hartgerink J D. Pairwise interactions in collagen and the design of heterotrimeric helices. Current opinion in chemical biology. 2013; 17(6):960-7. Epub 2013/11/21. doi: 10.1016/j.cbpa.2013.10.019. PubMed PMID: 24252327.
35. O'Leary L E, Fallas J A, Bakota E L, Kang M K, Hartgerink J D. Multi-hierarchical self-assembly of a collagen mimetic peptide from triple helix to nanofibre and hydrogel. Nature chemistry. 2011; 3(10):821-8. Epub 2011 Sep. 24. doi: 10.1038/nchem.1123. PubMed PMID: 21941256.
36. Fallas J A, O'Leary L E, Hartgerink J D. Synthetic collagen mimics: self-assembly of homotrimers, heterotrimers and higher order structures. Chemical Society reviews. 2010; 39(9):3510-27. Epub 2010 Aug. 3. doi: 10.1039/b919455j. PubMed PMID: 20676409.
37. Cejas M A, Kinney W A, Chen C, Vinter J G, Almond H R, Jr., Balss K M, Maryanoff C A, Schmidt U, Breslav M, Mahan A, Lacy E, Maryanoff B E. Thrombogenic collagen-mimetic peptides: Self-assembly of triple helix-based fibrils driven by hydrophobic interactions. Proc Natl Acad Sci USA. 2008; 105(25):8513-8. Epub 2008 Jun. 19. doi: 10.1073/pnas.0800291105. PubMed PMID: 18559857; PMCID: 2438399.
38. Cejas M A, Kinney W A, Chen C, Leo G C, Tounge B A, Vinter J G, Joshi P P, Maryanoff B E. Collagen-related peptides: self-assembly of short, single strands into a functional biomaterial of micrometer scale. J Am Chem 39. Erdmann R S, Wennemers H. Conformational stability of triazolyl functionalized collagen triple helices. Bioorganic & medicinal chemistry. 2013; 21(12):3565-8. Epub 2013/04/04. doi: 10.1016/j.bmc.2013.02.046. PubMed PMID: 23548629.
40. Siebler C, Erdmann R S, Wennemers H. From azidoproline to functionalizable collagen. Chimia (Aarau). 2013; 67(12-13):891-5. Epub 2013 Jan. 1. doi: 10.2533/chimia.2013.891. PubMed PMID: 24594333.
41. Erdmann R S, Wennemers H. Effect of sterically demanding substituents on the conformational stability of the collagen triple helix. J Am Chem Soc. 2012; 134(41): 17117-24. Epub 2012 Sep. 21. doi: 10.1021/ja3066418. PubMed PMID: 22992124.
42. Erdmann R S, Wennemers H. Conformational stability of collagen triple helices functionalized in the Yaa position by click chemistry. Organic & biomolecular chemistry. 2012; 10(10): 1982-6. Epub 2012 Jan. 24. doi: 10.1039/c2ob06720j. PubMed PMID: 22266764.
43. Erdmann R S, Wennemers H. Functionalizable collagen model peptides. J Am Chem Soc. 2010; 132(40):13957-9. Epub 2010 Sep. 21. doi: 10.1021/ja103392t. PubMed PMID: 20849115.
44. Jenkins C L, Vasbinder M M, Miller S J, Raines R T. Peptide bond isosteres: ester or (E)-alkene in the backbone of the collagen triple helix. Organic letters. 2005; 7(13):2619-22. Epub 2005 Jun. 17. doi: 10.1021/ol050780m. PubMed PMID: 15957905.
45. Dai N, Etzkorn F A. Cis-trans proline isomerization effects on collagen triple-helix stability are limited. J Am Chem Soc. 2009; 131(38):13728-32. Epub 2009 Sep. 4. doi: 10.1021/ja904177k. PubMed PMID: 19725497.
46. Dai N, Wang X J, Etzkom F A. The effect of a trans-locked Gly-Pro alkene isostere on collagen triple helix stability. J Am Chem Soc. 2008; 130(16):5396-7. Epub 2008 Mar. 28. doi: 10.1021/ja711021m. PubMed PMID: 18366169.
47. Shah N K, Brodsky B, Kirkpatrick A, Ramshaw J A. Structural consequences of D-amino acids in collagen triple-helical peptides. *Biopolymers*. 1999; 49(4):297-302. Epub 1999/03/18. doi: 10.1002/(SICI)1097-0282 (19990405)49:4<297::AID-BIP4>3.0.CO; 2-Q. PubMed PMID: 10079768.
48. Teo Y N, Kool E T. DNA-multichromophore systems. Chemical reviews. 2012; 112:4221-45. doi: 10.1021/cr100351g. PubMed PMID: 22424059.
49. Rybtchinski B, Sinks L E, Wasielewski M R. Combining Light-Harvesting and Charge Separation in a Self-Assembled Artificial Photosynthetic System Based on Perylenediimide Chromophores. J Am Chem Soc. 2004; 126:12268-9. doi: 10.1021/ja0460514. PubMed PMID: 15453751.
50. Elemans J A A W, van Hameren R, Nolte R J M, Rowan A E. Molecular Materials by Self-Assembly of Porphyrins, Phthalocyanines, and Perylenes. Advanced Materials. 2006; 18:1251-66. doi: 10.1002/adma.200502498.
51. Gorl D, Zhang X, Wirthner F. Molecular assemblies of perylene bisimide dyes in water. Angewandte Chemie (International ed in English). 2012; 51:6328-48. doi: 10.1002/anie.201108690. PubMed PMID: 22573415.
52. González-Rodriguez D, Schenning A P H J. Hydrogen-bonded Supramolecular it-Functional Materials †. Chem Mater. 2011; 23:310-25. doi: 10.1021/cm101817h.
53. Li S-L, Xiao T, Lin C, Wang L. Advanced supramolecular polymers constructed by orthogonal self-assembly. Chemical Society reviews. 2012; 41:5950-68. doi: 10.1039/c2cs35099h. PubMed PMID: 22773054.
54. Janssen P Ga, Vandenbergh J, van Dongen J L J, Meijer E W, Schenning A P H J. ssDNA templated self-assembly of chromophores. J Am Chem Soc. 2007; 129:6078-9. doi: 10.1021/ja0711967. PubMed PMID: 17447768.
55. Benvin A L, Creeger Y, Fisher G W, Ballou B, Waggoner A S, Armitage B A. Fluorescent DNA nanotags: supramolecular fluorescent labels based on intercalating dye arrays assembled on nanostructured DNA templates. J Am Chem Soc. 2007; 129(7):2025-34. Epub 2007 Jan. 30. doi: 10.1021/ja066354t. PubMed PMID: 17256855; PMCID: 2532517.
56. Malinovskii V L, Wenger D, Hiner R. Nucleic acid-guided assembly of aromatic chromophores. Chemical Society reviews. 2010; 39:410-22. doi: 10.1039/b910030j. PubMed PMID: 20111767.
57. Bretscher L E, Jenkins C L, Taylor K M, DeRider M L, Raines R T. Conformational Stability of Collagen Relies on a Stereoelectronic Effect. J Am Chem Soc. 2001; 123:777-8. doi: 10.1021/ja005542v.
58. Eberhardt E S, Panisik N, Raines R T. Inductive Effects on the Energetics of Prolyl Peptide Bond Isomerization: Implications for Collagen Folding and Stability. J Am Chem Soc. 1996; 118:12261-6. doi: 10.1021/ja9623119. PubMed PMID: 21451735.
59. Ghoroghchian P P, Frail P R, Susumu K, Blessington D, Brannan A K, Bates F S, Chance B, Hammer D A, Therien M J. Near-infrared-emissive polymersomes: self-assembled soft matter for in vivo optical imaging. P Natl Acad Sci USA. 2005; 102:2922-7. doi: 10.1073/pnas.0409394102. PubMed PMID: 15708979.
60. Szent-Gyorgyi C, Schmidt B F, Fitzpatrick JaJ, Bruchez M P. Fluorogenic dendrons with multiple donor chromophores as bright genetically targeted and activated probes. J Am Chem Soc. 2010; 132:11103-9. doi: 10.1021/ja9099328. PubMed PMID: 20698676.
61. Foster S, Finlayson C E, Keivanidis P E, Huang Y-S, Hwang I, Friend R H, Otten M B J,
Lu L-P, Schwartz E, Nolte R J M, Rowan A E. Improved Performance of Perylene-Based Photovoltaic Cells Using Polyisocyanopeptide Arrays. Macromolecules. 2009; 42:2023-30. doi: 10.1021/ma801959w.
62. Schmidt-Mende L, Fechtenkötter A, Müllen K, Moons E, Friend R H, MacKenzie J D. Self-organized discotic liquid crystals for high-efficiency organic photovoltaics. Science (New York, N.Y.). 2001; 293:1119-22. doi: 10.1126/science.293.5532.1119. PubMed PMID: 11498585.
63. Yashima E, Maeda K, Iida H, Furusho Y, Nagai K. Helical polymers: synthesis, structures, and functions. Chemical reviews. 2009; 109:6102-211. doi: 10.1021/cr900162q. PubMed PMID: 19905011.
64. Yuan Z, Lee S L, Chen L, Li C, *Mali* K S, De Feyter S, Mullen K. Processable Rylene Diimide Dyes up to 4 nm in Length: Synthesis and STM Visualization. Chemistry. 2013. Epub 2013 Aug. 21. doi: 10.1002/chem.201302086. PubMed PMID: 23955951.
65. Fron E, Puhl L, Oesterling I, Li C, Mullen K, De Schryver F C, Hofkens J, Vosch T. Energy transfer pathways in a rylene-based Triad. Chemphyschem. 2011; 12(3):595-608. Epub 2011 Feb. 24. doi: 10.1002/cphc.201000665. PubMed PMID: 21344593.
66. Haase M, Hubner C G, Nolde F, Mullen K, Basche T. Photoblinking and photobleaching of rylene diimide dyes.

Phys Chem Chem Phys. 2011; 13(5):1776-85. Epub 2010/12/15. doi: 10.1039/c0cp01814g. PubMed PMID: 21152552.
67. Weil T, Vosch T, Hofkens J, Peneva K, Mullen K. The rylene colorant family—tailored nanoemitters for photonics research and applications. Angew Chem Int Ed Engl. 2010; 49(48):9068-93. Epub 2010 Oct. 26. doi: 10.1002/anie.200902532. PubMed PMID: 20973116.
68. Weil T, Abdalla M A, Jatzke C, Hengstler J, Mullen K. Water-soluble rylene dyes as high-performance colorants for the staining of cells. Biomacromolecules. 2005; 6(1): 68-79. Epub 2005 Jan. 11. doi: 10.1021/bm049674i. PubMed PMID: 15638506.
69. Weil T, Reuther E, Beer C, Mullen K. Synthesis and characterization of dendritic multichromophores based on rylene dyes for vectorial transduction of excitation energy. Chemistry. 2004; 10(6):1398-414. Epub 2004 Mar. 23. doi: 10.1002/chem.200305359. PubMed PMID: 15034884.
70. Lavis L D, Raines R T. Bright ideas for chemical biology. ACS chemical biology. 2008; 3(3): 142-55. Epub 2008 Mar. 22. doi: 10.1021/cb700248m. PubMed PMID: 18355003; PMCID: 2802578.
71. Conlon P, Yang C J, Wu Y, Chen Y, Martinez K, Kim Y, Stevens N, Marti A A, Jockusch S, Turro N J, Tan W. Pyrene excimer signaling molecular beacons for probing nucleic acids. J Am Chem Soc. 2008; 130(1):336-42. Epub 2007 Dec. 15. doi: 10.1021/ja076411y. PubMed PMID: 18078339; PMCID: 2531189.
72. Lecoq A, Boussard G, Marraud M, Aubry A. Crystal-State Conformation of 3 Azapeptides Containing the Azaproline Residue, a Beta-Turn Regulator. *Biopolymers*. 1993; 33(7): 1051-9. doi: Doi 10.1002/Bip.360330707. PubMed PMID: ISI:A1993LJ21500006.
73. Mizuno K, Boudko S P, Engel J, Bachinger H P. Kinetic hysteresis in collagen folding. Biophys J. 2010; 98(12): 3004-14. Epub 2010 Jun. 17. doi: 10.1016/j.bpj.2010.03.019. PubMed PMID: 20550913; PMCID: 2884267.
74. How People Learn: Brain, Mind, Experience, and School: Expanded Edition: The National Academies Press; 2000.
75. Knowing What Students Know: The Science and Design of Educational Assessment. Pellegrino J W, Chudowsky N, Glaser R, editors: The National Academies Press; 2001.
76. Scientific Research in Education. Shavelson R J, Towne L, editors: The National Academies Press; 2002.
77. Taking Science to School: Learning and Teaching Science in Grades K-8. Duschl R A, Schweingruber H A, Shouse A W, editors: The National Academies Press; 2007.
78. A Framework for K-12 Science Education: Practices, Crosscutting Concepts, and Core Ideas. Helen Q, Heidi S, Thomas K, editors: The National Academies Press; 2012.
79. Next Generation Science Standards: For States, By States: The National Academies Press; 2013.
80. Brown R C D, Hinks J D, Read D. A blended-learning approach to supporting students in organic chemistry: methodology and outcomes. New Directions in the Teaching of Physical Sciences. 2012; 8:33-7.
81. Supasorn S, Kamsai L, Promarak V. Enhancement of Learning Achievement of Organic Chemistry Using Inquiry-based Semi-small Scale Experiments (SSSEs). Procedia-Social and Behavioral Sciences. 2014; 116(0): 769-74. doi: http://dx.doi.org/10.1016/j.sbspro.2014.01.295.
82. McClary L M, Bretz S L. Development and assessment of a diagnostic tool to identify organic chemistry students' alternative conceptions related to acid strength. International Journal of Science Education. 2012; 34(15):2317-41

Example 8: Determination of Whether Collagenase Enzymes Recognize and/or Bind to Aza-Glycine Containing Collagen Peptides Studies were conducted on collagenase degradation of aza-glycine containing collagen peptides such as Ac-(azGPO)$_4$-NH$_2$ (CMP 14) and discovered that they are not hydrolyzed by collagenase enzymes. This important observation raised question: do collagenase enzymes even recognize and/or bind to aza-glycine containing collagen peptides? Experiments were conducted directed at answering this question by using Ac-(azGPO)$_n$-NH$_2$ (CMP-14) as a collagenase inhibitor.

A collagenase inhibition titration assay was conducted using CD as the read out for degraded collagen peptide. For initial control collagenase degradation experiments Ac-(POG)$_7$-NH$_2$ (CMP 1) as a substrate for collagenase enzymatic degradation were utilized. Different amounts of the potential inhibitor Ac-(azGPO)$_4$-NH$_2$ were then added in to see if increasing the amount of this collagen azapeptide would decrease the rate of enzymatic digestion of the natural peptide Ac-(POG)$_7$-NH$_2$. Enzyme solutions were immediately added into the mixture of the two peptides and CD was used to monitor the conformational change during a time course of 8 h. The full CD spectrum was monitored over this time and the results are shown in FIG. 37 with the ratio of Ac-(POG)$_7$-NH$_2$: Ac-(azGPO)$_4$-NH$_2$ indicated.

The obtained CD signals at several representative wavelengths were normalized and the percentages of substrate remaining were plotted as a function of time for each equivalence of the potential inhibitor Ac-(azGPO)$_4$-NH$_2$ (FIG. 37). The rate of enzymatic digestion of Ac-(POG)$_7$-NH$_2$ decreased as the amount of Ac-(azGPO)$_4$-NH$_2$ increased from 0.5 eq to 1.0 eq. Surprisingly, as the equivalence of Ac-(azGPO)$_4$-NH$_2$ increased to 1.1 eq, a nearly quantitative inhibition was observed. A plot of remaining substrate concentration shows that >95% Ac-(POG)$_7$-NH$_2$ remained intact in the presence of the inhibitor peptide while only 7% substrate remained in the absence of the inhibitor after 80 minutes of collagenase treatment (FIG. 37). MALDI-TOF MS experiments were performed and the results showed that no substrate remained in cases where the amount of the potential inhibitor Ac-(azGPO)$_4$-NH$_2$ was less than 1.1 equivalent; however, clear peaks were observed for intact Ac-(POG)$_7$-NH$_2$ as well as the inhibitor Ac-(azGPO)$_4$-NH$_2$ when 1.1 eq. or more of Ac-(azGPO)$_4$-NH$_2$ was added to the reaction mixture.

The conclusion from the studies is that Ac-(azGPO)$_4$-NH$_2$ can interact with collagenase enzymes and inhibit enzymatic cleavage of a collagen peptide normally degraded by the enzymes. This result opens the door for using aza-glycine containing collagen peptides as inhibitors of the enzyme-collagen PPI interface. Additionally, aza-glycine containing collagen peptides will serve as a valuable tool for structural biology, especially since all reported crystal structures of MMPs and other collagenase enzymes to date are of catalytically inactive mutant enzymes. The possibility of crystallizing catalytically active enzymes such as MMP-1 or Cathepsin K bound to an aza-Gly containing collagen mimic resistant to cleavage could resolve many long-standing questions in collagenase structural biology.

TABLE 1

| Peptide Sequence | Mechanobiological Relevance |
|---|---|
| CMP-VEGF | Angiogenesis, VEGF Mimic |
| PEG-CMP | Attenuation of Cell Adhesion |
| Glu8-CMP-8 | Endothelial Cell Tubulogenesis |
| (PRG)$_4$(POG)$_4$(EOG)$_4$ | Fibrillogenesis |
| (POG)$_3$(PRG)(POG)$_4$ | Modulation of Intramolecular CMP Conformation |
| (GPR)(GQO)(GVM)(GFO) | von Willdebrand Factor (vWF) |
| (POG)$_4$(LOG)(POG)$_5$ | Microfibrillogenesis, Collagen Molecular Stability |
| (POG)$_4$(LOG)$_2$(POG)$_4$ | |
| RGD | Integrin Binding, Cellular Mechanosensing |
| LDV | |
| GPO | Superhelical Collagen Structure, |
| GPP | Characteristic Collagen Tripeptides |
| (PRG)$_4$(POG)$_4$(EOG)$_4$ | Zwitterionic Character, Electrostatic |
| (PKG)$_4$(POG)$_4$(DOG)$_4$ | Promotion of Helical Self-Assembly |

TABLE 2

Collagen binding sequences of biomedical relevance

| Collagen-binding molecule | High-resolution structure (PDB ID) Alone | High-resolution structure (PDB ID) Co-crystallized with triple-helical peptide | Binding Sequence | Biomedical Relevance |
|---|---|---|---|---|
| SPARC | 1BMO | 2V53 | GPOGPSGPRGQOGVMGFOGPKGNDGAO | Regulation of cell-matrix interactions Diverse roles in human carcinogenesis |
| VWF | 1AO3/1ATZ | 4DMU | RGQOGVMGF(1); also GPRGQOGVMGFO (2) | Anti-clotting agents |
| DDR2 | 2Z4F | 2WUH | GVMGFO; ≥2 minor sites as well | Cancer therapy |
| HSP47 | 4AU4 | 4AU3 | xGxRG | Anti-fibrotic therapies (3, 4) |
| MMP-1 | 2CLT | 4AUO | GPQGLAGQRGIVGLP | Cancer therapy |

(1) An B, Lin Y-S, Brodsky B. Advanced Drug Delivery Reviews. 2016; 97: 69-84. doi: 10.1016/j.addr.2015.11.013
(2) Boudko S. P.; Bächinger H. P. J Biol Chem. 2012; 287(53): 44536-45. doi: 10.1074/jbc.M112.417543.
(3) Yagi-Utsumi M, Yoshikawa S, Yamaguchi Y, Nishi Y, Kurimoto E, Ishida Y, Homma T, Hoseki J, Nishikawa Y, Koide T, Nagata K, Kato K. PLoS ONE. 2012; 7(9): e45930. doi: 10.1371/journal.pone.0045930.
(4) Nishikawa Y, Takahara Y, Asada S, Shigenaga A, Otaka A, Kitagawa K, Koide T. Biorg Med Chem. 2010; 18(11): 3767-75. doi: 10.1016/j.bmc.2010.04.054.

What is claimed is:

1. A composition comprising a first collagen monomer comprising at least seven amino acid triplets, wherein one of said triplets comprises an aza-glycine residue.

2. A composition according to claim 1 further comprising a second aza-glycine.

3. A composition according to claim 1 wherein said collagen monomer has the formula:

wherein
X is selected from the group consisting of (AA$_3$)$_n$, an AA, (AA)$_2$, acetyl;
Y is selected from the group consisting of (AA$_3$)$_m$, an AA, (AA)$_2$, amino;
n is an integer from 1 to 50;
m is an integer from 1 to 50;
T is independently selected from —OH and —H.

4. A composition according to claim 3 wherein said formula is:

5. A composition according to claim 3 wherein said formula is:

6. A composition according to claim 3 wherein said formula is:

7. A composition according to claim 3 wherein said formula is:

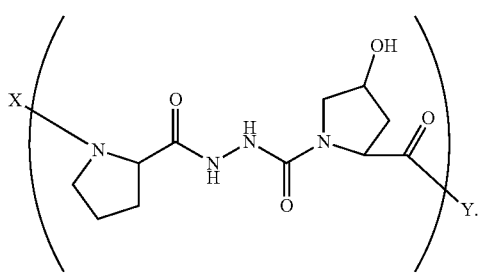

8. A composition according to claim 1 comprising a collagen monomer having the formula:

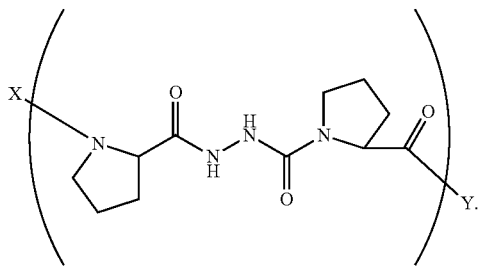

wherein
X is selected from the group consisting of $(AA_3)_n$, an AA, $(AA)_2$, acetyl;
Y is selected from the group consisting of $(AA_3)_m$, an AA, $(AA)_2$, amino;
n is an integer from 1 to 50;
m is an integer from 1 to 50;
T is independently selected from —OH and —H.

9. A composition according to claim 8 wherein said formula is:

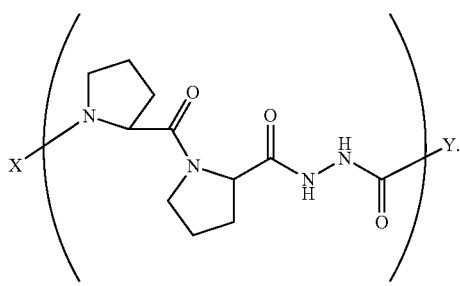

10. A composition according to claim 8 wherein said formula is:

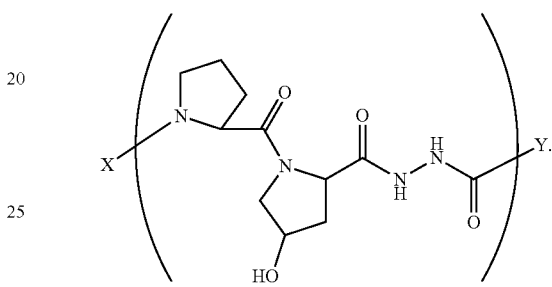

11. A composition according to claim 8 wherein said formula is:

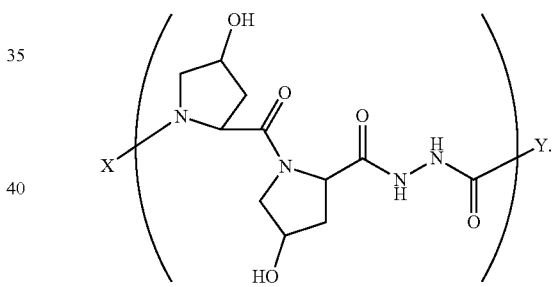

12. A composition according to claim 1 comprising a collagen monomer having the formula:

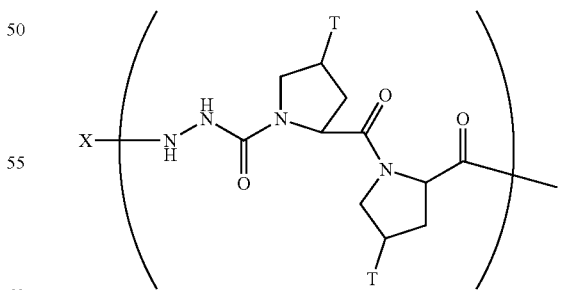

wherein
X is selected from the group consisting of $(AA_3)_n$, an AA, $(AA)_2$, acetyl;
Y is selected from the group consisting of $(AA_3)_m$, an AA, $(AA)_2$, amino;
n is an integer from 1 to 50;

m is an integer from 1 to 50;
T is independently selected from —OH and —H.

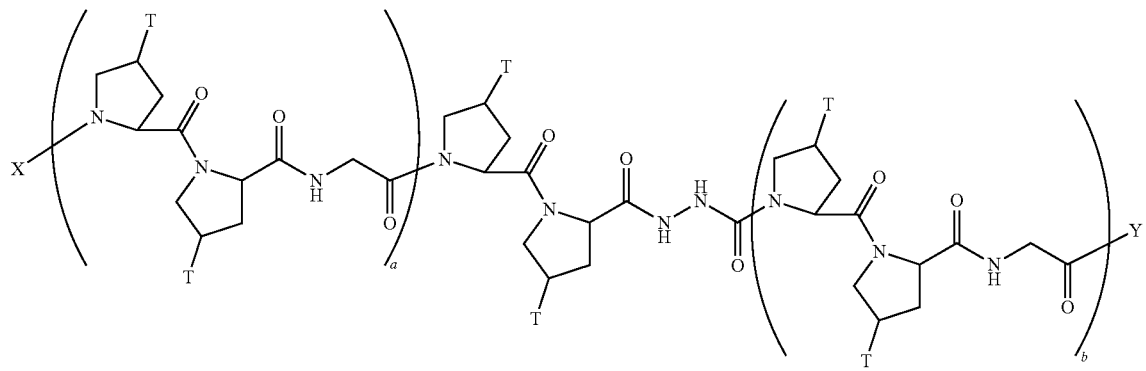

13. A composition comprising a peptide having the formula:

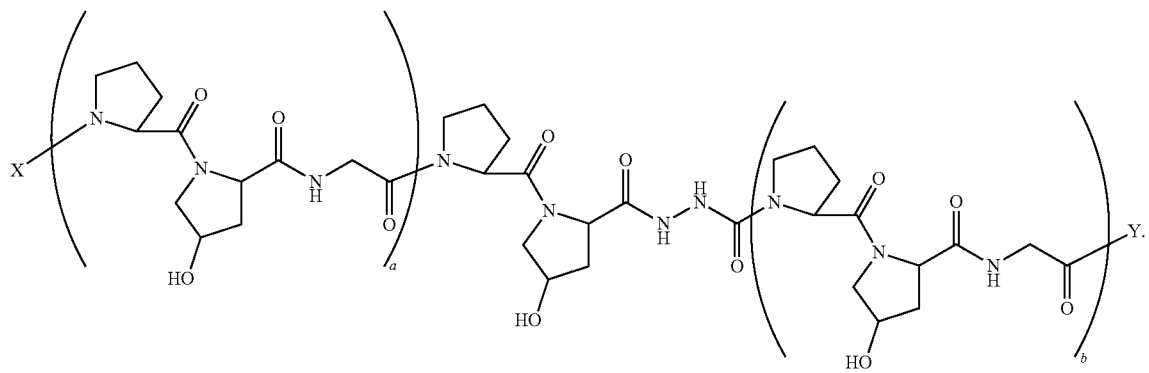

wherein
X is selected from the group consisting of acetyl, a label, an AA;
Y is selected from the group consisting of amino, a label, an AA; and
a and b are integers that together add up to 6 or more; and
T is independently selected from —OH and —H.

14. A composition according to claim 13 wherein said formula is:

15. A method of making a composition of claim 1, the method comprising the steps of:
(a) providing a POG tripeptide synthon and a solid support with a first protected amino acid or peptide synthon attached to the solid support;
(b) deprotecting the first protected amino acid or peptide synthon;
(c) coupling a second peptide synthon or an amino acid to the deprotected peptide synthon or amino acid;
(d) repeating the process until the desired aza-glycine sequence is completed; and
(e) cleaving the completed aza-glycine sequence from the solid support.

* * * * *